(12) United States Patent
Hutchinson et al.

(10) Patent No.: US 7,427,493 B2
(45) Date of Patent: Sep. 23, 2008

(54) RECOMBINANT GENES FOR POLYKETIDE MODIFYING ENZYMES

(75) Inventors: C. Richard Hutchinson, San Mateo, CA (US); Leonard Katz, Oakland, CA (US); Ralph Reid, San Rafael, CA (US); Zhihao Hu, Castro Valley, CA (US); Hugo Gramajo, Berkeley, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 690 days.

(21) Appl. No.: 10/611,442

(22) Filed: Jun. 30, 2003

(65) Prior Publication Data

US 2004/0203015 A1     Oct. 14, 2004

Related U.S. Application Data

(60) Provisional application No. 60/393,016, filed on Jun. 28, 2002.

(51) Int. Cl.
  *C12P 21/06* (2006.01)
(52) U.S. Cl. ............... 435/69.1; 435/6; 435/7.1; 435/320.1; 435/252
(58) Field of Classification Search ............. None
See application file for complete search history.

(56) References Cited

U.S. PATENT DOCUMENTS

| | | | |
|---|---|---|---|
| 5,098,837 A | 3/1992 | Beckmann et al. |
| 5,272,474 A | 12/1993 | Hilliard |
| 5,744,350 A | 4/1998 | Vinci et al. |
| 5,945,320 A | 8/1999 | Burgett et al. |
| 5,962,290 A | 10/1999 | Khosla et al. |
| 6,033,883 A | 3/2000 | Barr et al. |
| 6,066,271 A | 5/2000 | Hormadaly |
| 6,080,555 A | 6/2000 | Khosla et al. |
| 6,177,262 B1 | 1/2001 | Ziermann et al. |
| 6,251,636 B1 | 6/2001 | Betlach et al. |
| 6,261,816 B1 | 7/2001 | Khosla et al. |
| 6,274,560 B1 | 8/2001 | Khosla et al. |
| 6,303,342 B1 | 10/2001 | Julien et al. |
| 6,303,767 B1 | 10/2001 | Betlach et al. |
| 6,509,455 B1 | 1/2003 | Ashley et al. |
| 6,524,841 B1 * | 2/2003 | McDaniel et al. ........ 435/252.3 |

FOREIGN PATENT DOCUMENTS

| | | |
|---|---|---|
| EP | 0 791 656 | 8/1997 |
| WO | WO 93/13663 | 7/1993 |
| WO | WO 98/49315 | 11/1998 |
| WO | WO 99/03986 | 1/1999 |
| WO | WO 00/24907 | 5/2000 |
| WO | WO 00/44717 | 8/2000 |
| WO | WO 00/62873 | 10/2000 |
| WO | WO 00/63224 | 10/2000 |
| WO | WO 00/63225 | 10/2000 |
| WO | WO 00/63361 | 10/2000 |
| WO | WO 01/27284 | 4/2001 |

OTHER PUBLICATIONS

Seffernick et al. (J. Bacteriology, vol. 183, pp. 2405-2410, 2001).*
Volchegursky et al. (Molecular Microbiology, vol. 37 (4), pp. 752-762, 2000).*

* cited by examiner

*Primary Examiner*—Hope A Robinson
(74) *Attorney, Agent, or Firm*—Townsend and Townsend and Crew LLP

(57) ABSTRACT

Materials and methods to produce modified polyketides are disclosed. The biosynthesis, transfer and regulator genes for various sugars to effectuate polyketide modification are disclosed.

3 Claims, 3 Drawing Sheets

Figure 1 – Megalomicin Biosynthetic Gene Cluster
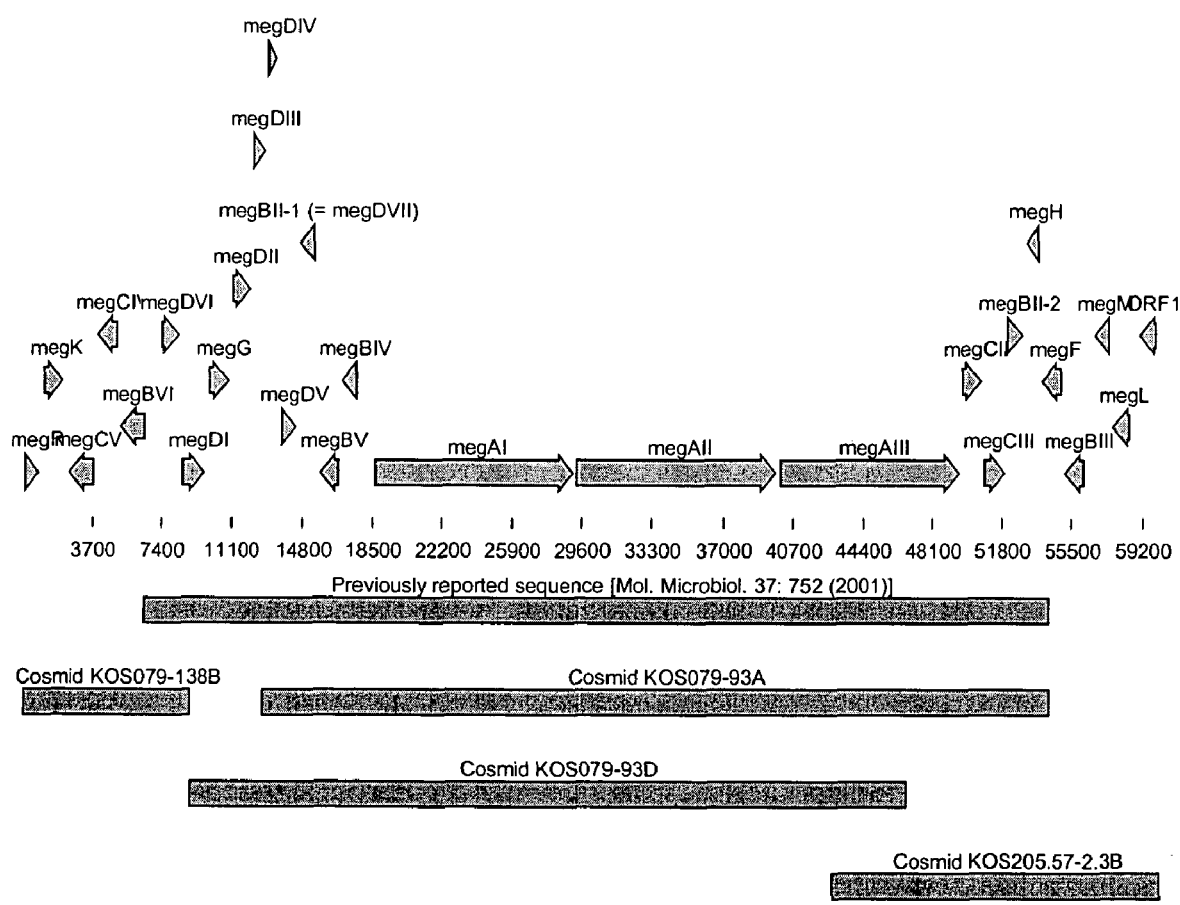

Figure 2 – Megalomicin Biosynthetic Pathway
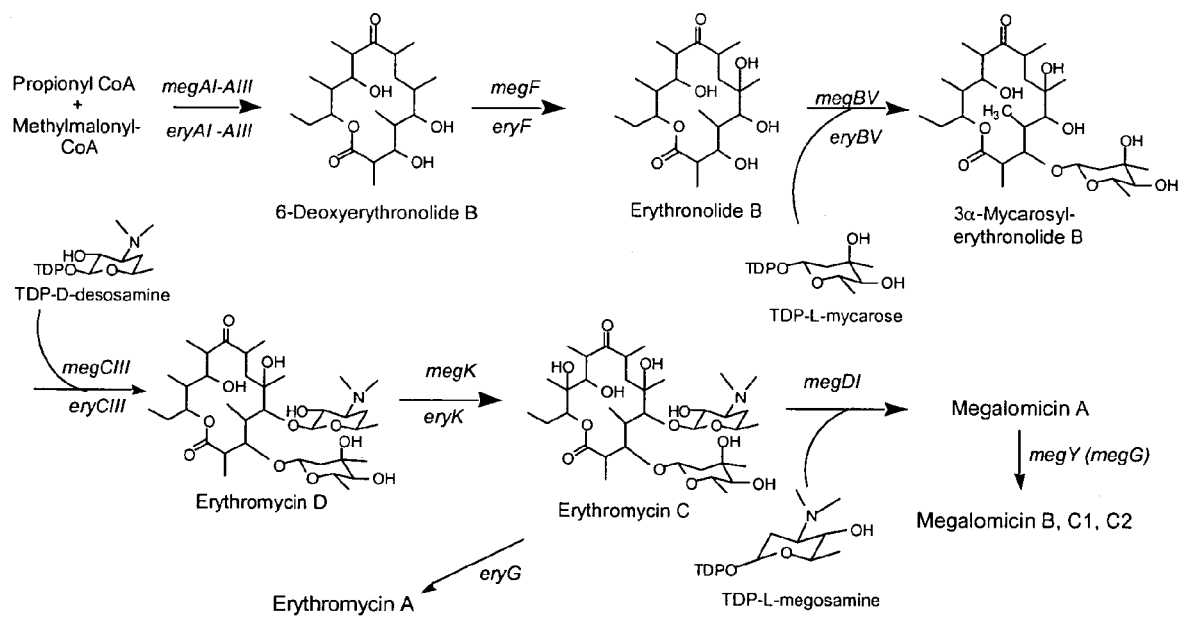

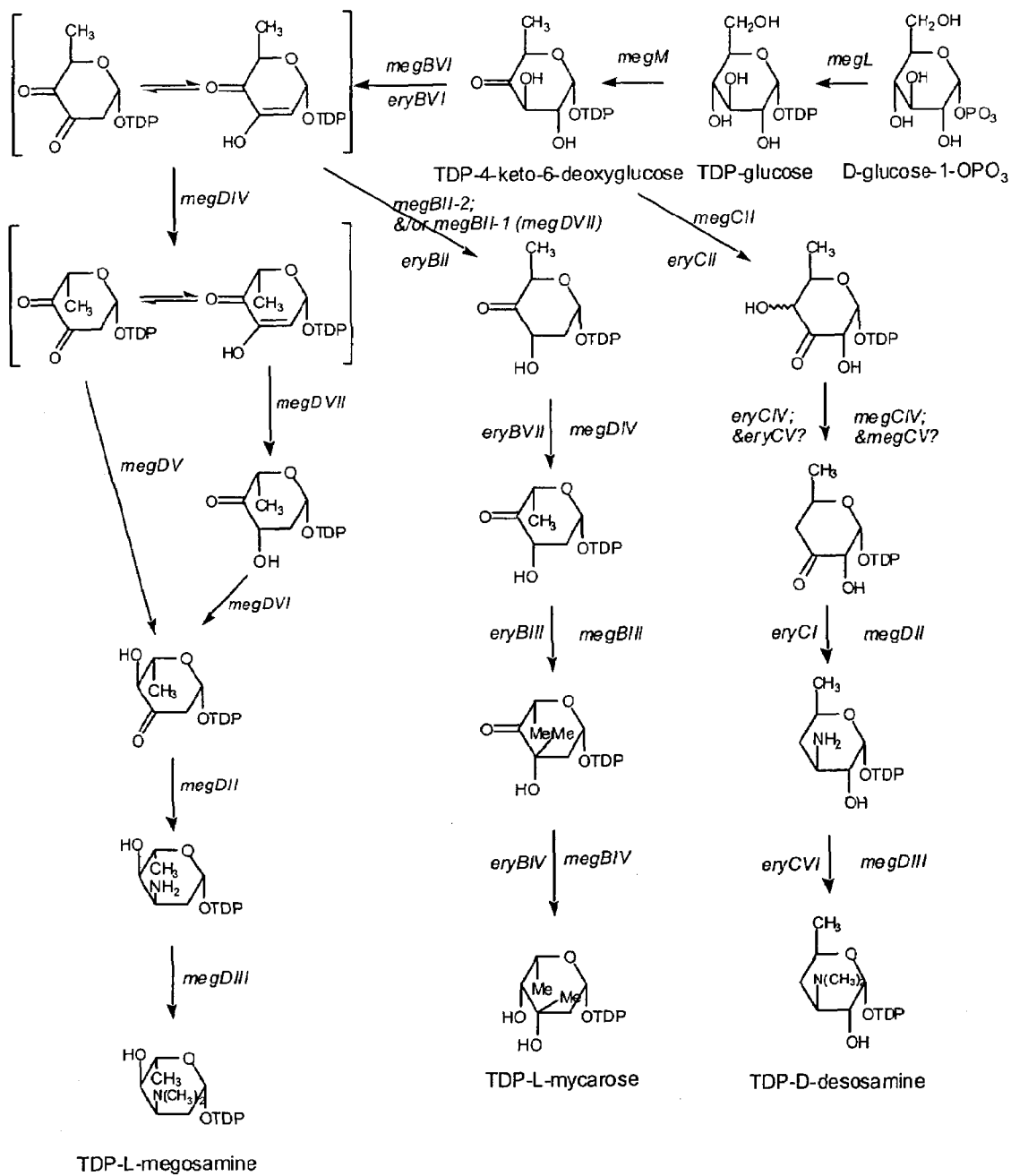
Figure 3 – Biosynthetic pathways for Megosamine, Mycarose and Desosamine

RECOMBINANT GENES FOR POLYKETIDE MODIFYING ENZYMES

CROSS-REFERENCE TO RELATED APPLICATIONS

This application claims benefit of U.S. Provisional Patent Application No. 60/393,016, filed Jun. 28, 2002, which is incorporated herein by reference in its entirety.

FIELD OF THE INVENTION

The present invention provides methods and materials for modifying polyketides by the addition of carbohydrate and other moieties to the polyketides. Polyketides are a diverse class of compounds with a wide variety of activities, including activities useful for medical, veterinary, and agricultural purposes. The present invention therefore relates to the fields of molecular biology, chemistry, recombinant DNA technology, medicine, animal health, and agriculture.

BACKGROUND OF THE INVENTION

Modular PKS enzymes are large, multi-subunit enzyme complexes that perform the biosynthesis of polyketide secondary metabolites. See O'Hagan, D., 1991 (a full citation of any reference referred to herein by last name of first author and year of publication is located at the end of this section). Examples of polyketides made by modular PKS enzymes include the antibiotic erythromycin, the immunosuppressant FK506, and the antitumor compound epothilone. See also PCT patent publication No. 93/13663 (erythromycin); U.S. Pat. No. 6,303,342 B1 (epothilone); U.S. Pat. No. 6,251,636 B1 (oleandolide); PCT publication WO 01/27284 A2 (megalomicin); U.S. Pat. No. 5,098,837 (tylosin); U.S. Pat. No. 5,272,474 (avermectin); U.S. Pat. No. 5,744,350 (triol polyketide); and European patent publication No. 791,656, now U.S. Pat. No. 5,945,320 (platenolide), each of which is incorporated herein by reference.

PCT publication WO 01/27284 A2 referenced above discloses the desosamine biosynthesis gene megCII encoding a 3,4-isomerase and glycosylyltransferase gene megCIII; the mycarose biosynthesis genes megBII (megBII-2) and megBIV encoding a 2,3-reductase and 4-ketoreductase respectively, and the mycarose glycosyltransferase gene megBV; the megosamine biosynthesis genes megDII, megDIII, megDIV, megDV, and megDVI, and the megosanine glycosyltransferase gene megDI. That publication made partial disclosures of megBVI (megT) and megF. The megBVI gene, which has dual function in mycarose and megosamine biosynthesis as a 2,3-dehydratase, was only partially disclosed (less than 10% of the nucleotide sequence) and was named megT. The megF genes sequence was disclosed in part (47%).

A large interest in PKS enzymes arises from the ability to manipulate the specificity or sequence of reactions catalyzed by PKSs to produce novel useful compounds. See U.S. Pat. No. 5,962,290 and McDaniel, R., et al., 2000, and Weissman, K. J et al. 2001. A number of plasmid-based heterologous expression systems have been developed for the engineering and expression of PKSs, including multiple-plasmid systems for combinatorial biosynthesis. See McDaniel, et al., 1993, Xue, et al., 1999, and Ziermann, et al., 2000, and U.S. Pat. Nos. 6,033,883 and 6,177,262; and PCT publication Nos. 00/63361 and 00/24907, each of which is incorporated herein by reference. Polyketides are often modified by P450 enzymes that hydroxylate the polyketide and by glycosyl transferase enzymes that glycosylate the polypeptide. Using recombinant technology, see PCT Pub. No. 98/49315, incorporated herein by reference, one can also hydroxylate and or glycosylate polyketides. Such technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

The class of polyketides includes the megalomicins, which are 6-O-glycosides of erythromycin C with acetyl or propionyl groups esterified to the 3''' or 4''' hydroxyls of the mycarose sugar. They were reported in 1969 as antibacterial agents produced by *Micromonospora megalomicea* sp. n. (Weinstein et al., 1969). The deoxyamino sugar at C-6 was named "megosamine" (Nakagawa et al., 1984). Therapeutic interest in megalomicin arose from several observed biological activities, including anti-bacterial activity, effects on protein trafficking in eukaryotic cells, inhibition of vesicular transport between the medial and trans Golgi, resulting in undersialylation of proteins, inhibition of the ATP-dependent acidification of lysosomes, anomalous glycosylation of viral proteins, antiviral activity against herpes, and as potent antiparasitic agents. Megalomicins are effective against *Plasmodium falciparum, Trypanosoma* sp. and *Leishmania donovani* (Bonay et al., 1998). As erythromycin does not have antiparasitic activity, the antiparasitic action of megalomicin is most probably related to the presence of the megosamine deoxyamino sugar at C-6.

The aglycone backbone of both megalomicin and erythromycin is the complex polyketide 6-deoxyerythronolide B (6-dEB), produced from the successive condensations of a propionyl-CoA starter unit and 6 methylmalonyl-CoA extender units (FIG. 2). Complex polyketides are assembled by modular polyketide synthases (PKSs), which are composed of multifunctional polypeptides that contain the activities (as enzymatic domains) for the condensation and subsequent reductions required to produce the polyketide chain (Katz, 1997; Cane et al., 1998).

The biosynthetic pathway of megalomicin is shown in FIG. 2. Both the megalomicin and erythromycin pathways are identical through the formation of erythromycin C, the penultimate intermediate of erythromycin A and megalomicin A. The megalomicin biosynthetic gene cluster has, in addition to the genes for the synthesis and attachment of the mycarose and desosamine sugars, a set of genes for synthesis and attachment of the unique deoxysugar L-megosamine. Making glycosylated and or/hydroxylated derivatives of aglycones through genetic engineering would be possible if one could transfer one or more of the megalomicin sugar biosynthesis and glycosyl-transferase, and P450 monooxygenase genes to another host. There exists a need for methods and materials to modify polyketides by P450 modification and/or the addition of sugar moieties to create active compounds in heterologous or native hosts. The present invention provides methods and compositions to meet those and other needs.

The following articles provide background information relating to the invention and are incorporated herein by reference.

Alarcon, B., et al. (1984), *Antiviral Res* 4: 231-243.
Alarcon, B., et al (1988), *FEBS Lett* 231:207-211.
Altschul, S. F., et al. (1990), *J Mol Biol* 215: 403-410.
Andersen, J. F., et al. (1992), *J Bacteriol* 174: 725-735.
Arisawa, A., et al. (1993), *Biosci Biotechnol Biochem* 57: 2020-2025.
Arisawa, A., et al. (1994), *Appl Environ Microbiol* 60:2657-2660.

Bierman, M., et al. (1992), *Gene* 118: 43-49.
Bisang, C., et al. (1999), *Nature* 401: 502-505.
Bonay, P., et al. (1996), *J Biol Chem* 271: 3719-3726.
Bonay, P., et al. (1997), *J Cell Sci* 110:1839-1849 (1997).
Bonay, P., et al. (1998), *Antimicrob Agents Chemother* 42: 2668-2673.
Brünker, P., et al. (1998), *Microbiology* 144: 2441-2448.
Butler, A. R., et al. (1999), *Chem Biol* 6: 287-292.
Cane, D. E., et al. (1998), *Science* 282: 63-68.
Cortés, J., et al. (1990), *Nature* 348:176-178.
Dhillon, N., et al. (1989), *Mol Microbiol* 3:1405-1414.
Donadio, S., and Katz, L. (1992), *Gene* 111: 51-60.
Donadio, S., et al. (1993), *Gene* 126: 147-151.
Donadio, S., et al. (1991), *Science* 252: 675-679.
Epp, J. K., et al. (1989), *Gene* 85: 293-301.
Gaisser, S., et al. (1997), *Mol Gen Genet* 256: 239-251.
Gokhale, R. S., et al. (1999), *Science* 284: 482-485.
Gu, H., et al. (1996), *Clin J Biotechnol* 12:147-152.
Hara, O., et al. (1992), *J Bacteriol* 174:5141-5144.
Haydock, S. F., et al. (1991), *Mol Gen Genet* 230: 120-128.
Hopwood, D. A., et al. (1985) *Genetic Manipulation of Streptomyces: A Laboratory Manual*. Norwich, UK: The John Innes Foundation.
Kakavas, S. J., Katz, L., and Stassi, D. (1997), *J Bacteriol* 79: 7515-7522.
Kao, C. M., et al. (1994a), *J Am Chem Soc* 116: 11612-11613.
Kao, C. M., et al. (1994b), *Science* 265: 509-512.
Katz, L. (1997), *Chem Rev* 97: 2557-2576.
Kuhstoss, S., et al. (1996), *Gene* 183:231-236.
McDaniel, R., et al. (1993), *Science* 262:1546-1557.
McDaniel, R., et al. (1999), *Proc Natl Acad Sci USA* 96:1846-1851.
McDaniel, R., et al. (2000), *Adv Bio Eng,* 73: 31-52.
Nakagawa, A., et al. (1984) Structure and stereochemistry of macrolides. In *Macrolide Antibiotics*. Omura, S. (ed.). New York: Academic Press, pp. 37-84.
O'Hagan, D., et al. (1991) The polyketide metabolites. Ellis Horwood, Chichester, UK.
Olano, C., et al. (1999), *Chem Biol* 6: 845-855.
Pereda, A., et al. (1997), *Gene* 193: 65-71.
Sambrook, J., Fritsch, E. F., and Maniatis, T. (1989). *Molecular Cloning: a Laboratory Manual*. Cold Spring Harbor, N.Y.: Cold Spring Harbor Laboratory Press.
Schwecke, T., et al. (1995), *Proc Natl Acad Sci USA* 92: 7839-7843.
Shah, S., et al. (2000), *J Antibiotics* 53: 502-508.
Stassi, D., et al. (1993), *J Bacterial* 175:182-189.
Summers, R. G., et al. (1997), *Microbiology* 143: 3251-3262.
Tang, L, et al. (1999), *Chem Biol* 6: 553-558.
Tang, L., et al. (2000), *Chem Biol* 7: 77-84.
van Wageningen, A., et al. (1998), *Chem Biol* 3:155-162.
Volchegursky, Y., et al. (2000), *Mol Microbiology* 37(4), 752-762.
Weber, J. M., et al. (1990), *J Bacteriol* 172: 2372-2383.
Weber, J. M., et al. (1991), *Science* 252: 114-117.
Weinstein, M. J., et al. (1969), *J Antibiot* 22: 253-258.
Weissman, K. J., et al. (2001), In H. A. Kirst et al. (ed.), Enzyme technologies for pharmaceutical and biotechnological applications, p. 427-470. Marcel Dekker, Inc. New York.
Xue, O., et al. (1999), *Proc Natl Acad Sci USA* 96:11740-11745.
Xue, Y., et al. (1998), *Proc Natl Acad Sci USA* 95: 12111-12116.
Zhao, L., et al. (1998), *J Am Chem Soc* 120: 10256-10257.
Ziermann, R., et al. (1999), *Biotechniques* 26: 106-110.
Ziermann, R., et al. (2000), *J Ind Microbial Biotech* 24: 46-50.

SUMMARY OF THE INVENTION

As described above, portions of the megalomicin PKS gene cluster DNA sequence have been disclosed in PCT publication WO 01/27284 A2. That publication disclosed the DNA sequence of mycarose biosynthesis genes BII (BII-2) and BIV and mycarose transferase gene megBV, desosamine biosynthesis gene megCII and desosamine transferase gene megCIII, and megosamine biosynthesis genes megDII, megDIII, megDIV, megDV, and megDVI, megDVII and megosamine transferase gene megDI, as well as a partial DNA sequence of megBVI (megT), which has dual function in mycarose and megosamine biosynthesis pathways, and megF.

The present invention provides the complete nucleotide sequence of the megF and megK genes, which encode monooxygenases of P450-type that hydroxylate at the C-6 and C-12 position of 6-dEB as well as recombinant vectors and host cells comprising such genes. The present invention also provides recombinant vectors and host cells comprising the genes megBIII and/or megBVI of the mycarose biosynthesis pathway (megBVI also functions in the megosamine biosynthesis pathway as a 2,3-dehydratase), megCIV and megCV of the desosamine biosynthesis pathway, and megBVI (formerly designated megT) of the megosamine biosynthesis pathway. The present invention also provides novel genes in recombinant form common to several desoxysugar biosynthesis pathways, including megM encoding a megosamine 6-dehydrogenase, and megL encoding a TDP-glucose synthase. The present invention also provides a recombinant PKS cluster regulatory gene megR isolated from the upstream region of the megalomicin PKS cluster. The recombinant genes of the present invention may be isolated from *Micromonospora megalomicea*, sp. *nigra*.

The present invention provides recombinant methods and materials for expressing genes useful in P450-mediated oxidation of a polyketide and/or the biosynthesis and transfer to a polyketide of mycarose, desosamine, and/or megosamine in recombinant host cells. More specifically, the genes and proteins isolated from *Micromonospora megalomicea*, sp. *nigra*, of the present invention are useful in the hydroxylation and glycosylation of polyketides by the addition of mycarose, desosamine, and/or megosamine to a polyketide. In particular the invention provides recombinant monooxygenases of P450 type megK and megF; recombinant mycarose synthesis genes megBIV, megBII (meg BII-2), megBIII, megBVI, and megDIV and recombinant mycarose transfer gene megBV; recombinant desosamine synthesis genes megCII, megCIV, megCV, megDII, megDIII and recombinant megCIII desosamine transfer gene; recombinant megosamine synthesis genes megDII, megDIII, megDIV, megDV, megDVII, megDVI, megBVI and the megosamine transfer gene megDI; and recombinant deoxysugar genes megM encoding a glucose-6-dehydratase, and megL encoding a TDP-glucose synthase (common to the desosamine, mycarose, and megosamine biosynthesis pathways). The invention also provides the proteins encoded by the recombinant genes of the present invention in isolated, purified, and/or recombinant form. The invention also provides novel polyketides produced by glycosylation mediated by the sugar biosynthesis and transfer genes and/or by hydroxylation mediated by the P450 genes isolated from the megalomicin PKS gene cluster of *Micromonospora megalomicea*, sp. *nigra*.

Thus, in one embodiment, the invention provides recombinant DNA compounds that comprise the C-6 hydroxylase (the megF gene), and C-12 hydroxylase (the megK gene), the desosamine biosynthesis and desosaminyl transferase enzymes and the recombinant proteins that can be produced from these nucleic acids in the recombinant host cells of the invention. In some embodiments, the invention provides an isolated, purified, or recombinant nucleic acid comprising a polyketide modifying gene, wherein said gene encodes one of the polyketide modifying enzymes MegR, MegF, MegK, MegCIV, MegCV, MegBVI, MegBIII, MegL, or MegM. In some embodiments, the nucleic acid is less than about 9.0 kilobases in length. In some embodiments, the nucleic acid does not also comprise one or more of the polyketide modifying genes megBI, megBV, megBIV, megCI, megCII, megDII, megDIII, megDIV, megDV, megDVII, and megY. In some embodiments, the gene encodes one of the polyketide modifying enzymes MegR, MegK, MegCIV, MegCV, or MegBVI. In some embodiments, the gene encodes one of the polyketide modifying enzymes MegF, MegBIII, MegL, or MegM. In some embodiments, the invention provides an isolated, purified, or recombinant nucleic acid containing genes for the biosynthesis and attachment of mycarose to a polyketide, where the genes include the megM, megL, megBIII, megBIV, megDIV, megBV, meg BII (megBII-2), and megBVI genes, and, optionally, the megF gene. In some embodiments, the polyketide modifying enzyme has an amino acid sequence that is encoded by SEQ ID NO: 1 or SEQ ID NO: 2, or hybridizes to SEQ ID NO: 1 or SEQ ID NO: 2 under stringent conditions, or has at least about 90% sequence identity to SEQ ID NO: 1 or SEQ ID NO: 2. In some embodiments, the polyketide modifying gene is operably linked to a heterologous promoter. In some embodiments, the invention provides an isolated, purified, or recombinant nucleic acid that contains a polyketide modifying enzyme gene megK, megCV, megCIV, megR, megBVI, megF, megBIII, megL, or megM.

The invention further provides isolated, purified, or recombinant nucleic acids containing genes for the biosynthesis and attachment of glycosyl units to a polyketide. In one embodiment, the invention provides isolated, purified, or recombinant nucleic acids containing genes for the biosynthesis and attachment of mycarose to a polyketide and/or hydroxylation of the polyketide, where the genes include the genes that encode the enzymes MegM, MegL, MegBIII, MegBIV, MegDIV, MEG BII (MegBII-2), MegBVI, optionally MegBV, and, optionally, MegF. In another embodiment, the invention provides an isolated, purified, or recombinant nucleic acid containing genes for the biosynthesis and attachment of megosamine to a polyketide, where the genes may include the genes that encode the enzymes MegM, MegL, MegCII, MegBVI, MegDIV, MegDV, MegDII, and MegDIII enzymes, and, optionally the MegDI enzyme. In a further embodiment, the invention provides an isolated, purified, or recombinant nucleic acid containing genes for the biosynthesis and attachment of megosamine to a polyketide, where the genes may include the genes that encode the enzymes MegM, MegL, MegCII, MegBVI, MegDIV, MegDVI, MegDVII, MegDII, and MegDIII enzymes, and, optionally, the MegDI enzyme. In yet a further embodiment, the invention provides an isolated, purified, or recombinant nucleic acid containing genes for the biosynthesis and attachment of desosamine to a polyketide, where the genes include the genes that encode the enzymes MegM, MegL, MegCII, MegCIV, MegCV, MegDII, and MegDIII enzymes, and, optionally, the MegCIII enzyme.

The invention also provides materials that include recombinant DNA compounds that encode the PKS modification enzymes TDP-hexose synthase (the megL gene for attachment of thymidinediphospho (TDP) glucose), and TDP hexose-4,6-dehydratase (the megM gene), and the recombinant proteins that can be produced from these nucleic acids in the recombinant host cells of the invention.

The invention also provides materials that include recombinant DNA compounds that encode the PKS cluster regulatory gene (megR).

The invention also provides a vector comprising the modifying genes megCII, megCIII, megBII, megK, megF, megBIII, megM, and megL.

The invention also provides a vector comprising the modifying genes megK, megCV, megCIV, and megBVI.

The invention also provides expression vectors that contain at least one of the polyketide modifying genes described above, e.g., a vector where the gene is operably linked to a promoter. In some embodiments, the polyketide modifying gene is megR, megF, megK, megCIV, megCV, megBVI, megBIII, megL, or megM.

The invention further provides cosmid vectors that contain at least one of the polyketide modifying genes described, above.

The invention further provides recombinant host cells containing at least one of the polyketide modifying genes described above. In some embodiments, the host cell expresses a polyketide modifying enzyme, where the enzyme is the MegK or MegF monooxygenase. In some embodiments, the host cell expresses a polyketide modifying enzyme encoded by a gene from a desosamine biosynthetic gene set, where the enzyme is MegCIV, MegCV, or MegCIII. In some embodiments, the host cell expresses a polyketide modifying enzyme encoded by a gene from a desosamine biosynthetic gene set, where the enzyme is MegCII, MegCIV, MegCV, or MegCIII. In some embodiments, the host cell expresses a polyketide modifying enzyme encoded by a gene from a megosamine biosynthetic gene set, where the enzyme is MegBVI or MegDI. In some embodiments, the host cell expresses a polyketide modifying enzyme encoded by a gene from a megosamine biosynthetic gene set, where the enzyme is MegDI, MegDII, MegDIII, MegDIV, MegDV, MegDVI, MegDVII, or MegBVI. In some embodiments, the host cell expresses a polyketide modifying enzyme encoded by a gene from a mycarose biosynthetic gene set, where the enzyme is MegBIII or MegBVI. In some embodiments, the host cell expresses a polyketide modifying enzyme encoded by a gene from a mycarose biosynthetic gene set, where the enzyme is MegBII, MegBIII, MegBIV, MegBV, or MegBVI. The invention further provides host cells that expreess a polyketide modifying gene that encodes a polyketide modifying enzyme MegR, MegF, MegK, MegCIV, MegCV, MegBVI, MegBIII, MegL, or MegM.

The invention also provides methods using the recombinant genes of the present invention to modify aglycones or polyketides.

The invention also provides materials that include recombinant DNA compounds that encode the PKS modification enzymes effectuating mycarose biosynthesis and glycosyltransferase enzymes and the recombinant proteins that can be produced from these nucleic acids in the recombinant host cells of the invention.

The invention also provides materials that include recombinant DNA compounds that encode the PKS modification enzymes effectuating desosamine biosynthesis and glycosyltransferase enzymes and the recombinant proteins that can be produced from these nucleic acids in the recombinant host cells of the invention.

The invention also provides materials that include recombinant DNA compounds that encode the PKS modification enzymes effectuating megosamine biosynthesis and glycosyltransferase enzymes and the recombinant proteins that can be produced from these nucleic acids in the recombinant host cells of the invention.

In one embodiment, the invention provides DNA molecules in isolated (i.e., not pure, but existing in a preparation in an abundance and/or concentration not found in nature) and/or purified (i.e., substantially free of contaminating materials or substantially free of materials with which the corresponding DNA would be found in nature) and/or recombinant (i.e., nucleic acid synthesized or otherwise manipulated in vitro) form. The DNA molecules of the invention may in some embodiments also comprise, in addition to sequences that encode polyketide modifying enzymes, sequences that encode polyketide synthase domains. For example, the DNA molecules of the invention may contain one or more sequences that encode one or more domains (or fragments of such domains) of one or more modules in one or more of the ORFs of the megalomicin or other PKS. Examples of PKS domains include the KS (beta-ketoacylsynthase), acyltransferase (AT), dehydratase (DH), ketoreductase (KR), enoylreductase (ER), acyl carrier protein (ACP), and thioesterase (TE) domains, for example, domains of at least 6 extender modules and loading module of the three proteins encoded by the three ORFs of the megalomicin PKS gene cluster.

In one embodiment, the present invention provides recombinant PKS modification enzymes including those that synthesize mycarose, desosamine, and megosamine moieties, those that transfer those sugar moieties to the polyketide 6-dEB, and those that hydroxylate 6-dEB at C-6 or C-12 position.

In one embodiment, the invention provides a recombinant expression vector that comprises the desosamine biosynthetic genes and optionally a desosaminyl transferase gene. In a related embodiment, the invention provides recombinant host cells comprising the vector that produces the desosamine biosynthetic gene products and optionally a desosaminyl transferase gene product. In a preferred embodiment, the host cell is Streptomyces lividans or Streptomyces coelicolor. The desosaminyl transferase gene and gene product may be from the megalomicin gene cluster or may be from a different gene cluster, for example, the desosaminyl transferase gene and gene product from the pikromycin or narbomycin gene clusters as described in U.S. Pat. Nos. 6,509,455 and 6,303,767.

In one embodiment, the invention provides one or more recombinant expression vectors that comprise the desosamine and mycarose biosynthetic genes and, optionally, the desosaminyl and/or mycarosyl transferase genes. In a related embodiment, the invention provides recombinant host cells comprising the vector(s) that produces the desosamine and mycarosyl biosynthetic gene products and desosaminyl and mycarosyl transferase gene products. In a preferred embodiment, the host cell is S. lividans or S. coelicolor. As described above, the desosaminyl transferase gene and gene product and mycarosyl transferase gene and gene product may be from the megalomicin cluster or may be from a different gene cluster.

In one embodiment, the invention provides one or more recombinant expression vectors that comprise the desosamine, megosamine, and mycarose biosynthetic genes, and, optionally, a desosaminyl transferase, mycarosyl transferase, and/or megosamine transferase genes. In a related embodiment, the invention provides recombinant host cells comprising the vector(s) that produces the desosamine, megosamine and mycarosyl biosynthetic gene products and, optionally, desosaminyl, mycarosyl, and megosaminyl transferase gene products. In a preferred embodiment, the host cell is S. lividans or S. coelicolor. As described above, the desosaminyl transferase gene and gene product and mycarosyl transferase gene and gene product may be from the megalomicin cluster or may be from a different gene cluster.

In one aspect, the invention provides methods of producing a modified polyketide. In some embodiments, the method includes culturing a recombinant cell containing a nucleic acid of the invention under conditions in which the cell expresses a product of a gene encoded by the nucleic acid, and under conditions in which the unmodified polyketide is present, thereby producing the modified polyketide. In some of these embodiments the cell further contains a recombinant nucleic acid encoding at least one module of a polyketide synthase. In some embodiments, the cell produces megosamine and can attach megosamine to a polyketide, where the cell in its naturally occurring non-recombinant state cannot produce megosamine. In one embodiment, the invention provides a method for desosaminylating polyketide compounds in recombinant host cells, which method comprises expressing the PKS for the polyketide and a desosaminyl transferase and desosamine biosynthetic genes in said host cells. In one embodiment, the invention provides a method for desosaminylating and mycarosylating polyketide compounds in recombinant host cells, which method comprises expressing the PKS for the polyketide and a desosaminyl and mycarosyl transferase and desosamine and mycarose biosynthetic genes in said host cells. In one embodiment, the invention provides a method for mycarosylating desosaminylating, and megosaminylating polyketide compounds in recombinant host cells, which method comprises expressing the PKS for the polyketide and a desosaminyl, megosaminyl, and mycarosyl transferase and desosamine, megosamine, and mycarose biosynthetic genes in said host cells.

In one embodiment, the host cell expresses a beta-glucosidase gene as well, and this method may be advantageous when producing desosaminylated polyketides in Streptomyces or other host cells, that glucosylate desosaminylated polyketides, which can decrease antibiotic activity. By coexpression of beta-glucosidase, the glucose residue is removed from the polyketide.

In one embodiment, the invention provides the megK hydroxylase gene in recombinant form and methods for hydroxylating polyketides with the recombinant gene product. The invention also provides polyketides thus produced and the antibiotics or other useful compounds derived therefrom.

In one embodiment, the invention provides the megCIV 4,5-dehydratase, megCV reductase, megBVI 2,3-dehydratase (also known as megT) genes in recombinant form and methods for modifying polyketides with the recombinant gene product. The invention also provides polyketides thus produced and the antibiotics or other useful compounds derived therefrom.

The invention also provides novel polyketides or other useful compounds derived therefrom. The compounds of the invention can be used in the manufacture of another compound. In a preferred embodiment, the compounds of the invention are antibiotics formulated in a mixture or solution for administration to an animal or human.

These and other embodiments of the invention are described in more detail in the following description, the examples, and claims set forth below.

BRIEF DESCRIPTION OF THE DRAWINGS

FIG. 1 is a schematic of the megalomicin polyketide synthase (meg DEBS) and corresponding meg genes upstream and downstream of the meg DEBS region and cosmids overlapping this region.

FIG. 2 is a schematic of the megalomicin biosynthetic pathway.

FIG. 3 is a schematic of the biosynthetic pathways of the deoxysugars megosamine, mycarose, and desosamine in megalomicin synthesis.

DETAILED DESCRIPTION OF THE INVENTION (1) Introduction

The present invention provides novel genes of the megalomicin cluster in isolated, purified, and/or recombinant form, including genes of the mycarosyl biosynthesis pathway and transferase, desosamine biosynthesis pathway and transferase, megosamine biosynthesis pathway and transferase, the megM and megL genes common to deoxysugar synthesis, as well as the monooxygenases of P450 type MegK and MegF.

The present invention provides in isolated, purified, and/or recombinant form desosamine biosynthesis genes megCII, megCIV, megCV, megDII, megDIII, and the megCIII transferase gene, as well as the proteins encoded by those genes.

The present invention provides in recombinant form mycarose biosynthesis genes megBIV, megBII (megBII-2), megBIII, megBVI, megDIV, and the megBV transferase gene, as well as the proteins encoded by those genes.

The present invention provides in isolated, purified, and/or recombinant form megosamine biosynthesis genes megDII, megDIII, megDIV, megDV, megDVII, megDVI, megBVI (megT), and the megDI transferase gene, as well as the proteins encoded by those genes.

The present invention provides isolated, purified, and/or recombinant P450-like monooxygenase enzymes MegK and MegF, and the genes megK and megF in recombinant form.

The present invention provides isolated, purified, and/or recombinant deoxysugar genes megM encoding a meg glucose-6-dehydratase, and megL encoding a meg TDP-glucose synthase.

The present invention provides isolated, purified, and/or recombinant megalomicin cluster PKS regulatory gene megR and its control binding sequences, and protein encoded by its coding sequence.

The present invention further provides vectors containing the genes of the invention, as well as host cells containing the genes of the invention. The invention also provides methods of producing modified polyketides by culturing recombinant cells that contain the genes of the invention under conditions where one or more of the genes are expressed and the unmodified polyketide is present; in some cases the cell further contains a recombinant nucleic acid encoding at least one module of a polyketide synthase.

The invention further provides polyketides produced using the above nucleic acids and methods.

(2) Definitions

The present invention may be better understood with reference to the following definitions. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As used herein, 'nucleic acid' and 'polynucleotide' have their ordinary meanings and are used interchangeably. It will be appreciated that reference to one strand of a double-stranded molecule is intended to refer as well to the complementary strand, the sequence of which will be apparent to the practitioner. Exemplary nucleic acids are RNA and DNA; the latter is also referred to herein as 'DNA compounds.'

As used herein, 'recombinant' has its ordinary meaning in the art and refers to a nucleic acid synthesized or otherwise manipulated in vitro (e.g., 'recombinant nucleic acid'), to methods of using recombinant nucleic acids to produce gene products in cells or other biological systems, to a polypeptide (e.g., 'recombinant protein') encoded by a recombinant nucleic acids, or to cells comprising a recombinant nucleic acid (including progeny of cells into which a recombinant nucleic acid has been introduced).

As used herein, 'gene' refers to a nucleic acid sequence that encodes a useful product. A gene can encode an mRNA that is transcribed from the gene and translated by a ribosome into a protein. 'Extra copies' of a gene, e.g., 'extra copies of an eryG gene,' refers to a gene that is introduced into a cell that already contains a copy of the gene.

As used herein, 'polyketide modifying gene' or 'polyketide synthase (PKS) modifying gene' (used interchangeably herein) refers to a gene encoding a protein that effectuates glycosylation of an aglycone, including the biosynthesis of the glycosyl unit or sugar, or hydroxylation of an aglycone, to produce a 'modified polyketide,' i.e., a polyketide that has been modified from an aglycone and/or that has been modified by the addition of hydroxyls beyond those present in the polyketide as synthesized by the PKS core enzymes. Non-limiting examples of polyketide modifying genes and the proteins encoded by them are the megF gene (encoding a C-6 hydroxylase), the megK gene (encoding a C-12 hydroxylase); megDI, megDII, megDIII, megDIV, megDV, megDVI, megDVII, and megBVI genes (encoding enzymes of the megosamine biosynthetic pathway); megCII, megCIV, megCV, and megCIII (encoding enzymes of the desosamine biosynthetic pathway); and megBII (megBII-2), megBIII, megBIV, megBV, and megBVI (encoding enzymes of the mycarose biosynthetic pathway; megR (encoding a regulatory gene); megL (encoding a TDP-glucose synthase gene), and megM (encoding a hexose dehydratase). These are merely examples; other polyketide modifying genes are apparent from context and are described below. Enzymes and other regulatory proteins encoded by polyketide modifying genes are referred to herein as "polyketide modifying enzymes."

As used herein, 'heterologous' in reference to a polyketide modifying gene or protein in a recombinantly modified cell means a gene or protein not found in an unmodified cell of the same species or strain (e.g., a non-recombinant cell). One example of a heterologous gene is a gene from a first species that is introduced into a cell of a second species (e.g., by introduction of a recombinant polynucleotide encoding the gene). Another example of a heterologous gene is a gene (in a cell) that encodes a chimeric PKS.

As used herein, a promoter operably linked to a protein encoding sequence (gene) is 'heterologous' if it is not usually associated with the gene. In one embodiment a heterologous promoter is derived from a different species than the protein encoding sequence (for example a viral promoter that controls expression a bacterial gene). In another embodiment, a heterologous promoter is from the same species but is not normally (i.e., in non-recombinant organisms) associated with the gene. A heterologous promoter may also be a synthetic promoter.

As used herein, 'host cell' refers to a prokaryotic or eukaryotic cell that can or has received recombinant vectors bearing one or more PKS genes, or a complete PKS cluster, and/or a polyketide modifying gene. The term includes progeny of the host cell.

An 'aglycone,' as used herein, refers to the product of a PKS enzyme that has not been modified by the addition of a sugar moiety and/or alteration by a P450 monooxygenase.

A 'control sequence' is a sequence operably linked to a gene that is capable of effecting the expression of the gene. The 'control sequence' need not be contiguous with the gene, so long as it functions to direct the expression of the gene.

As used herein, 'operably linked,' 'operatively linked' or 'operationally associated' (used interchangeably) refer to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. To optimize expression and/or in vitro transcription, it may be helpful to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867-19870 (1991)) can be inserted immediately 5' of the start codon and may enhance expression. The desirability of (or need for) such modification may be empirically determined using techniques known in the art.

A 'megosamine biosynthetic gene set' is a gene or set of genes that confers to a heterologous host that does not produce megosamine, the ability to synthesize megosamine and, optionally, to transfer it to an aglycone. Non-limiting examples of genes belonging to a megosamine biosynthetic gene set include megDI, megDII, megDIII, megDIV, megDV, megDVI, megDVII, and megBVI.

A 'desosamine biosynthetic gene set' is a gene or set of genes that confers to a heterologous host that does not produce desosamine, the ability to synthesize desosamine and, optionally, to transfer it to an aglycone. Non-limiting examples of genes belonging to a desosamine biosynthetic gene set include megCII, megCIV, megCV, megCIII, megDII, and megDIII.

A 'mycarose biosynthetic gene set' is a gene or set of genes that confers to a heterologous host that does not produce mycarose, the ability to synthesize mycarose and, optionally to transfer it to the appropriate attachment point on an aglycone. Non-limiting examples of genes belonging to a mycarose biosynthetic gene set include megBII (megBII-2), megBIII, megBIV, megBV, and megBVI, and megDIV.

A 'modifying gene analog' is a first gene that is derived from a different organism from a second gene that performs the same function as the second gene. For example, the megK gene of the present invention derived from *M. megalomicea*, sp. *nigra*, the product of which hydroxylates the C-12 position of the aglycone, has a modifying gene analog eryK derived from *S. erythraea*.

The present invention may be practiced with reference to this disclosure and conventional methods of molecular biology and recombinant DNA techniques within the skill of one of ordinary skill in the art. Such techniques are explained in the literature, see e.g. *Current Protocols in Molecular Biology* (F. M. Ausubel et al., eds., 1987, including supplements through 2001); *Molecular Cloning: A Laboratory Manual*, third edition (Sambrook and Russel, 2001); *PCR: The Polymerase Chain Reaction*, (Mullis et al., eds., 1994); *Current Protocols in Immunology* (J. E. Coligan et al., eds., 1999, including supplements through 2001).

(3) Description

The invention provides nucleic acids that contain polyketide modifying genes. The invention also provides vectors and host cells containing the nucleic acids, methods of using the host cells to produce glycosylated polyketides, and the glycosylated polyketides so produced.

Nucleic acids: A total genomic DNA library of *Micromonospora megalomicea*, sp. *nigra*, was made and cloned into cosmids, essentially as previously reported (Volchegursky, et al., 2000) A series of four overlapping inserts containing the meg cluster were isolated from the cosmid library prepared from total genomic DNA of *M. megalomicea* that covered >100 kb of the genome. A contiguous 48 kb segment that encodes the megalomicin PKS and several deoxysugar biosynthetic genes was sequenced and analyzed (see FIG. 1). The sequence data for the genes contained in this 48 kb segment has been submitted to the DDBJ/EMBL/GenBank database under the accession number AF263245, incorporated herein by reference. The four cosmids containing the overlapping inserts were designated pKOS079-138B, pKOS079-93A, pKOS079-93D, and pKOS205.57-2.3B. Cosmid pKOS079-93A was deposited with the American Type Culture Collection (ATCC, 10801 University Blvd., Manassas, Va.), on Oct. 3, 2002 in accordance with the terms of the Budapest Treaty and is available under accession number PTA-2555. Cosmids pKOS079-138B and pKOS205.57-2.3B were deposited with the ATCC on May 20, 2003 in accordance with the terms of the Budapest Treaty and are available under accession numbers PTA-5210 and PTA-5211, respectively. The sequences of the inserts of cosmids p pKOS079-138B and pKOS205.57-2.3B are given as SEQ ID NO: 1 and SEQ ID NO: 2, respectively. SEQ ID NO: 1 differs from a preliminary sequence of the upstream megalomicin modification genes ("preliminary sequence 1") in that preliminary sequence 1 contained a cytosine rather than an adenosine at position 59, and a cytosine rather than a thymidine at position 171, and nucleotides 5797-5799 (GGA) of SEQ ID NO:1 were deleted from preliminary sequence 1. References herein to a nucleic acid comprising SEQ ID NO: 1 or portions thereof are also intended to refer to preliminary sequence 1. References herein to genes and/or ORFs that are described in terms of SEQ ID NO: 1 are also intended to refer to the corresponding genes and/or ORFs of preliminary sequence 1, taking into account the above nucleotide substitutions and deletion.

The ORFs megAI, megAII, and megAIII encode the polyketide synthase responsible for synthesis of 6-dEB. The enzyme complex meg DEBS is similar to ery DEBS, with each of the three predicted polypeptides sharing an average of 83% overall similarity with its ery PKS gene analog. Both PKSs are composed of six modules (two extender modules per polypeptide) and each module is organized in an identical manner. The megosanine biosynthetic genes are clustered upstream of the meg DEBS genes, while sugar modifying genes are clustered in the downstream region.

The boundaries of the ORFs of the genes of the present invention are listed in Table 1 below.

TABLE 1

Open Reading Frame Boundaries

| Open Reading Frame | Codon Boundaries |
|---|---|
| SEQ ID NO. 1 (upstream) | |
| megR | 52-942 |
| megK | 1051-2244 |
| megCV | Complement 2386-3855 |
| megCIV | Complement 3893-5098 |
| megBVI | Complement 5095-6558 |
| megDVI | 7342-8475 |
| megDI | 8486-9024 |
| SEQ ID NO. 2 (downstream) | |
| megAIII (partial) | 1-6965 |
| megCII | 6962-8038 |
| megCIII | 8049-9317 |
| megBII-2 | 9314-10285 |
| megH | Complement 10354-11097 |
| megF | Complement 11105-12316 |
| megBIII | Complement 12316-13548 |
| megM | Complement 13928-14911 |
| megL | Complement 14908-15972 |
| ORF1 | Complement 16326-17463 |

The nucleic acids of the invention may be provided in isolated (i.e., not pure, but existing in a preparation in an abundance and/or concentration not found in nature), purified (i.e., substantially free of contaminating materials or substantially free of materials with which the corresponding DNA would be found in nature), and/or recombinant (i.e., nucleic acid synthesized or otherwise manipulated in vitro) form. Portions of nucleic acids of the invention (e.g., DNA molecules) that encode polyketide modifying enzymes (as distinguished from, e.g., vector sequences) may, in some embodiments, be fewer than about 15, 12, 10, 9, 8, 7, 6, or 5 kilobases in length. In one embodiment the portion of the nucleic acid is fewer than about 9 kilobases in length. The DNA molecules of the invention may in some embodiments also comprise one or more sequences that, in addition to polyketide modifying genes, encode one or more domains of a polyketide synthase, which may be a naturally-occurring or modified polyketide synthase. For example, the DNA molecules of the invention may in some embodiments encode one or more domains (or fragments of such domains) of one or more modules in one or more of the ORFs of the megalomicin or other PKS. Examples of PKS domains include the KS (beta-ketoacylsynthase), acyltransferase (AT), dehydratase (DH), ketoreductase (KR), enoylreductase (ER), acyl carrier protein (ACP), and thioesterase (TE) of at least 6 extender modules and loading module of the three proteins encoded by the three ORFs of the megalomicin PKS gene cluster.

In one aspect, a nucleic acid sequence of the invention that encodes a polyketide modifying enzyme (e.g., MegR, MegF, MegK, MegCIV, MegCV, MegBVI, MegBIII, MegL, and MegM proteins) hybridizes under stringent conditions to SEQ ID NO: 1 or 2. Typically, the nucleic acid sequence possesses at least about 90% sequence identity with a portion of SEQ ID NO: 1 or 2 that encodes a polyketide modifying enzyme. In one aspect the polyketide modifying enzyme is encoded by SEQ ID NO: 1 or 2 or a sequence that differs from the enzyme-encoding region of SEQ ID NO: 1 or 2 due to the degeneracy of the genetic code. In similar fashion, a polypeptide can typically tolerate one or more amino acid substitutions, deletions, and insertions in its amino acid sequence without loss or significant loss of desired activity. The present invention includes such polypeptides with alternate amino acid sequences, and the nucleic acid sequences that encode them; the nucleic acid sequences and amino acid sequences encoded by the nucleic acid sequences shown herein merely illustrate preferred embodiments of the invention. The activities for the polyketide modifying enzymes are described herein.

In relation to polynucleotides and polypeptides, the term substantially identical or homologous or similar varies with the context as understood by those skilled in the relevant art and generally means at least 70%, preferably means at least 80%, more preferably at least 90%, more preferably at least 93%, more preferably at least 95% identity, more preferably at least 96% identity, sometimes at least 97% identity or even at least about 98% identity. To determine identity, optimal alignment of sequences for comparison can be-conducted, e.g., by the local homology algorithm of Smith & Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group, 575 Science Dr., Madison, Wis. The BLAST algorithm (Altschul et al., 1990, Mol. Biol. 215:403-10) for which software may be obtained through the National Center for Biotechnology Information, see BLAST (a service of the National Center for Biotechnology Information, U.S. National Library of Medicine, 8600 Rockville Pike, Bethesda, Md. 20894) [online] program selection revised Apr. 25, 2002 [retrieved on Jun. 26, 2003]. The BLAST program available at www.ncbi.nlm.nih.gov/BLAST/ can also be used. When using any of the aforementioned algorithms, the default parameters for "Window" length, gap penalty, etc., are used.

As used herein: stringency of hybridization is as follows: (1) high stringency: 0.1×SSPE (180 mM NaCl and 10 mM $NaH_2PO_4$, pH 8.3), 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures. Homologs (e.g., nucleic acids of the above-listed genes of species other than *Micromonospora megalomicea*) or other related sequences (e.g., paralogs) can be obtained by, for example, low, moderate or high stringency hybridization with all or a portion of the particular sequence provided as a probe using methods well known in the art for nucleic acid hybridization and cloning.

The invention provides isolated, purified, or recombinant nucleic acids that contain at least one polyketide modifying gene, where the gene encodes a polyketide modifying enzyme. In some embodiments, the polyketide modifying enzyme encoded by the gene is MegR, MegF, MegK, MegCIV, MegCV, MegBVI, MegBIII, MegL, or MegM. In some embodiments, the polyketide modifying enzyme is MegR, MegK, MegCIV, MegCV, or MegBVI. In some embodiments, the polyketide modifying enzyme is MegF, MegBIII, MegL, or MegM. The gene may be operably linked to a promoter, which in some cases is a heterologous promoter. In some embodiments, the nucleic acid does not contain one or more of megBI, megBV, megBIV, megCI, megCII, megDII, megDIII, megDIV, megDV, megDVII, or megY. In some embodiment, the polyketide modifying gene encodes an amino acid sequence that is encoded by a portion of SEQ ID NO: 1 or SEQ ID NO: 2.

The invention also provides an isolated, purified, or recombinant polyketide modifying enzyme gene megK, megCV, megCIV, megR, megBVI, megF, megBIII, megL, or megM.

Vectors: The nucleic acids of the invention may be inserted into a vector containing additional sequences that assist in cloning, amplification and splicing of nucleotide sequences, and/or sequences that facilitate introduction into the cell and/or determine the relative stability and final location of the introduced nucleic acid (i.e., integrated or episomal). As used herein, the term "vector" refers to a polynucleotide construct designed for transduction/transfection of one or more cell types. Vectors may be, for example, "cloning vectors," which are designed for isolation, propagation and replication of inserted nucleotides, which may be useful for, e.g., isolating and sequencing areas of a genome of interest. An illustrative example is a cosmid vector. Vectors may also be "expression vectors," which are designed for expression of a nucleotide sequence in a host cell. Generally, the expression vector further comprises an origin of replication or a segment of DNA that enables chromosomal integration. Expression vectors may further comprise termination sequences, polyadenylation sequences, and the like, as are well-known in the art. Generally vectors are suitable for introduction into prokaryotic cells, or introduction into eukaryotic cells. Shuttle vectors are used for introduction into both eukaryotic and prokaryotic cells.

A vector used in the invention may be any vector that is compatible with the cell into which it is introduced. Conventional recombinant DNA and RNA techniques, such as those described in Sambrook, supra, may be used to construct vectors containing inserts that contain nucleic acids of the invention.

In some embodiments, the invention provides a cosmid vector that is pKOS079-138B or pKOS205.57-2.3B. In some embodiments, the cosmid vector contains one or more genes having a sequence shown in SEQ ID NO: 1 or SEQ ID NO: 2; in some embodiments, the vector contains one or more genes having a sequence that is substantially identical (e.g., possessing at least 70%, 80%, 90%, 93%, 95%, 96%, 97%, or 98% identity) to SEQ ID NO: 1 or SEQ ID NO: 2; in some embodiments, the vector contains one or more genes having a sequence that hybridizes to SEQ ID NO: 1 or SEQ ID NO: 2 under stringent conditions.

The invention also provides expression vectors that contain at least one of the polyketide modifying genes described above, where the gene is operably linked to a promoter. In one embodiment, the invention provides a recombinant expression vector that comprises the desosamine biosynthetic genes, and optionally a desosaminyl transferase gene. In one embodiment, the invention provides one or more recombinant expression vectors that comprise the desosamine and mycarose biosynthetic genes, and optionally desosaminyl and mycarosyl transferase genes. In one embodiment, the invention provides one or more recombinant expression vectors that comprise the desosamine, megosamine, and mycarose biosynthetic genes, and, optionally, desosaminyl, and mycarosyl transferase genes. In some embodiments, the polyketide modifying gene is megR, megF, megK, megCIV, megCV, megBVI, megBIII, megL, or megM.

Host cells: The invention further provides host cells that contain the vectors and nucleic acids of the invention. Any means, physical or biological, may be used in the methods of the present invention to introduce the nucleic acids (usually as part of a larger vector) into a cell. Means of in vitro introduction of foreign nucleic acid into a cell are well-known in the art, and include standard methods of transformation, transfection, and the like, including calcium phosphate precipitation, electroporation, lipofection, direct injection, DEAE-dextran, and the like (see, for example, Kriegler, *Gene Transfer and Expression: A Laboratory Manual* (1990) Stockton Press, New York, N.Y.).

The host cells of the present invention may be producers of 6-deoxysugars or may be host cells that do not naturally contain PKS genes or PKS modifying genes. The host cells of the present invention may also be natural producers of polyketides having genes for the synthesis and transfer of some deoxy sugars, for example, mycarose, but not desosamine or megosamine. In this latter case, the genes of the present invention, when introduced into said host cell confer upon the host cell the ability to synthesize one or more of the deoxysugars it lacks, for example desosamine or megosamine. Exemplary host cells of the invention include *Streptomyces coelicolor*, *Streptomyces lividans*, and *Micromonospora megalomicea*.

The invention provides host cells, e.g., *Streptomyces coelicolor* or *Streptomyces lividans*, that express the products the MegF and/or MegK hydroxylase genes, the megosamine biosynthesis and transfer genes of the present invention, the desosamine biosynthesis and transfer genes of the present invention, the mycarose biosynthesis and transfer genes of the present invention, and/or MegM and MegL. Thus, in some embodiments, the host cell expresses a P450-type monooxygenase enzyme, which in some cases is heterologous, and which in some cases is MegK or MegF. In some embodiments, the host cell expresses a gene from a desosamine biosynthetic gene set, where the gene is megCIV, megCV, or megCIII; in some embodiments, the gene is megCII, megCIV, megCV, or megCIII. In some embodiments, the host cell expresses a gene from a megosamine biosynthetic gene set, where the gene is megBVI or megDI; in some embodiments the gene is megDI, megDII, megDIII, megDIV, megDV, megDVI, megDVII, or megBVI. In some embodiments, the host cell expresses a gene from a mycarose biosynthetic gene set, where the gene is megBIII or megBVI; in some embodiments, the gene is megBII (meg BII-2), megBIII, megBIV, megBV, or megBVI. In some embodiments, the host cell contains an isolated, purified, or recombinant nucleic acid that encodes a polyketide modifying enzyme MegR, MegF, MegK, MegCIV, MegCV, MegBVI, MegBIII, MegL, or MegM enzymes, and expresses one or more of these enzymes. In some embodiments, the host cell contains an isolated, purified, or recombinant nucleic acid containing genes for the biosynthesis and attachment of mycarose to a polyketide and/or hydroxylation of the polyketide, where the genes include the genes that encode the enzymes MegM, MegL, MegBIII, MegBIV, MegDIV, MEG BII (MegBII-2), MegBVI, optionally MegBV, and, optionally, MegF, and expresses one or more of these enzymes. In some embodiments, the host cell contains an isolated, purified, or recombinant nucleic acid containing genes for the biosynthesis and attachment of megosamine to a polyketide, where the genes may include the genes that encode the enzymes MegM, MegL, MegCII, MegBVI, MegDIV, MegDV, MegDII, and MegDIII enzymes, and, optionally the MegDI enzyme, and expresses one or more of these enzymes. In some embodiments, the host cell contains an isolated, purified, or recombinant nucleic acid containing genes for the biosynthesis and attachment of megosamine to a polyketide, where the genes may include the genes that encode the enzymes MegM, MegL, MegCII, MegBVI, MegDIV, MegDVI, MegDVII, MegDII, and MegDIII enzymes, and, optionally the MegDI enzyme, and expresses one or more of these enzymes. In some embodiments, the host cell contains an isolated, purified, or recombinant nucleic acid containing genes for the biosynthesis and attachment of desosamine to a polyketide, where the genes include the genes that encode the enzymes MegM, MegL, MegCII, MegCIV, MegCV, MegDII, and MegDIII enzymes, and, optionally, the MegCIII enzyme, and expresses one or more of these enzymes.

Illustrative host cells of the present invention include *Streptomyces coelicolor* and *Streptomyces lividans* cells into which the vectors of the present invention have been introduced. The invention provides, for example, an *S. coelicolor* host cell, transformed to produce the MegF and MegK hydroxylases, the mycarose biosynthesis and transfer genes of the present invention, and/or the desosamine biosynthesis and transfer genes of a different species, e.g., *S. erythraea*. These host cells illustrate how one can use certain recombinant genes of the present invention with modifying gene analogs to create host cells of the invention.

Another illustrative host cell of the present invention is an *E. coli* host cell transformed with vectors having the megAI, megAII, and megAIII PKS genes to make 6-dEB; the genes for MegM glucose-6-dehydrogenase and MegL TDP-glucose-synthase to make deoxysugars; the genes for MegF and MegK P450-type monooxygenases to hydroxylate the 6-dEB aglycone at the C-6 and C-12 positions respectively; the mycarose biosynthesis and transferase genes; and the desosamine biosynthesis and transferase genes. In another embodiment, the host cell further comprises the megosamine biosynthesis and transferase genes.

Methods and compounds: The invention also provides methods for producing hydroxylated and glycosylated polyketides using the nucleic acids, vectors, and host cells described herein, by culturing a host cell that contains an expression vector of the invention under conditions where the cell produces a polyketide that is then modified. The cell may be unable to make the polyketide in the absence of the expression vector. For example, in some embodiments, the cell in its natural, non-recombinant state is unable to produce 6 dEB. Methods of culturing host cells, such as those provided by the invention, to produce a polyketide are known in the art.

In an illustrative embodiment, the polyketide is a derivative of 6-dEB that has a group other than an ethyl moiety at C-13 (13-R-6-dEB, where R is not ethyl). Methods for making 13-R-6-dEB compounds in an *S. coelicolor* host cell, which lacks genes for polyketide modification enzymes, are described in U.S. Pat. Nos. 6,080,555; 6,274,560; 6,066,271; and 6,261,816, as well as PCT Pub. Nos. 98/49315; 99/03986; and 00/44717. These 13-R-6-dEB compounds can be converted to the corresponding 13-R-erythromycins by feeding the aglycones to a fermentation of *S. erythraea*, as described in the aforementioned patent publications. The 13-R-erythromycins can be converted chemically into potent antibiotics known as ketolides, as described in PCT Pub. Nos. 00/63225; 00/62873; and 00/63224, each of which is incorporated herein by reference. The present invention provides methods and reagents for making the 13-R-erythromycins in a single fermentation, as opposed to two fermentations, in that the invention provides a host cell that contains the requisite hydroxylase genes and desosamine and mycarose biosynthesis and transferase genes from the megalomicin biosynthetic gene cluster as well as the PKS for making the 13-R-erythromycins. The PKS genes and the corresponding mutated versions (which contain the KS1 null mutation) that produce a PKS that can convert a diketide into a 13-R-6-dEB can be obtained as described in PCT Pub. No. 01/27284 (the meg PKS genes); U.S. Pat. No. 6,251,636 (the ole PKS genes); and U.S. Pat. No. 6,080,555 (the ery PKS genes), each of which is incorporated herein by reference. This host cell of the invention produces 13-R-erythromycin C compounds, instead of 13-R-erythromycin A compounds, because the host cell lacks the eryG gene that converts the mycarosyl residue to a cladinosyl residue. In other embodiments, the host cell is provided with a recombinant eryG gene and makes the corresponding 13-R-erythromycin A derivatives. In another embodiment, the host cell contains PKS genes that do not comprise the KS1 null mutation and so produce erythromycins A, B, C, and/or D. Thus, the host cells of the invention can be used to produce erythromycin and erythromycin analogs that can be converted to ketolides.

In one embodiment, the invention provides *Streptomyces lividans* and *Streptomyces coelicolor* host cells transformed with a vector or vectors including the PKS genes (megAI, megAII, and megAIII), and the genes for hydroxylation and for production and transfer of glycosyl units, as shown in FIGS. 2 and 3: mycarose genes (eryG, megL, megM, megDIV, and all megB genes), desosamine genes (megL, megM, megDII and megDIII, and all megC genes), megosamine genes (megL, megM, megBVI, and all megD genes), and megK and megF genes and the transformed host is cultured under conditions that lead to the production of polyketides resulted in the production of novel biologically active compounds, such as the compound of formula (1) having a methyl group in the 3'" position of the mycarose sugar moiety of megalomicin. This compound is believed to be a more potent antibiotic against certain pathogens than megalomicin.

Formula 1

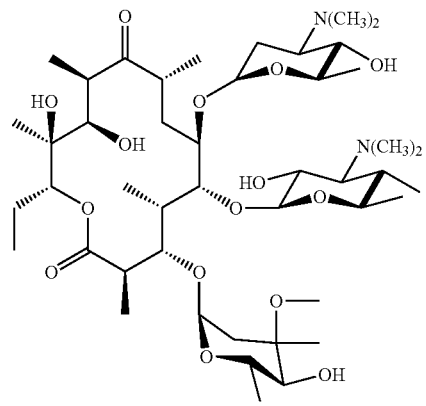

6-O-Megosaminylerythromycin A
3'''-O-Methylmegalomicin A

In another embodiment, the invention provides a method for making a polyketide of formula (1) as follows. A vector including a functional eryG gene and a disrupted megG (previously designated megY) gene is transformed into an *M. megalomicea* host and the transformed host cultured under conditions such that polyketides are produced. This results in the production of the compound of formula (1) having a methyl group in the 3'" position of the mycarose sugar moiety of megalomicin.

The invention also provides a method of producing the polyketide of Formula (1) by culturing a cell that expresses one or more polypeptides encoded by a recombinant polynucleotide that includes the genes megDII, DIII, DIV, DV, DVI, and DVII, and optionally includes extra copies of an eryG gene, and does not include a megY gene, where the cell produces erythromycin A in the absence of the recombinant polynucleotide, under conditions where the cell produces the polyketide.

The invention further provides a method of producing the polyketide of Formula (1) by culturing a cell that is a *Streptomyces coelicolor* or a *S. lividans* cell, where the cell expresses one or more polypeptides encoded by a recombinant polynucleotide that includes the genes megAI, megAII, and megAIII; mycarose genes that include all megB genes and the megAIII gene; desosamine genes that include all megC genes and the megDII and megDIII genes; megosamine genes that include all megD genes; eryG, megL, megM and megK and megF; under conditions where the cell produces the polyketide.

The invention further provides a method of producing the polyketide of Formula (1) by culturing a *Micromonospora megalomicea* cell that contains a recombinant polynucleotide that includes an eryG gene under control of a regulator or promoter, where the megY gene of the host cell is disrupted or its product is inactivated, under conditions where the cell produces the polyketide.

The invention further provides a method for producing 3-O-α-mycarosyl-erythronolide B in heterologous host (see, e.g., Example 7) by introducing an isolated, purified, or recombinant nucleic acid containing genes for the biosynthesis and attachment of mycarose to a polyketide, where the genes include the genes that encode the enzymes MegM, MegL, MegBIII, MegBIV, MegDIV, Meg BV, Meg BII (MegBII-2), Meg BVI, and, optionally, MegF, into a heterologous host cell, e.g., *S. coelicolor*, and culturing the cells under conditions where the 3-O-α-Mycarosyl-Erythronolide B is produced. Such conditions in *S. coelicolor* are, for example, YEME medium with thiostreptin, fed with 6-deoxyerythronolide B (see Example 7).

The invention further provides the polyketide of Formula (1). In some embodiments, the polyketide is isolated and/or purified. Methods for isolation and purification of polyketides are known in the art.

Thus the recombinant genes of the invention, and the portions thereof, are useful for a variety of purposes, including production of novel megalomicin analogs. BLAST (Altschul et al., 1990) analysis of the genes flanking the meg PKS genes indicates that 13 complete open reading frame (ORFs) appear to encode functions required for synthesis of at least one of the three megalomicin deoxysugars. Each ORF was assigned to a specific deoxysugar pathway based on comparison to PKS genes and other related genes involved in deoxysugar biosynthesis. Three ORFs, megB V, megCIII and megDI, encode glycosyl-transferases, one for attachment of each different deoxysugar to the macrolide. MegBV was assigned to the mycarose pathway in the meg cluster. In similar fashion, assignments were made accordingly for: MegCII and MegDVI, two 3,4-isomerases homologous to EryCII; MegBII (MegBII-2) and MegDVII (MegBII-1), 2,3-reductases homologous to EryBII; MegBIV and MegDV, putative 4-ketoreductases similar to EryBIV. The remaining ORFs involved in deoxysugar biosynthesis, megBVI (also known as megT), megDII, megDIII and megDIV, each encode a 2,3-dehydratase, aminotransferase, dimethyltransferase and 3,5-epimerase respectively. As both the megosamine and desosamine pathways require an aminotransferase and a dimethyltransferase, and as mycarose and megosamine each require a 2,3-dehydratase and a 3,5-epimerase, assignments of these four genes to a specific pathway could not be made on the basis of sequence comparison alone.

Additional complete ORFs megG (also designated megY), megH, megK and megF were also identified in the cluster with sequence to the encoded proteins MegH, MegK, and MegF. The proteins MegH, MegK and MegF share high degrees of similarity with EryH, EryF, and EryK respectively.

EryH and homologues in other macrolide gene clusters are thioesterase-like proteins (Haydock et al., 1991; Xue et al., 1998; Butler et al., 1999; Tang et al., 1999). This gene can be inserted in a heterologous host or disrupted in the native host to increase production of a desired polyketide. The eryF gene encodes the erythronolide B C-6 hydroxylase (FIG. 2) (Weber et al., 1991; Andersen and Hutchinson, 1992). The eryK gene encodes erythromycin D C-12 hydroxylase. The megY gene does not have an ery counterpart, but is believed to belong to a (small) family of O-acyltransferases that transfer short acyl chains to macrolides (Hara, O., et al. 1992). The structures of various megalomicins places megY in the latter class as the acyltransferase that converts megalomicin A to megalomicins B, C1 or C2.

An examination of the meg cluster reveals that the megosamine biosynthetic genes are clustered directly upstream of the PKS genes. The hypothesis that these genes are sufficient for biosynthesis and attachment of megosamine to a macrolide intermediate was confirmed by functional expression of these genes in a strain which produces erythromycin, such as *S. erythraea*, resulting in production of megalomicin (See Example 3). Expression of megDVI-megDVII segment in *S. erythraea* and the corresponding production of megalomicins in this host established the likely order of sugar attachment in megalomicin synthesis (See FIG. 2). Furthermore, it has provided a means to produce megalomicin in a more genetically friendly host organism, leading to the creation of megalomicin analogues by manipulating the megalomicin PKS.

Because introduction of this meg DNA segment into *S. erythraea* results in production of megalomicins, it is clear that these genes encode the functions for TDP-megosamine biosynthesis and transfer to its substrate and to acylate the polyketide (see FIG. 2). The remaining region upstream of megDVI includes genes for mycarose and desosamine biosynthesis. Furthermore, if the organization resembles that of the left arm of the ery cluster, the megosamine biosynthesis 'island' may have been formed via an insertion of the megD and megY genes into an existing erythromycin or other common ancestral gene cluster.

The entire gene set from megDI to megDVII was introduced in *S. erythraea* to produce TDP-megosamine. Two alternative pathways are possible. One pathway converts TDP-2,6-dideoxy-3,4-diketo-hexose (or its enol tautomer), the last intermediate common to the mycarose and megosamine pathways, to TDP-megosamine through the sequence of 5-epimerization, 4-ketoreduction, 3-amination and 3-N-dimethylation using the genes megDIV, megDV, megDII and megDIII (FIG. 3). This pathway uses the same functions proposed for biosynthesis of TDP-daunosamine by Olano et al. (1999) but in a different sequential order. However, it does not account for the megDVI and megDVII genes as their encoded activities are not required in this pathway. A parallel pathway that uses these genes is also shown in FIG. 3. In this alternative route, 2,3-reduction and 3,4-tautomerization are performed by the megDVII and megDVI gene products, respectively. To confirm which alternative pathway is utilized in a host cell, gene disruption and complementation experiments can be conducted.

The 48 kb segment sequenced also contains genes required for synthesis of TDP-L-mycarose and TDP-D-desosamine (FIG. 3). The megCII gene encodes a putative 3,4-isomerase which catalyses the presumed first step in the committed TDP-desosamine pathway. The start codon of megCII overlaps the stop codon of megAIII in exactly the same manner as their erythromycin counterparts eryCII and eryAIII overlap (Summers et al., 1997), suggesting that these genes are translationally coupled in both systems. The high degree of similarity between MegCII and EryCII indicates that the pathway to desosamine in the megalomicin-producing and erythromycin-producing organisms is similar. Similarly, the finding that megBII (megBII-2) and megBIV, encoding a 2,3-reductase and 4-ketoreductase, contain close homologues in the mycarose pathway for erythromycin also suggests that TDP-L-mycarose synthesis in the two host organisms is the similar.

Of note are the two genes that encode putative 2,3-reductases megBII (meg BII-2) and megDVII (megBII-1). Because MegBII (MegBII-2) most closely resembles EryBII, a known mycarose biosynthetic enzyme (Weber et al., 1990), and because megBII resides in the same location of the meg cluster as its counterpart in the ery cluster, megBII (megBII-2) was assigned to the mycarose pathway and megDVII (megBII-1) to the megosamine pathway. Furthermore, the lower degree of similarity between MegDVII (megBII-1) and either EryBII or MegBII (megBII-2) (Table 1) provided a basis for assigning the opposite L- and D-isomeric substrates to each of the enzymes (FIG. 3). Finally, megBVI, which encodes a putative 2,3-dehydratase, is also related to eryBVI gene in the ery mycarose pathway. In S. erythraea, the proposed intermediate generated by EryBVI represents the first committed step in the biosynthesis of mycarose (FIG. 3). However, the proposed pathways in FIG. 3 suggest that this may be an intermediate common to both mycarose and megosamine biosynthesis in M. megalomicea.

The recombinant genes, vectors, and host cells of the invention have a wide variety of useful applications. Host-vector systems for expression of meg DEBS genes and other heterologous expression of modular PKS genes for erythromycin (Kao et al., 1994b; Ziermann and Betlach, 1999), picromycin (Tang et al., 1999) and oleandomycin (Shah et al., 2000) as well as for the generation of novel polyketide backbones in which domains have been removed, added or exchanged in various combinations (McDaniel et al., 1999) have been described. Hybrid polyketides have been generated through the co-expression of subunits from different PKS systems (Tang et al., 2000). The present invention provides materials and methods of producing modified polyketides in heterologous hosts by the addition, replacement, or removal of modifying sugar moieties and/or hydroxyl groups on the polyketide core.

A detailed description of the invention having been provided, the following examples are given for the purpose of illustrating the invention and shall not be construed as being a limitation on the scope of the invention or claims.

EXAMPLE 1

Materials and Methods

Strains. Routine DNA manipulations were performed in Escherichia coli XL1 Blue or E. coli XLI Blue MR (Stratagene) using standard culture conditions (Sambrook et al., 1989). M. megalomicea subs. nigra NRRL3275 was obtained from the ATCC collection and cultured according to recommended protocols. For isolation of genomic DNA, M. megalomicea was grown in tryptone soya broth (TSB) (Hopwood et al., 1985) at 3000 rpm. S. lividans K4-114 (Ziermann and Betlach, 1999), which carries a deletion of the actinorhodin biosynthetic gene cluster, was used as the host for expression of the meg DEBS genes (see U.S. Pat. No. 6,177,262). S. lividans strains were maintained on R5 agar at 30° C. and were grown in liquid yeast extract-malt extract (YEME) for preparation of protoplasts (Hopwood et al., 1985). S. erythraea NRRL2338 was used for expression of the megosamine genes. S. erythraea strains were maintained on R5 agar at 34° C. and grown in liquid TSB for preparation of protoplasts.

(B) Manipulation of DNA and Organisms. Manipulation and transformation of DNA in E. coli was performed according to standard procedures (Sambrook et al., 1989) or to suppliers' protocols. Protoplasts of S. lividans and S. erythraea were generated for transformation by plasmid DNA using the standard procedure (Hopwood et al., 1985). S. lividans transformants were selected on R5 using 2 ml of a 0.5 mg/ml thiostrepton overlay. S. erythraea transformants were selected on R5 using 1.5 ml of a 0.6 mg/ml apramycin overlay.

(C) DNA Sequencing and Analysis. PCR-based double-stranded DNA sequencing was performed on a Beckman CEQ 2000 capillary sequencer using reagents and protocols provided by the manufacturer. A shotgun library of the entire cosmid pKOSO79-93D insert was made as follows: DNA was first digested with DraI to eliminate the vector fragment, then partially digested with Sau3AI. After agarose electrophoresis, bands between 1 and 3 kb were excised from the gel and ligated with BamHI digested pUC19. Another shotgun library was generated from a 12 kb XhoI-EcoRI fragment subcloned from cosmid pKOSO79-93A to extend the sequence to the megF gene. A 4 kb BglII-XhoI fragment from cosmid pKOS079-138B was sequenced by primer walking to extend the sequencing to the megBVI gene. Sequence was assembled using the SEQUENCHER (Gene Codes) software package and analyzed with MacVector (Oxford Molecular Group) and the NCBI BLAST server (www.ncbi.nlm.nih.gov/blast/).

EXAMPLE 2

Isolation of the Megalomicin Biosynthetic Gene Cluster

A cosmid library was prepared in SuperCos (Stratagene) vectors from M. megalomicea total DNA partially digested with Sau3AI and introduced into E. coli using a Gigapack III XL (Stratagene) in vitro packaging kit. $^{32}$P-labelled DNA probes encompassing the KS2 domain from DEBS, or a mixture of segments encompassing modules 1 and 2 from DEBS, were used separately to screen the cosmid library by colony hybridization. Several colonies which hybridized with the probes were further analyzed by sequencing the ends of their cosmid inserts using T3 and T7 primers. BLAST (Altschul et al., 1990) analysis of the sequences revealed several colonies with DNA sequences highly homologous to genes from the ery cluster. Together with restriction analysis, this led to the isolation of two overlapping cosmids, pKOSO79-93A and pKOSO79-93D which covered ~45 kb of the meg cluster. A 400 bp PCR fragment was generated from the left end of pKOSO79-93D and used to reprobe the cosmid library. Likewise, a 200 bp PCR fragment generated from the right end of pKOSO79-93A was used to reprobe the cosmid library. Analysis of hybridizing colonies, as described above, resulted in identification of two additional cosmids pKOSO79-138B adjacent to the 5' end of pKOS079-93D and pKOS205.57-2.3B which overlaps the 3' ends of pKOS079-93A and pKOSO79-93D cosmids. See FIG. 1.

BLAST analysis of the far left and right end sequences of these cosmids indicated no homology to any known genes related to polyketide biosynthesis, and therefore indicates that the set of four cosmids spans the entire megalomicin biosynthetic gene cluster.

The glycosyl synthase, transfer, and regulatory genes of the upstream region of the meg PKS are contained in the nucleotide sequence SEQ ID NO. 1.

The glycosyl synthase, and transfer genes of the downstream region of the meg PKS are contained in the nucleotide sequence SEQ ID NO: 2.

EXAMPLE 3

Production of a Modified Polyketide in a Heterologous Host

Fermentation for production of polyketide, LC/MS analysis, and quantification of 6-dEB for *S. lividans* K4-114/pKOS1O8-6 and *S. lividans* K4-114/pKAO127 'kan' were essentially as previously described (Xue et al., 1999). *S. erythraea* NRRL2338 and *S. erythraea*/pKOS97-42 were grown for 6 days in F1 medium (Brünker et al., 1998). Samples of broth were clarified in a microcentrifuge (5 mm, 13 000 rpm). For LC/MS preparation, isopropanol was added to the supernatant (1:2 ratio), and the supernatant centrifuged again. Samples were run on a C-18 reversed phase column (Inertsil ODS3, Metachem) using a 5-mM ammonium acetate (aqueous) acetonitrile-methanol (4:1) gradient (0-15%, 3 mm; 15-60%, 10 mm; 1 ml/min flow). Erythromycins and megalomicins were detected by electrospray mass spectrometry and quantity was determined by evaporative light scattering detection (ELSD). A purified extract from *M. megalomicea* containing megalomicin A, B, C1 and C2 was used for the standard reference. The LC retention time and mass spectra of erythromycin and the four megalomicins were identical to those from the standards. Thus the, *S. erythraea* host cell of the invention produced megalomicin in detectable and useful quantities.

EXAMPLE 4

Plasmids Incorporating Glycosyl Synthase and Transferase Genes

Plasmid pKOS108-6 is a modified version of pKAO127'kan' (Ziermann and Betlach, 1999, 2000), in which the eryAI-III genes between the PacI and EcoRI sites have been replaced with the megAI-III genes. This was carried out by first substituting a synthetic nucleotide DNA duplex (5'-TAAGAATTCGGAGATCTGGCCT-CAGCTCTAGAC (SEQ ID NO: 3), complementary oligo-5'-AATTGTCTAGAGCTGAGGCCAGATCTC-CGAATTCTTAAT (SEQ ID NO: 4)) between the PacI and EcoRI sites of the pKAO127'kan' vector fragment. The 22 kb EcoRI-BglII fragment from cosmid pKQS079-93D containing the megAI-II genes was inserted into EcoRI and BglII sites of the resulting plasmid to generate pKOS024-84. A 12 kb BglII-BbvCI fragment containing the megAIII and part of the megCII gene was subcloned from pKOS079-93A and excised as a BglII-XbaI fragment and ligated into the corresponding sites of pKOS024-84 to yield the final expression plasmid pKOS1O8-06. The megosamine integrating vector pKOS97-42 was constructed as follows: a subclone was generated containing the 4 kb XhoI-ScaI fragment from pKOS79-138B together with the 1.7 kb ScaI-PstI fragment from pKOS79-93D in Litmus 28 (Stratagene). The entire 5.7 kb fragment was then excised as a SpeI-PstI fragment and combined with the 6.3 kb PstI-EcoRI fragment from K0S79-93D and EcoRI-XbaI-digested pSET152 (Bierman et al., 1992) to construct plasmid pKOS97-42.

Cosmid pKOS79-138B contains the genes megR, megK, megCV, megCIV, and megBVI.

Cosmid pKOS205.57-2.3B contains the genes megCII, megCIII, megBII-2, megH, megF, megBIII, and megM and megL.

EXAMPLE 5

Production of Polyketide 3'''-O-methylmegalomicin A in a Heterologous Host

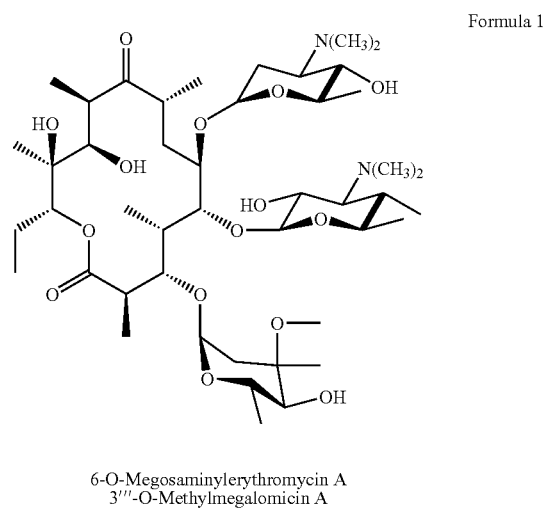

Formula 1

6-O-Megosaminylerythromycin A
3'''-O-Methylmegalomicin A

A) *Saccharopolyspora erythraea*—erythromycin A producing strain. Fermentation for production of polyketide, LC/MS analysis and quantification of 6-dEB for *S. erythraea* are essentially as described in Example 3. Plasmid vectors comprising the megD genes (DI, DII, DIII, DIV, DV, DVI, and DVII), are transformed into an erythromycin A producer strain of *Saccharopolyspora erythraea* excluding the megY gene, and optionally, extra copies of the eryG gene are provided. Culturing the transformed host cell under conditions that lead to the production of the compound of formula (1) having a methyl group in the 3''' position of the mycarose sugar moiety of megalomicin.

B) *Streptomyces coelicolor*, *S. lividans* or other heterologous host. Fermentation for production of polyketide, LC/MS analysis, and quantification of 6-dEB for *S. lividans* and *S. coelicolor* are essentially as described in Example 3. A vector or vectors including the PKS genes (megAI, megAII, and megAIII), mycarose genes (all megB genes), desosamine genes (all megC genes), megosamine genes (all megD genes), and megK and megF genes, eryG gene and optionally the megL and megM genes (the megL and megM genes can be considered members of the mycarose, desosamine, or megosamine biosynthetic gene sets in host cells that lack an analog gene of either) are transformed into *S. lividans* and *S. coelicolor*, and the transformed host is cultured under conditions that lead to the production of the compound of formula (1) having a methyl group in the 3''' position of the mycarose sugar moiety of megalomicin.

C) *Micromonospora megalomicea*. Fermentation for production of polyketide, LC/MS analysis, and quantification of 6-dEB for *Micromonospora megalomicea* are essentially as described in Example 3. A vector including a functional eryG gene and a disrupted megY are transformed into an *M. megalomicea* host, and the transformed host is cultured under conditions that lead to the production of the compound of formula (1) having a methyl group in the 3''' position of the mycarose sugar moiety of megalomicin.

EXAMPLE 6

Production of Erythronolide B in a Heterologous Host

The gene encoding a cytochrome P450 monooxygenase of the megalomicin cluster, megF, was PCR amplified and cloned into plasmid pET21, yielding plasmid pLB73. In this plasmid, megF is under the control of the φ10 promoter of T7.

Plasmid pLB73 was transformed into *E. coli* BL21 (DE3) and selected for resistance to apramycin.

Five ml of LB medium containing 100 μg/ml of ampicillin was inoculated with a fresh colony of BL21/pLB73. When the culture reached an $OD_{590}$ of 0.6 the expression of megF was induced by addition of 0.5 μM of IPTG, and the culture was incubated for 20 h at 37° C. in the presence of 100 μg of 6-dEB. The culture was centrifuged, and the supernatant was extracted with 5 mL of ethyl acetate and the organic phase dried under a stream of $N_2$. LC/MS analysis of the sample confirmed that approximately 50% of the 6-dEB had been converted into EB. LC conditions were as follows: MetaChem ODS-3 5 um reversed phase column, 4.6×150 mm; flow rate 1 mL/min; gradient of 35% to 100% acetonitrile in water over 8 minutes; MS detection using a PE-Sciex API100LC mass sensitive detector at 1 amu resolution from 200-1200 amu with an APCI ion source.

EXAMPLE 7

Production of 3-O-α-Mycarosyl-Erythronolide B in a Heterologous Host

Genes involved in the biosynthesis of mycarose were individually amplified by PCR using Deep Vent DNA polymerase (commercially available from NEB) from *M. megalomicea* chromosomal DNA with the following primers:

```
megL
forward: 5'-GGGGTCATATGAAGGCGCTTGTCCTGTCGG-3';    (SEQ ID NO:5)

reverse: 5'-GCAAAGCTTGTGACTAGTCGAGTAGTC-3';       (SEQ ID NO:6)

megM
forward: 5'-GACCTCCATATGACGACTCGACTCCTGGTC-3';    (SEQ ID NO:7)

reverse: 5'-TACTAGTCCCTCACACCATCGCCCG-3';         (SEQ ID NO:8)

megBIII
forward: 5'-CAGCATATGCCCGAAACGAGATGCCG-3';        (SEQ ID NO:9)

reverse: 5'-ATCGACTAGTTTCATCACACCACTTCCAGG-3';    (SEQ ID NO:10)

megBIV
forward: 5'-GCATATGACAAGACATGTCACACTTCTCGG-3';    (SEQ ID NO:11)

reverse: 5'-CCCACTAGTGTCACTCCTTGGTCGAGATGA-3';    (SEQ ID NO:12)

megF
forward: 5'-TGGTCATATGAAACTGCCCGATCTGGAGAG-3';    (SEQ ID NO:13)

reverse: 5'-CATACTAGTCTCATCCGTTCGGTCGCACCG-3';    (SEQ ID NO:14)

megDIV
forward: 5'-CCGGGCATATGAGGGTCGAGGAGCTG-3';        (SEQ ID NO:15)

reverse: 5'-GCACACTAGTCCGGGGTCACGTCCGC-3';        (SEQ ID NO:16)

megBV
forward: 5'-TGTACATATGCGGGTCCTGCTCACCTCG-3';      (SEQ ID NO:17)

reverse: 5'-ACACTAGTCACCTGTCGGCGCGGTGCTG-3';      (SEQ ID NO:18)

megBII-2
forward: 5'-CCGTCATCTGAGCACCGACGCCAC-3';          (SEQ ID NO:19)

reverse: 5'-AGGACTAGTGCGGGCTCTCACCGTAG-3';        (SEQ ID NO:20)

megBVI
forward: 5'-GGCATATGGGGGATCGGGTCAACGGTCATG-3';    (SEQ ID NO:21)

reverse: 5'-GTACTAGTTTCACGCCGTCGCCCGGTTGTAG-3';   (SEQ ID NO:22)
```

Each pair of primers introduces an NdeI site at the 5' end and a SpeI site at the 3' end of the gene amplified. PCR products were cloned into pCR-Blunt II-TOPO vector and the resulting plasmids were used to transform *E. coli* DH5α. The plasmids were digested with the enzymes NdeI and SpeI and fragments corresponding to each gene were cloned into a modified pET-24b previously digested with the same enzymes. The modifications introduced in the vector were the following: the region between the XbaI and EcoRI sites in the MCS was replaced by the sequence 5'-TCTAGAAG-GAGATATACATATGTGAACTAGTGAATTC-3' (SEQ ID NO:23) or by the sequence 5'-TCTAGAAGGAGATATA-CAATGCACCACCACCACCACCATATGT-GAACTAGTGAATTC-3' (SEQ ID NO:24) in case His-Tag fusions were required. These sequences contained the following sites XbaI, NdeI, SpeI and EcoRI restriction sites and the pET-24b RBS.

Plasmid DNA carrying the megL gene was digested with the enzymes XbaI and SpeI and the 1.1 kb fragment was cloned into the plasmid harboring the megM gene, previously digested with the enzyme SpeI. Clones with megM and megL genes in the same orientation were selected. The resulting plasmid was digested with the enzyme SpeI and was ligated to the 1.2 kb fragment obtained by digestion of the plasmid harboring megBIII gene with the enzymes XbaI and SpeI. Sequential cloning of the remaining genes into the pET-24b based vector was performed with the same pattern of restriction enzymes digestions and ligations. This resulted in construction of pLB80 with a 9.7 kb operon comprising nine genes involved in the biosynthesis of mycarose, in the following order: megM-megL-megBIII-megBIV-megF-megDIV-megBV-megBII-2-megBVI.

pLB80 plasmid was digested with the enzymes XbaI and HindIII and the 9.7 kb fragment was cloned into the plasmid pKOS146-83A digested with the same restriction enzymes, leaving the artificial mycarose operon under the control of the PactIII promoter. The resulting plasmid was digested with the enzymes EcoRI and SpeI and the 10.3 kb fragment was cloned into the plasmid pWHM3 digested with the enzymes XbaI and EcoRI to give the plasmid pLB92. Plasmid pLB92 was used to transform the S. coelicolor strain M145. Cultures of S. coelicolor M145 harboring the pLB92 plasmid were grown in YEME with thiostrepton (5 μg/ml) at 30° C. Cultures were fed with 6-deoxyerythronolide B (0.5 μg/ml) and after 96 hs they were centrifuged, and the supernatants were adjusted to pH 9-10 with sodium hydroxide. The supernatants were extracted with an equal volume of ethyl acetate and the organic layer was dried over $Na_2SO_4$, evaporated to dryness and redissolved in ethanol. The presence of 3-O-α-mycarosyl-erythronolide B was confirmed by LC/MS.

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

| SEQ ID NO.1-Sequence Containing Upstream Megalomicin Modification Enzyme Genes-pKOS079-138B |
|---|

```
   1 GCGCGCTTCG ATCACCATGG ATCGCTTAAT GTCCGGTTCC ATTGCTTTTC GATGGGGGAT

61 GTAGTGCAAT TGCAAAATCC GGAGACCGTG GTAAGCCTCG GAGTCCTGGG TCCGCTGTTC

121 GTCAGTTCCC CATCGCCGCG AAAGACGCCG ACGGCACGGA AACCGAGAAA TGTTCTCGCA

181 ATGCTCCTCG TCCACGCCGA CCAGGTCGTT CCGGTCTCCG TCCTGGTCTC CGAGCTCTGG

241 GACGACGAGC CGCCGGTCAG CAGGCTCACC ACCCTCCAGA CGTACATTCT CAATCTGCGC

301 AAGATGTTCG TGGCGGTCAC CGGTCTGCCC GCCGAGGAGG TCACCCGGAG TCTGCTCATC

361 ACCCGGGCCG GCGGCTATCT GCTCCGCGGT GACCGGATCG CCCTCGACGT CCGGGAGTAC

421 CAGCGTCTGA TGTCGGCCGG CTGCGCCGCG CTCGGCCTCG GCGACGACGT GACAGGCACC

481 CGCAGACTCA CCGAGGCGCT CGGCCTCTGG CGCGGGCCCG CGCTCGTCGA CGTCCCGCTG

541 GGTCGGGTGC TGGAGTCGAA GCGTCGCGAA CTGGAGGAGT CCTGGCTCAT GGCCAGCGAA

601 TACCTGGTCG GCGCGAAGTT GCGTCAGGGG ATGTACCGGG AGGCCCTCAT CGAGCTGACC

661 GCGCTCACCG CGGAGAATCC GCTGCACGAG GGGCTCCAGG CGCAGTACAT GCGGGCGCTG

721 CATCTCAGTG GTCGACGCGC GCAGGCGTTG GAGGTCTTCC ACCGGTTGCG TCGCAACCTC

781 GTCGACGAAC TGGGTCTGGA ACCGGAGCCG CAGGTGCAAC GGATCCACCA GGCGATCCTG

841 AACGCCGAGA CCGACTTCGA GGACGATCTG CGCCGTCATCC GTCCGTTTCC GTCCGAGGTC

901 GCCGCCACGA GTTGGGGTCG GGTCCGGGTC CGGGCGAGCT GACCGATTAC CGCGTACGGC

961 GACACCCTGA GCCGACAATC AACGACATTG GCGAAAATCG ACATCTGTGC CGGGGGGGA

1021 CGGGTTGGAC GACGAACGGT GGGGAGAACC ATGACCACTA TCGAACAGAT CCCGAGCATG

1081 GCCGAGGAGG CCGTTCTGCT CGACTGGCTG GCGGTGATGC GCGACAGGCA CCCGGTCTGG

1141 CAGGACCAGT ACGGCGTCTG GCACATCTTC CGCCACAGTG ACGTACGCGA GGTCCTCCGC

1201 GACACCGCCA CCTTCTCCTC CGACCCCACC CGCGTCATCG AGGGGCCGA CCCGACGCCG
```

SEQ ID NO.1-Sequence Containing Upstream Megalomicin Modification
Enzyme Genes-pKOS079-138B

```
1261 GGGATGATCC ACGAGATCGA CCCGCCGGAG CACCGGGCCC TGCGCAAGGT CGTCAGCAGC
1321 GCCTTCACCC CGCGTACGAT CGCCGACCTC GAACCGCGCA TCCGGGAGGT GACCCGGTCG
1381 CTGCTGGCCG ACGCCGGTGA CCGCTTCGAC CTGGTCGAGG CGCTCGCCTT CCCGCTGCCG
1441 GTCACGATCG TCGCCGAGCT GCTGGGGCTG CCCCGGATGG ACCACAAGCA GTTCGGTGAC
1501 TGGTCCGGCG CCCTGGTCGA CATCCAGATG GACGACCCGA CCGATCCGGC CCTGGTCGAA
1561 CGCATCATGC AGGTGCTGAA CCCGCTCACC TCCTACCTGC TCGACAGGTG TCGGGAACGG
1621 CGGGCCGACC CCCGGGACGA CCTGATCTCC CGGCTGGTGC TGGCCGAGGT CGACGGGCGC
1681 ACCCTCGACG ACGTGGAGGC GGCCAACTTC TCCACAGCGT TGCTGCTCGC GGGGCACATC
1741 ACCACCACCG TCCTGCTGGG CAACATCGTC CGCACCCTCG ACGAGCACCC GGAGTACTGG
1801 ACGGCCGCCC CGAGGACCC GGGTCTGATC GCGCCGATCA TCGAGGAGGT GTTGCGTTTC
1861 CGCCCCCCGT TCCCCCAGAT GCAGCGCACC ACGACCAGGG CCACCACCGT CGGTGGGGTC
1921 GAGATCCCGG CCGACGTCAT GGTCAACACC TGGGTGCTCT CGGCCAACCG CGATCCCCTG
1981 GCGCATCCCG ACCCGGACAC GTTCGACCCG TCCCGCAAGA TCGGTGGTGC CGCGCAGCTC
2041 TCCTTCGGGC ACGGCGTGCA CTTCTGTCTC GGTGCCCCGC TGGCGCGCCT GGAGAACCAG
2101 GTCGCCCTGG AGGAGATCAT CGCCCGGTAC GGTCGACTGG CCGTCGACCG CGACGACGAC
2161 ACGCTGCGTC ACTTCGACCA GATCGTCCTC GGCACCCGGC ACCTCCCGGT GCTGGCGGCG
2221 GTCACCCCGG CCGAGTCCGC CTGAACCCCT TGCGCTCCGA CGCGGCGGNN NNNNNNNNNN
2281 NNNNNNNNNN NNNNNNNNNN NNNNNNNNNN NNNNNNNNNN NNNNNNNNNN NNNNNNNNNN
2341 NNNNCNNCNT CNCNCCNCCG CCGCGCCGGG GCGGGTCGAC GCCGTTCAGA CGGCGCGGAT
2401 CAGGCCCCGA TGCTGATCCC ACCCGTCGGC GACGTCCCGT TCGAGTTGGT TGAGCCGGGC
2461 GGTCACCGAC TGGTCGAAAC CGTCGAGGAA GAACTCGTCC CCCGGCTGCG GATCGATGCT
2521 GCGGCCCGAC GTGACGAAGT CGTGGACGAC CGAGTGCAGG CTCCGGTCCG GGGTGACCCG
2581 GCCGGCGACG TAGCGGGTGG CCCCCGCCAG CCCGGGGAAA CCGGCCTCCC GGTACAGGTA
2641 GACGTCTCCG AGCAGGTCGA TCTGCACCGC CACCTGCGGA TGGCGGTCG GCGCATCGT
2701 TTCCGGCCGG ATCCGCAACA GCTGGGCGTC GACACCCCGA CGCAGGCTCT CCAACGCGTA
2761 ACCCAGGTCG GTCTGCATGC CCGGGGTCCG CTCGGCGGCG TAGTCGACGA ACCGGGCGAG
2821 GCCCTCCCGC AACTCGGTCC GTTCGCCCTC GGACAACCTG CCGTCGTCCC GACCGCTGTA
2881 GTCCTCGCGG ACGGTGACGA AGTCGAGCGG CCGGTGCGGG CTGGACTCGT TGAGTTCGGC
2941 GATGAAGTCG ACCAGGTCGA TGAGGCGGTT GGCCCGCCCC GGCAGGATGA TGTGGTTGAG
3001 GCCGAGCCGG ACCGGTGCCG CCCGTTCGGC GCGCATCCGC AGGAAGTCCC GGAGGTTCTT
3061 CCTGACCCGT TCGAAGGCGC CACGCTTGCC GGTGGTGGCC TGGTACTCGT CGTTGTTCAG
3121 CCCGTACAGG GAGGTACGGA CCGCGCCGAG GTCCCACAGG CCGGGCTGGC GGCGCAGCGT
3181 CTGTTCGGTG AGGGCGAAGG CGTTGGTGTA GACGGTCAGG GCGAAGCCCC GCCGGGCGGC
3241 GTGCGACACC AACGCCCCGA TACCCGGGTT GGTCAACGGT TCCAGGCCGC CGGAGAGGTA
3301 CATCGCCGTC GGGTTCTCCG ACGGCACCTC GTCGATGACC GAGGTGAGGA TCTCGTTGCC
3361 GGGCACCACC GACTCCGCGT CGTACTTGGC ACCTGTCACC CGTACGCAGA AGTGACAGCG
3421 GAACATGCAC GTCGGGCCGG GGTAGAGCCC GACGCTGTAC GGGAAGGCGG GCTCCCGCCG
3481 TACCGCAGCC TCCAACGCGC CGGCGGCGTT CAGCGGCCTG ATCGTGTTGC TCCAGTACTT
```

-continued

SEQ ID NO.1-Sequence Containing Upstream Megalomicin Modification
Enzyme Genes-pKOS079-138B

```
3541 GCCCGCCGGG CCCTGCTCCA CCGCCGTGCC CAGCTGCGGG ATGCGATCGA ACAGGTCGAG
3601 CAGCTCGCCG AACCCGGCCC GGTCCAGGTC GAACCGACGG CGCATCTGCT CCAACGGGGT
3661 GAACGGCGAG GCGCCGTAGT GGGCGGTGAG TTCGGCGAGC CGGACCGCCT GTCGTTCGGC
3721 GGTGTCGGAT GCGGCACCGG TGAGGCGGGT GACCTCGGCG CTGAGCGCCC GCACCACGGC
3781 CGGCCGGTCG GCGTCGGGTC GTGCCGCGTC CGCGATCTCC GTCGGTACGG CGGTCGCCGT
3841 AGGAGTGGTC TTCATCGACG TGCGAACCCT TCTGGCGTCT GTGGTGCGAG GATCACGAAC
3901 CGTTGCGTTT CCGCTTGTCC CACTCCGCGT TGATCAACGC ACCGCTGGTG GTGGCGAGTC
3961 GGATGACGTC GCACACCCGG CGGATGTCCT CACTGGACAC CGAGGGGCCG GTCGGGAGGG
4021 CGAGCACCCG TTCGGCGAGC CACTCGGTCT GTGTCAGCCG CAGCGGTGGC TCCGTGCGGT
4081 AGGGCGTCAT CTGGTGGCAG GCGGGGGAGA AGTAGGGCTG TGCGACGACC TTCTCCGCGC
4141 GCAGGATCGC CTGCAGCCGG TCACGGTCGA TGCCGGTGGC GGTGCCGTCC ACCAGGATGA
4201 TCACGTACTG GTAGTTGCTC TCCTCGTCGG GCGGGAGCGA GTGCACGGTG ACGCCGCGTA
4261 CGTCGCGCAG CTCGCTGGTG TAGAGCGCGT GGTTGACCCG GTTGTGCTCC CTGGTCTCGG
4321 CGAACGCGTC GAGGGAGGTG AGCCCCATGG CCGCGGCGCA CTCGCTCATC TTGCCGTTGG
4381 TGCCGATCTC GGTGACCACC TTGTCCGGGC CGATGCCGAA GTTGTGCATG GCCCGGATCC
4441 GTTCGGCCAG CAGGCCGTCG TCGGTGACCA CCGCCCCGCC CTCGAAGGCG GTGACCGCCT
4501 TGGTGGCGTG GAAGCTGAAC ACCTCGGCGT CACCGGATCC GCCCACCGGA CGTCCACCCG
4561 TCGTGCAGCC CAGGGCGTGG GCGGCGTCGA AGAAGAGCTT GACCTGGTGG TCGGCGGCGA
4621 TCTTCGCCAG CGCCTCCACA GGTGCTGGTC GGCCCACAG GTGTACGCCG ACGATCGCGC
4681 CGGTCTGCGG GGTGACGAGC GCGGCGACGT GGTCCGGGTC GACCAGACCG GTCGCCGGGT
4741 CGACGTCGCA GAACACCGGT GTGAGTCCGA GCCAGCTCGC CGCGTGCGCG GTGGCCGCGA
4801 AGGTCATTGA CGGCATGATC ACTTCACCGG TGACGTCACC GGCCCGCAGC ACCAGTTCCA
4861 GGGCGACGGT GGCGTTGCAG GTGGCGATGC AGTGCCGTAC CCCGACCAGG TCGGCGACCC
4921 GGGCCTCGAA CTCCCGCACC AGGGGCCCGC CGTTGGTGAG CCAGTTGTTG TTCAGGGCCC
4981 ACTCCAGGCG GGCCAGGAAC CGCTGCCGGT CGCCGATCGT CGGCCGGCCC ACGTGCAGGG
5041 GGTGCAGGAA CGCCTCGGGA CCGCCGAAGA TCGCCAGATC GGTCGGTACG CGCTTCACGC
5101 CGTCGCCCGG TTGTAGACGG CGGACGCGCA GGCGACGAGG CTGCGCAGCT GGATGTTGAC
5161 GTAGTGGCTG TGCGCGAGCA GTTCGGTGAT CTGGCCGAAG GTCATCCACC GGTGGTCGGG
5221 GGCACCGCCG TCGTCGAAGT CCGCGGGCAC CTCGACGAGC ATGTACCGGT TCTCGTTGCG
5281 GTAGAACCGC CCACCCTCCT CGGAGTGCCA GGCGTCGTAG CGGATCTGGG TACGCGGGAC
5341 GTCCAGCACG TAGTCGAGGT AGGTCGGGCG GTGTTCCTCG GCACGTCGG TGTAGTTGTC
5401 CGGCTGACAG TGCACCGTCG CCGCCAACTC GGCGACGTCG TGGCCACCCG CCTCGGTGCG
5461 CAGGTGCACG AGCGCGTGGA GGGTGCCGTC GATCTCCTTG ACCAGGAGGG CGAGCATGCC
5521 GTGGTTGGCG GGGAGAGCA GCGGTTGCAT CCAGGACCTC ACCTCGCGGT GACTGGTCGT
5581 CACGGAGACG CCGAAGATGC TGAAGTACTT CTTGTCCTCG TGTTCGATGC CGTCGTCGCG
5641 CCGGATCCAC CCGCTGCGGT CGATGTCGGC CAACGGCCGG GTGCGTTGGA CGAACTCACG
5701 TGTGGTGCGT ACGTCCGAGA TCCAGCTCAG CAGGGTGTTC ATGTTGTGGA CCGGGGTGCC
5761 CGCCCCGACG AAGGAACGCA GCAGTCGGGT CTCGAAGGAC CCCTGGGGCA GTCCGTCCAG
```

SEQ ID NO.1-Sequence Containing Upstream Megalomicin Modification Enzyme Genes-pKOS079-138B

```
5821 TACCCGGCCG ACGGCCCCGG CTTCCACCCT GGTCGGTATG CAGGCCAGCA CGGACCGCAG
5881 GTCCATGTTC ACCACGTTGT CGTAGCGGAG CATCGCCCGC AGCTGGGCGA GGGTGAGCCA
5941 CCTGCAGTTC GGGTGCTCGG GCGGGTCCTC GAAGACCTCG ACCACCATGT TGCGGTTGCG
6001 TTTGCGCAGG AACCAGGAAC CCTGCTCGGA CTGGAGGACG TCGACGAGGA TCCGGTGGGG
6061 GCGGGTCCCG TCGAAGTACT CGATGAACTG GACGCGGGAT CCGTTGTGGA CCCTCATGTA
6121 GTTGCTGCGG GTGGCCTGCA GGGTCGGCGA GAGCTGGACG GCGTTGATGT TGCCAGGTTC
6181 GGCCTTGGCC TGCACCAGAG CGTGCAGTAC GCCGTCGAAC TCCCGCACGA TCAGACCGAG
6241 GAACCCGATC TCGGGTTGGA CGATGATGGG TTGGATCCAG TCCCGTCGCC ATCCGAAGTT
6301 GGTCCGGACG TGCAGGCCCT CGATGGAGAA GAAGCGCCCG GAGTCGTGCC CCAGCCGACC
6361 GTCCTCCGGG TGGAACGACC AGCGTTCCAT GGTGCTGAAG GGCACTCGGT GCACCTCGAG
6421 CCGATGCTCG GCGGCGCGGT GGGCCAACCA GTCGTGGACG TCGTCGGTGG CGGTGGGAGG
6481 TCCGCCGTGC CGAGTCAGGA AACGTATTGC GATTGTGTG GATTCCGGAG TCGCATGACC
6541 GTTGACCCGA TCCCCCATAC GCCTCTCCCG TGATGTCGTG GGCGGTCCGT GCGGTACCGC
6601 CCGGACTGAC ATTCGTCGAT CAAGACCCCG CCCAGTGTAG GGCTCCGCCC GCGACGGGAG
6661 AAGGTCCGTC GAACAACTTC CGGGTGACCG GTCGCCGGCG TCGGTGAAAC GGGCGTCGGA
6721 GCACCCGATC ATTGCTGTCG GTGAACTTCC TAACTGTCGG CGCGCACATC TTTCTGACCG
6781 GTGTGTTCCG TGGTATGACG CGTTCCCGGC CCGTCTGGAA CTGTGCGTGG GACTGACCGG
6841 TTGCGGCGTG TTTTCGCCCG TTTCCGAACT GCGGATTCGT CGATCGCGCA GGTGGGAGCG
6901 GGTGGCTGAC CGGGATGATC TGCAATCATG GCGCTCAATG ACGATCTCTT GTAGCATGGT
6961 CCGCGCCGAG GGTCCGACAG GCCCGAAACG CCCGGCATCC AGCCTGTTCG ACGACGTCGA
7021 CATCACCGTG CAAGCCGCGA TGACACCGAC ACCACGCCAT GCTGGTGCCG CACTGGAAGG
7081 GTGGCGCGAT CAGGGAAATG GCCGTGTCAC TAGACAGACG CCAAACAGCT GTCCGGGCCT
7141 GCGGAAACAG CATCGATCTG CGTCAGCCGT TCATTGCCCC GGCGGCACCG CCTTGGAAAT
7201 CCGTGCCACC GGTCGTCCGC AGTGACGATC GCGGACCCGG GTTTCGAGAC AGCAGGTAGT
7261 AGGCGATGCA GGCGTTTCGT CTCGCGCCGG ACGCGTCGCA CTAGGTGGAA TCCGTCACAG
7321 TCTTCAATCC GGGAGCGTTC TATGGCAGTT GGCGATCGAA GGCGGCTGGG CCGGGAGTTG
7381 CAGATGGCCC GGGGTCTCTA CTGGGGGTTC GGTGCCAACG GCGATCTGTA CTCGATGCTC
7441 CTGTCCGGAC GGGACGACGA CCCCTGGACC TGGTACGAAC GGTTGCGGGC CGCCGGACGG
7501 GGACCGTACG CCAGTCGGGC CGGAACGTGG GTGGTCGGTG ACCACCGGAC CGCCGCCGAG
7561 GTGCTCGCCG ATCCGGGCTT CACCCACGGC CCGCCCGACG CTGCCCGGTG GATGCAGGTG
7621 GCCCACTGCC CGGCGGCCTC CTGGGCCGGC CCCTTCCGGG AGTTCTACGC CCGCACCGAG
7681 GACGCGGCGT CGGTGACAGT GGACGCCGAC TGGCTCCAGC AGCGGTGCGC CAGGCTGGTG
7741 ACCGAGCTGG GGTCGCGCTT CGATCTCGTG AACGACTTCG CCCGGGAGGT CCCGGTGCTG
7801 GCGCTCGGTA CCGCGCCCGC ACTCAAGGGC GTGGACCCCG ACCGTCTCCG GTCCTGGACC
7861 TCGGCGACCC GGGTATGCCT GGACGCCCAG GTCAGCCCGC AACAGCTCGC GGTGACCGAA
7921 CAGGCGCTGA CCGCCCTCGA CGAGATCGAC GCGGTCACCG GCGGTCGGGA CGCCGCGGTG
7981 CTGGTGGGGG TGGTGGCGGA GCTGGCGGCC AACACGGTGG CAACGCCGT CCTGGCCGTC
8041 ACCGAGCTTC CCGAACTGGC GGCACGACTT GCCGACGACC CGGAGACCGC GACCCGTGTG
```

-continued

| SEQ ID NO.1-Sequence Containing Upstream Megalomicin Modification Enzyme Genes-pKOS079-138B |
|---|

```
8101 GTGACGGAGG TGTCGCGGAC GAGTCCCGGC GTCCACCTGG AACGCCGCAC CGCCGCGTCG
8161 GACCGCCGGG TGGGCGGGGT CGACGTCCCG ACCGGTGGCG AGGTGACAGT GGTCGTCGCC
8221 GCGGCGAACC GTGATCCCGA GGTCTTCACC GATCCCGACC GGTTCGACGT GGACCGTGGC
8281 GGCGACGCCG AGATCCTGTC GTCCCGGCCC GGCTCGCCCC GCACCGACCT CGACGCCCTG
8341 GTGGCCACCC TGGCCACGGC GGCGCTGCGG GCCGCCGCGC CGGTGTTGCC CCGGCTGTCC
8401 CGTTCCGGGC CGGTGATCAG ACGACGTCGG TCACCCGTCG CCCGTGGTCT CAGCCGTTGC
8461 CCGGTCGAGC TGTAGAGGAA GAACGATGCG CGTCGTGTTT TCATCGATGG CTGTCAACAG
8521 CCATCTGTTC GGGCTGGTCC CGCTCGCAAG CGCCTTCCAG GCGGCCGGAC ACGAGGTACG
8581 GGTCGTCGCC TCGCCGGCCC TGACCGACGA CGTCACCGGT GCCGGTCTGA CCGCCGTGCC
8641 CGTCGGTGAC GACGTGGAAC TTGTGGAGTG GCACGCCCAC GCGGGCCAGG ACATCGTCGA
8701 GTACATGCGG ACCCTCGACT GGGTCGACCA GAGCCACACC ACCATGTCCT GGGACGACCT
8761 CCTGGGCATG CAGACCACCT TCACCCCGAC CTTCTTCGCC CTGATGAGCC CCGACTCGCT
8821 CATCGACGGG ATGGTCGAGT CTGCCGCTC CTGGCGTCCC GACCTGATCG TCTGGGAGCC
8881 GCTGACCTTC GCCGCCCCGA TCGCGGCCCG GGTCACCGGA ACCCCGCACG CCCGGATGCT
8941 GTGGGGTCCG GACGTCGCCA CCCGGGCCCG GCAGAGCTTC CTGCGACTGC TGGCCCACCA
9001 GGAGGTGGAG CACCGGGAGG ATCC
```

| SEQ ID NO.2-Sequence Containing Downstream Megalomicin Modification Genes-KOS205-57-2.3B |
|---|

```
   1 CCGCGCTCGC CGAGGCGTAC ACCCGGGGGG TGGAGGTCGA CTGGCGTACC GCAGTGGGTG
  61 AGGGACGCCC GGTCGACCTG CCGGTCTACC CGTTCCAACG ACAGAACTTC TGGCTCCCGG
 121 TCCCCCTGGG CCGGGTCCCC GACACCGGCG ACGAGTGGCG TTACCAGCTC GCCTGGCACC
 181 CCGTCGACCT CGGGCGGTCC TCCCTGGCCG GACGGGTCCT GGTGGTGACC GGAGCGGCAG
 241 TACCCCCGGC CTGGACGGAC GTGGTCCGCG ACGGCCTGGA ACAGCGCGGG GCGACCGTCG
 301 TGTTGTGCAC CGCGCAGTCG CGCGCCCGGA TCGGCGCCGC ACTCGACGCC GTCGACGGCA
 361 CCGCCCTGTC CACTGTGGTC TCTCTGCTCG CGCTCGCCGA GGGCGGTGCT GTCGACGACC
 421 CCAGCCTGGA CACCCTCGCG TTGGTCCAGG CGCTCGGCGC AGCCGGGATC GACGTCCCCC
 481 TGTGGCTGGT GACCAGGGAC GCCGCCGCCG TGACCGTCGG AGACGACGTC GATCCGGCCC
 541 AGGCCATGGT CGGTGGGCTC GGCCGGGTGG TGGGCGTGGA GTCCCCCGCC CGGTGGGGTG
 601 GCCTGGTGGA CCTGCGCGAG GCCGACGCCG ACTCGGCCCG GTCGCTGGCC GCCATACTGG
 661 CCGACCCGCG CGGCGAGGAG CAGTTCGCGA TCCGGCCCGA CGGCGTCACC GTCGCCCGTC
 721 TCGTCCCGGC ACCGGCCCGC GCGGCGGGTA CCCGGTGGAC GCCGCGCGGG ACCGTCCTGG
 781 TCACCGGCGG CACCGGCGGC ATCGGCGCGC ACCTGGCCCG CTGGCTCGCC GGTGCGGGCG
 841 CCGAGCACCT GGTGCTGCTC AACAGGCGGG GAGCGGAGGC GGCCGGTGCC GCCGACCTGC
 901 GTGACGAACT GGTCGCGCTC GGCACGGGAG TCACCATCAC GGCCTGCGAC GTCGCCGACC
 961 GCGACCGGTT GGCGGCCGTC CTCGACGCCG CACGGGCGCA GGGACGGGTG GTCACGGCGG
1021 TGTTCCACGC CGCCGGGATC TCCCGGTCCA CAGCGGTACA GGAGCTGACC GAGAGCGAGT
```

-continued

SEQ ID NO.2-Sequence Containing Downstream Megalomicin Modification Genes-KOS205-57-2.3B

```
1081  TCACCGAGAT CACCGACGCG AAGGTGCGGG GTACGGCGAA CCTGGCCGAA CTCTGTCCCG
1141  AGCTGGACGC CCTCGTGCTG TTCTCCTCGA ACGCGGCGGT GTGGGGCAGC CCGGGGCTGG
1201  CCTCCTACGC GGCGGGCAAC GCCTTCCTCG ACGCCTTCGC CCGTCGTGGT CGGCGCAGTG
1261  GGCTGCCGGT CACCTCGATC GCCTGGGGTC TGTGGGCCGG GCAGAACATG GCCGGTACCG
1321  AGGGCGGCGA CTACCTGCGC AGCCAGGGCC TGCGCGCCAT GGACCCGCAG CGGGCGATCG
1381  AGGAGCTGCG GACCACCCTG GACGCCGGGG ACCCGTGGGT GTCGGTGGTG GACCTGGACC
1441  GGGAGCGGTT CGTCGAACTG TTCACCGCCG CCCGCCGCCG GCCCCTCTTC GACGAACTCG
1501  GTGGGGTCCG CGCCGGGGCC GAGGAGACCG GTCAGGAATC GGATCTCGCC CGGCGGCTGG
1561  CGTCGATGCC GGAGGCCGAA CGTCACGAGC ATGTCGCCCG GCTGGTCCGA GCCGAGGTGG
1621  CAGCGGTGCT GGGCCACGGC ACGCCGACGG TGATCGAGCG TGACGTCGCC TTCCGTGACC
1681  TGGGATTCGA CTCCATGACC GCCGTCGACC TGCGGAACCG GCTCGCGGCG GTGACCGGGG
1741  TCCGGGTGGC CACGACCATC GTCTTCGACC ACCCGACAGT GGACCGCCTC ACCGCGCACT
1801  ACCTGGAACG ACTCGTCGGT GAGCCGGAGG CGACGACCCC GGCTGCGGCG GTCGTCCCGC
1861  AGGCACCCGG GGAGGCCGAC GAGCCGATCG CGATCGTCGG GATGGCCTGC CGCCTCGCCG
1921  GTGGAGTGCG TACCCCCGAC CAGTTGTGGG ACTTCATCGT CGCCGACGGC GACGCGGTCA
1981  CCGAGATGCC GTCGGACCGG TCCTGGGACC TCGACGCGCT GTTCGACCCG GACCCCGAGC
2041  GGCACGGCAC CAGCTACTCC CGGCACGGCG CGTTCCTGGA CGGGGCGGCC GACTTCGACG
2101  CGGCGTTCTT CGGGATCTCG CCGCGTGAGG CGTTGGCGAT GGATCCGCAG CAGCGGCAGG
2161  TCCTGGAGAC GACGTGGGAG CTGTTCGAGA ACGCCGGCAT CGACCCGCAC TCCCTGCGCG
2221  GTACGGACAC CGGTGTCTTC CTCGGCGCTG CGTACCAGGG GTACGGCCAG AACGCGCAGG
2281  TGCCGAAGGA GAGTGAGGGT TACCTGCTCA CCGGTGGTTC CTCGGCGGTC GCCTCCGGTC
2341  GGATCGCGTA CGTGTTGGGG TTGGAGGGGC CGGCGATCAC TGTGGACACG GCGTGTTCGT
2401  CGTCGCTTGT GGCGTTGCAC GTGGCGGCCG GGTCGCTGCG ATCGGGTGAC TGTGGGCTCG
2461  CGGTGGCGGG TGGGGTGTCG GTGATGGCCG GTCCGGAGGT GTTCACCGAG TTCTCCAGGC
2521  AGGGCGCGCT GGCCCCCGAC GGTCGGTGCA AGCCCTTCTC CGACCAGGCC GACGGGTTCG
2581  GATTCGCCGA GGGCGTCGCT GTGGTGCTCC TGCAGCGGTT GTCGGTGGCG GTGCGGGAGG
2641  GGCGTCGGGT GTTGGGTGTG GTGGTGGGTT CGGCGGTGAA TCAGGATGGG GCGAGTAATG
2701  GGTTGGCGGC GCCGTCGGGG GTGGCGCAGC AGCGGGTGAT TCGGCGGGCG TGGGGTCGTG
2761  CGGGTGTGTC GGGTGGGGAT GTGGGTGTGG TGGAGGCGCA TGGGACGGGG ACGCGGTTGG
2821  GGGATCCGGT GGAGTTGGGG GCGTTGTTGG GGACGTATGG GGTGGGTCGG GGTGGGGTGG
2881  GTCCGGTGGT GGTGGGTTCG GTGAAGGCGA ATGTGGGTCA TGTGCAGGCG GCGGCGGGTG
2941  TGGTGGGTGT GATCAAGGTG GTGTTGGGGT TGGGTCGGGG GTTGGTGGGT CCGATGGTGT
3001  GTCGGGGTGG GTTGTCGGGG TTGGTGGATT GGTCGTCGGG TGGGTTGGTG GTGGCGGATG
3061  GGGTGCGGGG GTGGCCGGTG GGTGTGGATG GGGTGCGTCG GGGTGGGGTG TCGGCGTTTG
3121  GGGTGTCGGG GACGAATGCT CATGTGGTGG TGGCGGAGGC GCCGGGGTCG GTGGTGGGGG
3181  CGGAACGGCC GGTGGAGGGG TCGTCGCGGG GTTGGTGGGG GTGGCTGGT GGTGTGGTGC
3241  CGGTGGTGCT GTCGGCAAAG ACCGAAACCG CCCTGACCGA GCTCGCCCGA CGACTGCACG
3301  ACGCCGTCGA CGACACCGTC GCCCTCCCGG CGGTGGCCGC CACCCTCGCC ACCGGACGCG
```

-continued

SEQ ID NO.2-Sequence Containing Downstream Megalomicin Modification Genes-KOS205-57-2.3B

```
3361 CCCACCTGCC CTACCGGGCC GCCCTGCTGG CCCGCGACCA CGACGAACTG CGCGACAGGC
3421 TGCGGGCGTT CACCACTGGT TCGGCGGCTC CCGGTGTGGT GTCGGGGGTG GCGTCGGGTG
3481 GTGGTGTGGT GTTTGTTTTT CCTGGTCAGG GTGGTCAGTG GGTGGGGATG GCGCGGGGGT
3541 TGTTGTCGGT TCCGGTGTTT GTGGAGTCGG TGGTGGAGTG TGATGCGGTG GTGTCGTCGG
3601 TGGTGGGGTT TTCGGTGTTG GGGGTGTTGG AGGGTCGGTC GGGTGCGCCG TCGTTGGATC
3661 GGGTGGATGT GGTGCAGCCG GTGTTGTTCG TGGTGATGGT GTCGTTGGCG CGGTTGTGGC
3721 GGTGGTGTGG GGTTGTGCCT GCGGCGGTGG TGGGTCATTC GCAGGGGGAG ATCGCGGCGG
3781 CGGTGGTGGC GGGGGTGTTG TCGGTGGGTG ATGGTGCGCG GGTGGTGGCG TTGCGGGCGC
3841 GGGCGTTGCG GGCGTTGGCC GGCCACGGCG GCATGGTCTC CCTCGCGGTC TCCGCCGAAC
3901 GCGCCCGGGA GCTGATCGCA CCCTGGTCCG ACCGGATCTC GGTGGCGGCG GTCAACTCCC
3961 CGACCTCGGT GGTGGTCTCG GGTGACCCAC AGGCCCTCGC CGCCCTCGTC GCCCACTGCG
4021 CCGAGACCGG TGAGCGGGCC AAGACGCTGC CTGTGGACTA CGCCTCCCAC TCCGCCCACG
4081 TCGAACAGAT CCGCGACACG ATCCTCACCG ACCTGGCCGA CGTCACGGCG CGCCGACCCG
4141 ACGTCGCCCT CTACTCCACG CTGCACGGCG CCCGGGGCGC CGGCACGGAC ATGGACGCCC
4201 GGTACTGGTA CGACAACCTG CGCTCACCGG TGCGCTTCGA CGAGGCCGTC GAGGCCGCCG
4261 TCGCCGACGG CTACCGGGTC TTCGTCGAGA TGAGCCCACA CCCGGTCCTC ACCGCCGCGG
4321 TGCAGGAGAT CGACGACGAG ACGGTGGCCA TCGGCTCGCT GCACCGGGAC ACCGGCGAGC
4381 GGCACCTGGT CGCCGAACTC GCCCGGGCCC ACGTGCACGG CGTACCAGTG GACTGGCGGG
4441 CGATCCTCCC CGCCACCCAC CCGGTTCCCC TGCCGAACTA CCCGTTCGAG GCGACCCGGT
4501 ACTGGCTCGC CCCGACGGCG GCCGACCAGG TCGCCGACCA CCGCTACCGC GTCGACTGGC
4561 GGCCCCTGGC CACCACCCCG GCGGAGCTGT CCGGCAGCTA CCTCGTCTTC GGCGACGCCC
4621 CGGAGACCCT CGGCCACAGC GTCGAGAAGG CCGGCGGGCT CCTCGTCCCG GTGGCCGCTC
4681 CCGACCGGGA GTCCCTCGCG GTCGCCCTGG ACGAGGCGGC CGGACGACTC GCCGGTGTGC
4741 TCTCCTTCGC CGCCGACACC GCCACCCACC TGGCCCGGCA CCGACTCCTC GGCGAGGCCG
4801 ACGTCGAGGC CCCACTCTGG CTGGTCACCA GCGGCGGCGT CGCACTCGAC GACCACGACC
4861 CGATCGACTG CGACCAGGCA ATGGTGTGGG GGATCGGACG GGTGATGGGT CTGGAGACCC
4921 CGCACCGGTG GGGCGGCCTG GTGGACGTGA CCGTCGAACC CACCGCCGAG GACGGGGTGG
4981 TCTTCGCCGC CCTCCTGGCC GCCGACGACC ACGAGGACCA GGTGGCGCTG CGCGACGGCA
5041 TCCGCCACGG CCGACGGCTC GTCCGCGCCC CGCTGACCAC CCGAAACGCC AGGTGGACAC
5101 CGGCGGGCAC GGCGCTCGTC ACGGGCGGTA CGGGTGCCCT CGGCGGCCAC GTCGCGCGGT
5161 ACCTGGCCCG GTCCGGGGTG ACCGATCTCG TCCTGCTCAG CAGGAGCGGC CCCGACGCAC
5221 CCGGTGCCGC CGAACTGGCC GCCGAACTGG CCGACCTCGG GGCCGAGCCG AGAGTCGAGG
5281 CGTGCGACGT CACCGACGGG CCACGCCTGC GCGCCCTGGT GCAGGAGCTA CGGGAACAGG
5341 ACCGGCCGGT CCGGATCGTC GTCCACACCG CAGGGGTGCC CGACTCCCGT CCCCTCGACC
5401 GGATCGACGA ACTGGAGTCG GTCAGCGCCG CGAAGGTGAC CGGGGCGCGG CTGCTCGACG
5461 AGCTCTGCCC GGACGCCGAC ACCTTCGTCC TGTTCTCCTC GGGGGCGGGA GTGTGGGGTA
5521 GCGCGAACCT GGGCGCGTAC GCGGCAGCCA ACGCCTACCT GGACGCCCTG GCCCACCGCC
5581 GCCGCCAGGC GGGCCGGGCC GCGACCTCGG TCGCCTGGGG GGCGTGGGCC GGCGACGGCA
```

-continued

SEQ ID NO.2-Sequence Containing Downstream Megalomicin Modification Genes-KOS205-57-2.3B

```
5641 TGGCCACCGG CGACCTCGAC GGGCTGACCC GGCGCGGTCT GCGGGCGATG GCACCGGACC
5701 GGGCGCTGCG CGCCTGCACC AGGCGTTGGA CCACCCACGA CACCTGTGTG TCGGTAGCCG
5761 ACGTCGACTG GGACCGCTTC GCCGTGGGTT TCACCGCCGC CCGGCCCAGA CCCCTGATCG
5821 ACGAACTCGT CACCTCCGCG CCGGTGGCCG CCCCCACCGC TGCGGCGGCC CCGGTCCCGG
5881 CGATGACCGC CGACCAGCTA CTCCAGTTCA CGCGCTCGCA CGTGGCCGCG ATCCTCGGTC
5941 ACCAGGACCC GGACGCGGTC GGGTTGGACC AGCCCTTCAC CGAGCTGGGC TTCGACTCGC
6001 TCACCGCCGT CGGCCTGCGC AACCAGCTCC AGCAGGCCAC CGGGCGGACG CTGCCCGCCG
6061 CCCTGGTGTT CCAGCACCCC ACGGTACGCA GACTCGCCGA CCACCTCGCG CAGCAGCTCG
6121 ACGTCGGCAC CGCCCCGGTC GAGGCGACGG GCAGCGTCCT GCGGGACGGC TACCGGCGGG
6181 CCGGGCAGAC CGGCGACGTC CGGTCGTACC TGGACCTGCT GGCGAACCTG TCGGAGTTCC
6241 GGGAGCGGTT CACCGACGCG GCGAGCCTGG GCGGACAGCT GGAACTCGTC GACCTGGCCG
6301 ACGGATCCGG CCCGGTCACT GTGATCTGTT GCGCGGGCAC TGCGGCGCTC TCCGGGCCGC
6361 ACGAGTTCGC CCGACTCGCC TCGGCGCTGC GCGGCACCGT GCCGGTGCGC GCCCTCGCGC
6421 AACCCGGGTA CGAGGCGGGT GAACCGGTGC CGGCGTCGAT GGAGGCAGTG CTCGGGGTGC
6481 AGGCGGACGC GGTCCTCGCG GCACAGGGCG ACACGCCGTT CGTGCTGGTC GGACACTCGG
6541 CGGGGGCCCT GATGGCGTAC GCCCTGGCGA CCGAGCTGGC CGACCGGGGC CACCCGCCAC
6601 GTGGCGTCGT GCTCCTCGAC GTGTACCCAC CCGGTCACCA GGAGGCGGTG CACGCCTGGC
6661 TCGGCGAGCT GACCGCCGCC CTGTTCGACC ACGAGACCGT ACGGATGGAC GACACCCGGC
6721 TCACGGCCCT GGGGGCGTAC GACAGGCTGA CCGGCAGGTG GCGTCCGAGG GACACCGGTC
6781 TGCCCACGCT GGTGGTGGCC GCCAGCGAGC CGATGGGGGA GTGGCCGGAC GACGGTTGGC
6841 AGTCCACGTG GCCGTTCGGG CACGACAGGG TCACGGTGCC CGGTGACCAC TTCTCGATGG
6901 TGCAGGAGCA CGCCGACGCG ATCGCGCGGC ACATCGACGC CTGGTTGAGC GGGGAGAGGG
6961 CATGAACACG ACCGATCGCG CCGTGCTGGG CCGACGACTC CAGATGATCC GGGGACTGTA
7021 CTGGGGTTAC GGCAGCAACG GAGACCCGTA CCCGATGCTG TTGTGCGGGC ACGACGACGA
7081 CCCGCACCGC TGGTACCGGG GGCTGGGCGG ATCCGGGGTC CGGCGCAGCC GTACCGAGAC
7141 GTGGGTGGTG ACCGACCACG CCACCGCCGT GCGGGTGCTC GACGACCCGA CCTTCACCCG
7201 GGCCACCGGC CGGACGCCGG AGTGGATGCG GGCCGCGGGC GCCCCGGCCT CGACCTGGGC
7261 GCAGCCGTTC CGTGACGTGC ACGCCGCGTC CTGGGACGCC GAACTGCCCG ACCCGCAGGA
7321 GGTGGAGGAC CGGCTGACGG GTCTCCTGCC TGCCCCGGGG ACCCGCCTGG ACCTGGTCCG
7381 CGACCTCGCC TGGCCGATGG CGTCGCGGGG GGTCGGCGCG GACGACCCCG ACGTGCTGCG
7441 CGCCGCGTGG GACGCCCGGG TCGGCCTCGA CGCCCAGCTC ACCCCGCAGC CCCTGGCGGT
7501 GACCGAGGCG GCGATCGCCG CGGTGCCCGG GGACCCGCAC CGGCGGGCGC TGTTCACCGC
7561 CGTCGAGATG ACAGCCACCG CGTTCGTCGA CGCGGTGCTG GCGGTGACCG CCACGGCGGG
7621 GGCGGCCCAG CGTCTCGCCG ACGACCCCGA CGTCGCCGCC GTCTCGTCG GGAGGTGCT
7681 GCGCCTGCAT CCGACGCGCG ACCTGGAACG GCGTACCGCC GGCACCGAGA CGGTGGTGGG
7741 CGAGCACACG GTCGCGGCGG GCGACGAGGT CGTCGTGGTG GTCGCCGCCG CCAACCGTGA
7801 CGCGGGGGTC TTCGCCGACC CGGACCGCCT CGACCCGGAC CGGGCCGACG CCGACCGGGC
7861 CCTGTCCGCC CAGCGCGGTC ACCCCGGCCG GTTGGAGGAG CTGGTGGTGG TCCTGACCAC
```

-continued

SEQ ID NO.2-Sequence Containing Downstream Megalomicin Modification Genes-KOS205-57-2.3B

```
 7921 CGCCGCACTG CGCAGCGTCG CCAAGGCGCT GCCCGGTCTC ACCGCCGGTG GCCCGGTCGT
 7981 CAGGCGACGT CGTTCACCGG TCCTGCGAGC CACCGCCCAC TGCCCGGTCG AACTCTGAGG
 8041 TGCCTGCGAT GCGCGTCGTC TTCTCCTCCA TGGCCAGCAA GAGCCACCTG TTCGGTCTCG
 8101 TTCCCCTCGC CTGGGCCTTC CGCGCGGCGG GCCACGAGGT ACGGGTCGTC GCCTCACCGG
 8161 CTCTCACCGA CGACATCACG GCGGCCGGAC TGACGGCCGT ACCGGTCGGC ACCGACGTCG
 8221 ACCTTGTCGA CTTCATGACC CACGCCGGGT ACGACATCAT CGACTACGTC CGCAGCCTGG
 8281 ACTTCAGCGA GCGGGACCCG GCCACCTCCA CCTGGGACCA CCTGCTCGGC ATGCAGACCG
 8341 TCCTCACCCC GACCTTCTAC GCCCTGATGA GCCCGGACTC GCTGGTCGAG GGCATGATCT
 8401 CCTTCTGTCG GTCGTGGCGA CCCGACTGGT CGTCTGGACC GCAGACCTTC GCCGCGTCGA
 8461 TCGCGGCGAC GGTGACCGGC GTGGCCCACG CCCGACTCCT GTGGGACCCC GACATCACGG
 8521 TACGGGCCCG GCAGAAGTTC CTCGGGCTGC TGCCCGGACA GCCCGCCGCC CACCGGGAGG
 8581 ACCCCCTCGC CGAGTGGCTC ACCTGGTCTG TGGAGAGGTT CGGCGGCCGG GTGCCGCAGG
 8641 ACGTCGAGGA GCTGGTGGTC GGGCAGTGGA CGATCGACCC CGCCCCGGTC GGGATGCGCC
 8701 TCGACACCGG GCTGAGGACG GTGGGCATGC GCTACGTCGA CTACAACGGC CCGTCGGTGG
 8761 TGCCGGACTG GCTGCACGAC GAGCCGACCC GCCGACGGGT CTGCCTCACC CTGGGCATCT
 8821 CCAGCCGGGA GAACAGCATC GGGCAGGTCT CCGTCGACGA CCTGTTGGGT GCGCTCGGTG
 8881 ACGTCGACGC CGAGATCATC GCGACAGTGG ACGAGCAGCA GCTCGAAGGC GTCGCCCACG
 8941 TCCCGGCCAA CATCCGTACG GTCGGGTTCG TCCCGATGCA CGCACTGCTG CCGACCTGCG
 9001 CGGCGACGGT GCACCACGGC GGTCCCGGCA GCTGGCACAC CGCCGCCATC CACGGCGTGC
 9061 CGCAGGTGAT CCTGCCCGAC GGCTGGGACA CCGGGGTCCG CGCCCAGCGG ACCGAGGACC
 9121 AGGGGGCGGG CATCGCCCTG CCGGTGCCCG AGCTGACCTC CGACCAGCTC CGCGAGGCGG
 9181 TGCGGCGGGT CCTGGACGAT CCCGCCTTCA CCGCCGGTGC GGCGCGGATG CGGGCCGACA
 9241 TGCTCGCCGA GCCGTCCCCC GCCGAGGTCG TCGACGTCTG TGCGGGGCTG GTCGGGGAAC
 9301 GGACCGCCGT CGGATGAGCA CCGACGCCAC CCACGTCCGG CTCGGCCGGT GCGCCCTGCT
 9361 GACCAGCCGG CTCTGGCTGG GTACGGCAGC CCTCGCCGGC CAGGACGACG CCGACGCAGT
 9421 ACGCCTGCTC GACCACGCCC GTTCCCGGGG CGTCAACTGC CTCGACACCG CCGACGACGA
 9481 CTCTGCGTCG ACCAGTGCCC AGGTCGCCGA GGAGTCGGTC GGCCGGTGGT TGGCCGGGGA
 9541 CACCGGTCGG CGGGAGGAGA CCGTCCTGTC GGTGACGGTG GGTGTCCCAC CGGGCGGGCA
 9601 GGTCGGCGGG GGCGGCCTCT CCGCCCGGCA GATCATCGCC TCCTGTGAGG GCTCCCTGCG
 9661 GCGTCTCGGT GTCGACCACG TCGACGTCCT TCACCTGCCC CGGGTGGACC GGGTGGAGCC
 9721 GTGGGACGAG GTCTGGCAGG CGGTGGACGC CCTCGTGGCC GCCGGAAAGG TCTGTTACGT
 9781 CGGGTCGTCG GGCTTCCCCG GATGGCACAT CGTCGCCGCC CAGGAGCACG CCGTCCGCCG
 9841 TCACCGCCTC GGCCTGGTGT CCCACCAGTG TCGGTACGAC CTGACGTCGC GCCATCCCGA
 9901 ACTGGAGGTC CTGCCCGCCG CGCAGGCGTA CGGGCTCGGG GTCTTCGCCA GGCCGACCCG
 9961 CCTCGGCGGT CTGCTCGGCG GCGACGGTCC GGGCGCCGCA GCCGCACGGG CGTCGGGACA
10021 GCCGACGGCA CTGCGCTCGG CGGTGGAGGC GTACGAGGTG TTCTGCAGAG ACCTCGGCGA
10081 GCACCCCGCC GAGGTCGCAC TGGCGTGGGT GCTGTCCCGG CCCGGTGTGG CGGGGGCGGT
10141 CGTCGGTGCG CGGACGCCCG GACGGCTCGA CTCCGCGCTC CGCGCCTGCG GCGTCGCCCT
```

-continued

SEQ ID NO.2-Sequence Containing Downstream Megalomicin Modification Genes-KOS205-57-2.3B

```
10201 CGGCGCGACG GAACTCACCG CCCTGGACGG GATCTTCCCC GGGGTCGCCG CAGCAGGGGC
10261 GGCCCCGGAG GCGTGGCTAC GGTGAGAGCC CGCCCCTGAC CTGCGGGAAC CCGTGTCGGT
10321 GCGGCGGGAC GGCCGCCGCG GTCCCCGCCC CGGTCAGCCG GTGGGGGTGA GCCGCAGCAG
10381 GTCCGGCGCC ACCGACTCGG CCACCTCCCC GACGTGGTCG GCGAGGTAGA AGTGCCCGCC
10441 CGGGAAGGTC CGGGTACGGC CGGGGACTAC CGAGTACGGC AGCCAGCGTT GGGCGTCCTC
10501 CACCGTCGTC AACGGGTCGG TGTCACCGCA GAGGGTGGTG ATGCCGGCCC GCAGCGGCGG
10561 CCCGGCCTGC CAGGCGTAGG AGCGCAGCAC CCGGTGGTCG GCCCGCAGCA CCGGCAGCGA
10621 CATGTCCAAC AGCCCCTGGT CGGCCAATGC GGCCTCGCTG ACCCCGAGCC TGCGCATCTG
10681 CTCGACGAGT CCGTCCTCGT CGGGCAGGTC GGTGCGCCGC TCGTGGACCC GGGGGCGGT
10741 CTGCCCGGAG ACGAACAACC GCAGCGGTCG CACCCCCGGA CGAGCCTCCA GGCGACGGGC
10801 GGTCTCGTAG GCGACCAGGG CGCCCATGCT GTGACCGAAC AGGGCGAACG GAACCTCGCC
10861 GACGAGGTCG CGCAGCACGG CCGCGACCTC GTCGGCGATC TCCCCGGCGG TGCCGAGAGC
10921 CCGCTCGTCA CGTCGGTCCT GCCGGCCCGG GTACTGCACC GCCCACACGT CGACCTCCGG
10981 GGCCAGTGCC CGGGCGAGGT CGAGGTACGA GTCGGCGGCG GCTCCCGCGT GCGGGAAGCA
11041 GTACAGCCGG GCCCGGTGTC CGTCGGCGGA CCCGAACCGC CGCAACCAGG TGTTCATCGG
11101 TGTCTCATCC GTTCGGTCGC ACCGGCAGGT GGTCGATGCC GCGCAGCAGG AGCGACCGCC
11161 GCCAGACAAC CTCGTCGGAG GGGAAGCCCA GCGACAGCTT CGGGAAGCGG TCGAACAGGG
11221 CCCCCAGGGC GACCTCTCCC TCCAGCTTGG CCAGCGGGCG GCCCATGCAG TAGTGGATGC
11281 CGTGCCCGAA GGTGAGGTGT CCCCGGCTGT CCCTGGTGAC GTCGAACCGG TCGGGGTCGG
11341 GGAACTGTCC CGGGTCGCGG TTGGCCGCCC CGTTGGCGAT CAGGACGGTG CTGTACGCCG
11401 GGATCGTCAC CCCGCCGATC TCCACCTCGG CGGTGGCGAA CCGGGTGGTG GTCTCCGGTG
11461 GGGCCTGGTA GCGCAGGATC TCCTCCACCG CTCCGGGCAG CAGTGCCGGG TCCTTCCGGA
11521 CCAGCGCGAG CTGGTCGGGG TGGGTCAGCA GCAGGTAGGT GCCGATCCCG ATGAGGCTCA
11581 CCGACGCCTC GAATCCCGCC AGCAGCAGCA CCAGCGCGAT GGAGGTGAGT TCGTCGCGGC
11641 TGAGCCGGTC GGCGTCGTCG TCCTGGACCC GGATCAGGGC CGAGAGCAGG TCGTTGCCGG
11701 GCTCGGTACG GCGGCGCTCG ACCAGGTCGA TGATGAAGGT GACGACCTCC TGGGCGGCCT
11761 GGCCGCGCTG CGCGGCGCGC TCGGGTTCCA TGACGAGGAT CTCCGAGCTC CACCGGCCGA
11821 AGTCGCCCCG GTCCTTCTCG TCCACCCCGA GCAGTTCGCA GATCACCTTG ATGGGCAGGG
11881 GATGGGCGAA CCGGTCGACG ATGTCGACCT CGTCGACGTC GCCGATCTCG TCGAGCAGTT
11941 GCGCGGTGAT CGCCTCGACC CGGGGACGCA TGGCCTCCAC CCGGCGGGCG GTGAACTCCT
12001 GGGAGACCAG CTTGCGCAGC CGGGTGTGGG TGGCGGGTC GCTGGTGCCC ATGTTGTTGA
12061 CGAAGTAGTG CCGTACGTCC TCGGGGAAGC CCAGGTAGGC GGGGAACTCC ACCTCCACCC
12121 CCGGGTACTT CTTCTTCGGG TCGCTGCTCA ACCGCAGGTC GCCCAGGGCG GTACGGGCCT
12181 CCTCGTAGCC GGTGATCAGC CAGGCGTCCT GGCCGAAGAA GCGCACCGGG GTCACCGGGG
12241 CCCGTTCGCG CAGCTCCGCA TAGGTCCGGT ACCAGTCGAC GTGGAAGGCG TCGCTCTCCA
12301 GATCGGGCAG TTTCATCACA CCACTTCCAG GTGGGGGAGG GGGAAGACGA GCTTGCCGCC
12361 GTTGGCGAGG AACTCCTGTT CCCGTTCGAG GAAGCCGTCG CGGTAGATCC AGGGCAGGAC
12421 GAGGAGCTGG TCGGGCGGC GGGACTTCGC CTCCTCCTCC GACACGATCG GGATCCCGGT
```

-continued

SEQ ID NO.2-Sequence Containing Downstream Megalomicin Modification Genes-KOS205-57-2.3B

```
12481 GCCCGGGGTG TACCGGCCGG ACTTCTCCGG GCTGACCTCC CCGATGCAGG GCAGGTCGTC
12541 CTCGGTGAGT CCGCAGTACT GCAGGATCAC GTTGCCCTTC GTCGAGGCGC CGTACCCCAG
12601 GGTCAGTTTG CCGGCGGCGC GCGACGTGGC GAGGAAGTCC AGCAGGTGGT CGCGTTGGCG
12661 CTCGGTGTTG CGGGCGAATG CCTCGTAGGG CGCCAGGGTG TCGAGCCGGG CGGCGGTCTC
12721 CTGGTCCCGG ATCTTCTGCA GCGCCGGCTC GTTCACCCGG TGGTCGCTGG TCTGCCGGGC
12781 CAGCACGGCA CAGAGGCTTC CGCCGTACAC GTCGGTGATC TCGGCGTCGA CCACCTTCAG
12841 CCCGGTGCGT TCGGCCATCC ACTCGATCTG CCGCAGGGCG TAGTACTCAA GGTGTTCGTG
12901 GCAGACGATG TCGTAGGCGC TGGCCTCCAG CATGGAGGGC AGGTAGCTCT GCTCCATCAG
12961 CCACAGGCCG TCGGGGCGA GGATGTCGTG GACGTCGCGC ATGAACTCCG TCGGCGCGGG
13021 CAGGTCGTAG AACATCGCGA TGGAGGTGAC GATCGCGGCG CGCCGGTCCC CGTAGCGCTC
13081 GGTGAACGCC TCGGCGGAGA AGAAGCCGGC GACGAGGTCG GCCTCCGGTG GGTACAGGTC
13141 GCGGAACTTC TCTCCCACCA GGTCGAACCC GACCAGCTTC GGCGGGTCGG GGAGGTAGCC
13201 CCGCAGCAGG GTGGAGTCGT TGCTGCCGAT GTCGACCACG AGGTCGTCGG GGCCGACCTC
13261 GCGCATGCCG CGCAGCTTGG CGACCTTGTC GTGCAGGTGG TTGATCATGA AGGGGCGGAT
13321 GCCGGACCGG TAGCCGTAAC CCTCGTTGTA CATCAGTCCG AAGTCGGGCG TCTCGCGCAG
13381 CTGGACCAGT CCGCAGCCGG GCGGCGCGCA GGTCACCAGT TCCAGCGGAA ACGTGGGGAC
13441 GACGTCGTCT GGGCTGTGCG GGAAGACCCC GGTGAGGGCC TGTTCTCCCA GATGCAGTAC
13501 TGATTCGAGA TCTTCATTTC CGCAGATACG GCATCTCGTT TCGGGCATCG CCTGAGTGTA
13561 GCGATCAAAA ACTGATATCG ATTGATGCGT GAGCCAGATC ACACGGAATT TCCGGCCTGT
13621 GGTGCGGGTG CAGGPATGTG TCGTGCGCG GATGCGTCC GCATCTCGGG CGGCGTCCAC
13681 CGACCCCCTG CGTCGGGGTC ACGAACCGCT CTCCACCTGC ACAGATGCTT CGCCTGCCGA
13741 CCTGCCGTGC CAAGGTTCGC GAGGTGCCTG CGGGGTCGAT GGCCCGCCGA ATACGGGGCA
13801 TCATTGATGG TCAAGCGACT ATGTATCGAG CTGGGGAGGT AATTGCGTCG GGGTGGAGTC
13861 CGACGTCAGT CGAGAATGCC GTTCGCCGAC CACCGGTGGT CGCCGCTCGG CTGTCGGTGC
13921 CGGTCCCTCA CACCATCGCC CGGGCGCGTA ACGCCTCCCA CCAGGGTCGG TTGTCGCGGT
13981 ACCAGCGGAC GGTGTCGGCG AGCCCCGCAC GGAAGTCGAC CCGGGGGGTG TACCCCAACT
14041 CGCGTCGGGC CTTCGAGCAG TCGAGTGAGT AGCGCCGGTC GTGGCCCTTG CGGTCCGAGA
14101 CGTGCCGCAC CCGGTCCCAG CCGGCGTCGC AGGCGGCGAG CAGCAGACCG GTCAGTTCCC
14161 GGTTGGACAG CTCCGTGCCC CCGCCGATGT GGTAGATCTC CCCGGCCCGG CCCCGCGTAC
14221 GGGCCAACTC GATCCCGTGG ACGTGGTCGT CGACGTGCAG CCAGTCCCGT ACGTTGCCAC
14281 CGTCGCCGTA GAGCGGCACC GTCTCCCCGT CGAGGAGTCG GGTGATGAAA AGGGGGATGA
14341 GCTTCTCCGG GAAGTGGTAC GGCCCGTACG TGTTGGAGCC CCGGGTCACC CGGACGTCGA
14401 GACCGTGCGT GTGGTGGTAC GACAGGGCGA CGAGATCACC ACCCGCCTTC GACGCCGAGT
14461 ACGGGGAACT GGGCTTGAGC GGGTGCGTCT CCGGCCACGA GCCGTGCTCG ATGGAGCCGT
14521 ACACCTCGTC GGTCGAGACG TGGACGAACG TCTCGACGCC CTGCTGGTGA GCCGCCTCGA
14581 TCAGGGTCTG GGTGCCGAGC ACGTTGGTAC GGACGAACGC CGCCCCGCCG TCGATCGACC
14641 TGTCGACGTG GGACTCGGCG GCGAAGTGGA CCACCTGGTC GTGCTCGCGG GCCAGCGCGG
14701 TCACCGTCGC GGCGTCGCAG ATGTCACCCT GGACGAACGT GTACCTCGGG TGGTCGCGCA
```

-continued

SEQ ID NO.2-Sequence Containing Downstream Megalomicin Modification Genes-KOS205-57-2.3B

```
14761 GGCCCGCCAG GTTCTCCGGG TTACCGGCGT AGGTGAGGGC GTCCAGGACC GTGACCCGTA
14821 CGTCGGTCGG CCCGTCCGGG CCGAGCAGGG TACGGACGTA GTGCGAACCG ATGAATCCGG
14881 CACCGCCGGT GACCAGGAGT CGAGTCGTCA TGACGAGATC TGCACCTTGC TGTGATCGCC
14941 GAGCACGAAC CGGTGGGCGG CGGGGTTGCG CGGCGCGGGG GTGACCTCCA CGCCACGTCC
15001 GATCAGTGAC GCCTCGACCC GGCGGACGCC GGTGAGTGCC GAGTCCCGCA ACACGATCGA
15061 GTACTCGATC TCGGTGTCCT CGATCCGGCA GCACTCGCCG ATCGCTGTGA ACGGCCCGAC
15121 GTAGGAGTCG ACGACCTCCG TCGAGGCGCC GATGACCGCC GGGCCGACGA TACGGCTTCC
15181 GCTGATCCGC GCGCCCCGAT CGATCCGTAC CCGGCCGATG ATCTCGCTGG TGGCGTCGAC
15241 CGTACCGGCC ACCCGGGTCT CGATGGTCTC CAGCACGGAA CGGTTCACCT CCAGCATGTC
15301 GGTCACGTTG CCGGTGTCCT TCCAGTATCC GGAGATGATC GTCGACCGGA CGTCGCACTC
15361 GCGGTCGATG AGCCACTGGA TGGCGTGAGT GATCTCCAGT TCCCCCCGCT CGGACGGGGT
15421 GATGACCCGT ACCGCCTCGT GGACCACCGG CGTGAACAGG TAGACCCCGA CCAGGGCGAG
15481 GTCGCTCTTG GCGTGCTGTG GCTTCTCCTC CAGGCTGACC ACCCGGCCGT CGACGAGTTC
15541 GGCGACCCCG AAGTGCCGGG GTCCGCCAC GTGGGTCAGC AGGATGTGCG CGTCGGGGCG
15601 GGCCTGCCGG AAGTCGTCGA CCAGGTCGCG GATCCCGCCG ACGATGAAGT TGTCGCCCAG
15661 GTACATGACG AAGTCGTCGT CACCGAGGTA GTCGCGGGCG ATCAGGACGG CGTGGGCGAG
15721 GCCCAGCGGC GCGTGCTGGC GGATGTAGGT CACTGAGATG CCGAACTCCG AGCCGTCCCC
15781 CACGGCGGCC ATGATCTCGT CGGCGGTGTC ACCCACGATG ATGCCGACGT CGCGGATGCC
15841 GGACTCAGCG ATGGCCTCCA GCCCGTAGAA GAGCACCGGC TTGTTGGCCA CCGGCACCAA
15901 CTGCTTGGCG GACGTGTGCG TGATGGGTCG TAGGCGGGTA CCCGCTCCGC CCGACAGGAC
15961 AAGCGCCTTC ATGTGACCCC CCGGGGCACC AGAGATGAGC CGTCCACTGT CGGAACCAGG
16021 TTGGCGGCGA CGGCTACAGG ACAGGTCGAG CCTCGGCTGA GGGACCACCC GCACCAGAGG
16081 GGGAGGCGTG CGGCGGCGCT ACGCGCCGCG TGGGGGTGGG CCGGGTAGGG ACGTGCCGGG
16141 TGGGGACGTG CAGCGGCCCG GCGTGCGGAC GACCCGGCGG CCGGGCACCC GGCATCCCCA
16201 GGAACTGCGG CGGCGGGCCG GGGTGGCGGC GCGATGCGGC ACGGGGGCGT CCGGCGGTCC
16261 GGGCGAGCGC GACACCACGT CGTACGCGGT CGCGGCTGGT GGGTGGTGGC CGGGGGCCTT
16321 GTCGCCCTAC TTCTTGTCGC GGCGACCGGT GGCGAGGATC CGCTCCCGCC GGGGCGGGAC
16381 GACGTCGGCG GTCGACGTCT CGTCCGGCCC GGCCGGGTCG GTGGTGTCCT TCTTGGCCAG
16441 CTGCTGGAGG CGGAGCTGAC CGCAGGCGGC TTCGATGTCC TGGCCCTGGG TGTCCCGGAC
16501 GGTGACGTTG ACCCCGGCGG AGTCCAACTC GCGCGGACG GTGCTCAGTC GCCGGTCACT
16561 GACCCGCTGG AAGAGCGGAC CGCCCAGGAC CGGATTCCAC CGCATCAGGT TGATCCGAGC
16621 CGGTCGACCT GCGAAGAACT GGATCAGACG GGTGACGTCG TCGTCGGAGT CGTTCACATT
16681 GGGAAGCAGG AGGTAAACGA AGGTGACGAT CCGACCGTGC CGCTCCGCCC ACGACAACGC
16741 ACCCTCGACG ACCTCGTTGA TGTCGTGATT GCGTGATCCC GGGATCAGTT CGGTCCGCGA
16801 CTCCTGCGTG GTCGCGTGCA GGGAAATGGT CAGATTGATC TTGATGTGCT CTTCACGCAG
16861 GCGCTTCAGC GACTTCGGGA TACCGATCGT GGAGATGGTG ATCCCACTGG TCTTGAAGCC
16921 GAGCCCGCGC CGTTCGCGGA GAATGCGAAT GGAGCCCATG ACGTTGTCGT AGTTGTGCAG
16981 GGGCTCGCCG ATGCCCATGA ACACGAGCCT GTTGACGCCG GGCCCGAGCG CCAGCACCTG
```

-continued

SEQ ID NO.2-Sequence Containing Downstream Megalomicin Modification Genes-KOS205-57-2.3B

```
17041 CTGCACGATC TCGCCCGGTA GCAGGTGTCG CTTGAGGCCG TCGCGGCCCG ACGCGCAGAA

17101 CTGGCACGCG AAGGCGCACC CCGCCTGAGA CGAGACGCAG GCGGTGTAGC CGTCGTGGCG

17161 ACGGATCCGC ACCGTCTCGA TGAAATTGCC GTCGACCAGC TCGAACAGGA ACTTTGTCGT

17221 CTGGCTTCCC CTGGTGCGAC TGCGCTCGGC GAGGGTCGAC GAGAGGTCGT CGAGTTGCCC

17281 GTAGTGCTTC AGCGTGTGGG CCGAGTCTTT GCGCTGCCGA TAAAGCTTGT CGAAGATGTC

17341 GGCTGCTTGC CGTTCGCCGC CGACGCGCTC CGCGAGCTCG GAGAACGACA GGTCGAAGAC

17401 CGACGGCGCG ACGGGTCGTC GTCGCCGAAT GGGTAGACCC ACGACCTGGG GCGAAGCTGA

17461 CATAGTCACC ACCCTATCAC GGTGCAAGAG ACGTCAATTC GTCAAGTGAC CACAGAGGAG

17521 CCTGACGATG GACGATGCTC TCGTGTCTTC GCCATATAGC CGTTGAGCTG CCAATTCACG

17581 AACGCGCAGC GGGCGC
```

What is claimed is:

1. An isolated, purified, or recombinant nucleic acid comprising a polyketide modifying gene, wherein said gene encodes a MegL and/or a MegM polyketide modifying enzyme, and wherein said nucleic acid optionally comprises a polyketide modifying gene encoding a polyketide modifying enzyme selected from the group consisting of MegR, MegCIV, MegCV, MegBVI, and MegBIII, wherein MegR has the sequence encoded by nucleotides 52-942 of SEQ ID NO:1, MegCIV has the sequence encoded by nucleotides 3893-5098 of SEQ ID NO:1, MegCV has the sequence encoded by nucleotides 2386-3855 of SEQ ID NO:1, MegBVI has the sequence encoded by nucleotides 5095-6558 of SEQ ID NO:1, MegBIII has the sequence encoded by nucleotides 12316-13548 of SEQ ID NO:1, MegL has the sequence encoded by nucleotides 14908-15972 of SEQ ID NO:1, and MegM has the sequence encoded by nucleotides 13928-14911 of SEQ ID NO:1, and wherein the nucleic acid does not comprise the S. erythraea Meg CII gene (nucleotides 6962-8038 of SEQ ID NO:1).

2. An isolated, purified, or recombinant nucleic acid comprising a polyketide modifying gene, wherein said gene encodes a MegL and/or a MegM polyketide modifying enzyme, and wherein said nucleic acid optionally comprises a polyketide modifying gene encoding a polyketide modifying enzyme selected from the group consisting of MegR, MegCIV, MegCV, MegBVI, and MegBIII, wherein MegR has the sequence encoded by nucleotides 52-942 of SEQ ID NO:1, MegCIV has the sequence encoded by nucleotides 3893-5098 of SEQ ID NO:1, MegCV has the sequence encoded by nucleotides 2386-3855 of SEQ ID NO:1, MegBVI has the sequence encoded by nucleotides 5095-6558 of SEQ ID NO:1, MegBIII has the sequence encoded by nucleotides 12316-13548 of SEQ ID NO:1, MegL has the sequence encoded by nucleotides 14908-15972 of SEQ ID NO:1, and MegM has the sequence encoded by nucleotides 13928-14911 of SEQ ID NO:1, and wherein the nucleic acid does not comprise the S. erythraea MegBIII gene (nucleotides 12316-13548 of SEQ ID NO:1).

3. An isolated, purified, or recombinant nucleic acid comprising a polyketide modifying gene, wherein said gene encodes a polyketide modifying enzyme selected from the group consisting of MegR, MegCIV, MegCV, MegBVI, MegBIII, MegL, and MegM, wherein MegR has the sequence encoded by nucleotides 52-942 of SEQ ID NO:1, MegCIV has the sequence encoded by nucleotides 3893-5098 of SEQ ID NO:1, MegCV has the sequence encoded by nucleotides 2386-3855 of SEQ ID NO:1, MegBVI has the sequence encoded by nucleotides 5095-6558 of SEQ ID NO:1, MegBIII has the sequence encoded by nucleotides 12316-13548 of SEQ ID NO:1, MegL has the sequence encoded by nucleotides 14908-15972 of SEQ ID NO:1, and MegM has the sequence encoded by nucleotides 13928-14911 of SEQ ID NO:1, and wherein the nucleic acid does not comprise a gene encoding MegY or a gene encoding MegCII.

* * * * *

SEQUENCE LISTING

```
<160> NUMBER OF SEQ ID NOS: 24

<210> SEQ ID NO 1
<211> LENGTH: 9024
<212> TYPE: DNA
<213> ORGANISM: Micromonospora megalomicea
<220> FEATURE:
<221> NAME/KEY: misc_feature
<222> LOCATION: (0)...(0)
<223> OTHER INFORMATION: Genomic DNA
<220> FEATURE:
<221> NAME/KEY: misc_feature
<222> LOCATION: (1)...(9021)
<223> OTHER INFORMATION: n = A,T,C, G, or none

<400> SEQUENCE: 1
gcgcgcttcg atcaccatgg atcgcttaat gtccggttcc attgcttttc gatgggggat    60
gtagtgcaat tgcaaaatcc ggagaccgtg gtaagcctcg gagtcctggg tccgctgttc   120
gtcagttccc catcgccgcg aaagacgccg acggcacgga aaccgagaaa tgttctcgca   180
atgctcctcg tccacgccga ccaggtcgtt ccggtctccg tcctggtctc cgagctctgg   240
gacgacgagc cgccggtcag caggctcacc accctccaga cgtacattct caatctgcgc   300
aagatgttcg tggcggtcac cggtctgccc gccgaggagg tcacccggag tctgctcatc   360
acccgggccg gcggctatct gctccgcggt gaccggatcg ccctcgacgt ccgggagtac   420
cagcgtctga tgtcgccgg ctgcgccgcg ctcggcctcg gcgacgacgt gacaggcacc   480
cgcagactca ccgaggcgct cggcctctgg cgcgggcccg cgctcgtcga cgtcccgctg   540
ggtcgggtgc tggagtcgaa gcgtcgcgaa ctggaggagt cctggctcat ggccagcgaa   600
tacctggtcg gcgcgaagtt gcgtcagggg atgtaccggg aggccctcat cgagctgacc   660
gcgctcaccg cggagaatcc gctgcacgag gggctccagg cgcagtacat gcgggcgctg   720
catctcagtg gtcgacgcgc gcaggcgttg gaggtcttcc accggttgcg tcgcaacctc   780
gtcgacgaac tgggtctgga accggagccg caggtgcaac ggatccacca ggcgatcctg   840
aacgccgaga ccgacttcga ggacgatctg cgcgtcatcc gtccgtttcc gtccgaggtc   900
```

```
gccgccacga gttggggtcg ggtccgggtc cgggcgagct gaccgattac cgcgtacggc      960
gacaccctga gccgacaatc aacgacattg gcgaaaatcg acatctgtgc cggggggga     1020
cgggttggac gacgaacggt ggggagaacc atgaccacta tcgaacagat cccgagcatg     1080
gccgaggagg ccgttctgct cgactggctg gcggtgatgc gcgacaggca cccggtctgg     1140
caggaccagt acggcgtctg gcacatcttc cgccacagtg acgtacgcga ggtcctccgc     1200
gacaccgcca ccttctcctc cgaccccacc cgcgtcatcg agggggccga cccgacgccg     1260
gggatgatcc acgagatcga cccgccggag caccgggccc tgcgcaaggt cgtcagcagc     1320
gccttcaccc cgcgtacgat cgccgacctc gaaccgcgca tccgggaggt gacccggtcg     1380
ctgctggccg acgccggtga ccgcttcgac ctggtcgagg cgctcgcctt cccgctgccg     1440
gtcacgatcg tcgccgagct gctggggctg cccggatgg accacaagca gttcggtgac     1500
tggtccggcg ccctggtcga catccagatg gacgacccga ccgatccggc cctggtcgaa     1560
cgcatcatgc aggtgctgaa cccgctcacc tcctacctgc tcgacaggtg tcgggaacgg     1620
cgggccgacc ccgggacga cctgatctcc cggctggtgc tggccgaggt cgacgggcgc     1680
accctcgacg acgtggaggc ggccaacttc tccacagcgt tgctgctcgc ggggcacatc     1740
accaccaccg tcctgctggg caacatcgtc cgcaccctcg acgagcaccc ggagtactgg     1800
acggccgccg ccgaggaccc gggtctgatc gcgccgatca tcgaggaggt gttgcgtttc     1860
cgccccccgt tcccccagat gcagcgcacc acgaccaggg ccaccaccgt cggtggggtc     1920
gagatcccgg ccgacgtcat ggtcaacacc tgggtgctct cggccaaccg cgatcccctg     1980
gcgcatcccg acccggacac gttcgacccg tcccgcaaga tcggtggtgc cgcgcagctc     2040
tccttcgggc acggcgtgca cttctgtctc ggtgccccgc tggcgcgcct ggagaaccag     2100
gtcgccctgg aggagatcat cgcccggtac ggtcgactgg ccgtcgaccg cgacgacgac     2160
acgctgcgtc acttcgacca gatcgtcctc ggcaccccggc acctcccggt gctggcggcg     2220
gtcacccccgg ccgagtccgc ctgaacccct tgcgctccga cgcggcggnn nnnnnnnnn     2280
nnnnnnnnnn nnnnnnnnnn nnnnnnnnnn nnnnnnnnnn nnnnnnnnnn nnnnnnnnnn     2340
nnnncnncnt cncnccnccg ccgcgccggg gcgggtcgac gccgttcaga cggcgcggat     2400
caggccccga tgctgatccc acccgtcggc gacgtcccgt tcgagttggt tgagccgggc     2460
ggtcaccgac tggtcgaaac cgtcgaggaa gaactcgtcc cccggctgcg gatcgatgct     2520
gcggcccgac gtgacgaagt cgtggacgac cgagtgcagg ctccggtccg gggtgacccg     2580
gccggcgacg tagcgggtgg cccccgccag cccgggaaa ccggcctccc ggtacaggta     2640
gacgtctccg agcaggtcga tctgcaccgc cacctgcgga tgggcggtcg ggcgcatcgt     2700
ttccggccgg atccgcaaca gctgggcgtc gacaccccga cgcaggctct ccaacgcgta     2760
acccaggtcg gtctgcatgc ccggggtccg ctcggcggcg tagtcgacga accgggcgag     2820
gccctcccgc aactcggtcc gttcgccctc ggacaacctg ccgtcgtccc gaccgctgta     2880
gtcctcgcgg acggtgacga agtcgagcgg ccggtgcggg ctggactcgt tgagttcggc     2940
gatgaagtcg accaggtcga tgaggcggtt ggccgccc gcaggatga tgtggttgag     3000
gccgagccgg accggtgccg cccgttcggc gcgcatccgc aggaagtccc ggaggttctt     3060
cctgacccgt tcgaaggcgc cacgcttgcc ggtggtggcc tggtactcgt cgttgttcag     3120
cccgtacagg gaggtacgga ccgcgccgag gtcccacagg ccgggctggc ggcgcagcgt     3180
ctgttcggtg agggcgaagg cgttggtgta gacggtcagg gcgaagcccc gccgggcggc     3240
gtgcgacacc aacgccccga tacccgggtt ggtcaacggt tccaggccgc cggagaggta     3300
```

```
catcgccgtc gggttctccg acggcacctc gtcgatgacc gaggtgagga tctcgttgcc   3360
gggcaccacc gactccgcgt cgtacttggc acctgtcacc cgtacgcaga agtgacagcg   3420
gaacatgcac gtcgggccgg ggtagagccc gacgctgtac gggaaggcgg gctcccgccg   3480
taccgcagcc tccaacgcgc cggcggcgtt cagcggcctg atcgtgttgc tccagtactt   3540
gcccgccggg ccctgctcca ccgccgtgcc cagctgcggg atgcgatcga acaggtcgag   3600
cagctcgccg aacccggccc ggtccaggtc gaaccgacgg cgcatctgct ccaacgggt   3660 gaacggcgag gcgccgtagt gggcggtgag ttcggcgagc cggaccgcct gtcgttcggc   3720
ggtgtcggat gcggcaccgg tgaggcgggt gacctcggcg ctgagcgccc gcaccacggc   3780
cggccggtcg gcgtcgggtc gtgccgcgtc cgcgatctcc gtcggtacgg cggtcgccgt   3840
aggagtggtc ttcatcgacg tgcgaaccct tctggcgtct gtggtgcgag gatcacgaac   3900
cgttgcgttt ccgcttgtcc cactccgcgt tgatcaacgc accgctggtg gtggcgagtc   3960
ggatgacgtc gcacacccgg cggatgtcct cactggacac cgaggggccg gtcgggaggg   4020
cgagcacccg ttcggcgagc cactcggtct gtgtcagccg cagcggtggc tccgtgcggt   4080
agggcgtcat ctggtggcag gcgggggaga agtagggctg tgcgacgacc ttctccgcgc   4140
gcaggatcgc ctgcagccgg tcacggtcga tgccggtggc ggtgccgtcc accaggatga   4200
tcacgtactg gtagttgctc tcctcgtcgg gcggagcga gtgcacggtg acgccgcgta   4260
cgtcgcgcag ctcgctggtg tagagcgcgt ggttgacccg gttgtgctcc ctggtctcgg   4320
cgaacgcgtc gagggaggtg agccccatgg ccgcggcgca ctcgctcatc ttgccgttgg   4380
tgccgatctc ggtgaccacc ttgtccgggc cgatgccgaa gttgtgcatg cccggatcc   4440 gttcggccag caggccgtcg tcggtgacca ccgccccgcc ctcgaaggcg gtgaccgcct   4500
tggtggcgtg gaagctgaac acctcggcgt caccggatcc gcccaccgga cgtccacccg   4560
tcgtgcagcc cagggcgtgg gcggcgtcga agaagagctt gacctggtgg tcggcggcga   4620
tcttcgccag cgcctccaca ggtgctggtc ggccccacag gtgtacgccg acgatcgcgc   4680
cggtctgcgg ggtgacgagc gcggcgacgt ggtccgggtc gaccagaccg gtcgccgggt   4740
cgacgtcgca gaacaccggt gtgagtccga gccagctcgc cgcgtgcgcg gtggccgcga   4800
aggtcattga cggcatgatc acttcaccgg tgacgtcacc ggcccgcagc accagttcca   4860
gggcgacggt ggcgttgcag gtggcgatgc agtgccgtac cccgaccagg tcggcgaccc   4920
gggcctcgaa ctcccgcacc aggggcccgc cgttggtgag ccagttgttg ttcagggcc   4980 actccaggcg ggccaggaac cgctgccggt cgccgatcgt cggccggccc acgtgcaggg   5040
ggtgcaggaa cgcctcggga ccgccgaaga tcgccagatc ggtcggtacg cgcttcacgc   5100
cgtcgcccgg ttgtagacgg cggacgcgca ggcgacgagg ctgcgcagct ggatgttgac   5160
gtagtggctg tgcgcgagca gttcggtgat ctggccgaag gtcatccacc ggtggtcggg   5220
ggcaccgccg tcgtcgaagt ccgcgggcac ctcgacgagc atgtaccggt tctcgttgcg   5280
gtagaaccgc ccaccctcct cggagtgcca ggcgtcgtag cggatctggg tacgcgggac   5340
gtccagcacg tagtcgaggt aggtcgggcg gtgttcctcg ggcacgtcgg tgtagttgtc   5400
cggctgacag tgcaccgtcg ccgccaactc ggcgacgtcg tggccacccg cctcggtgcg   5460
caggtgcacg agcgcgtgga gggtgccgtc gatctccttg accaggaggg cgagcatgcc   5520
gtggttggcg ggggagagca gcggttgcat ccaggacctc acctcgcggt gactggtcgt   5580
cacggagacg ccgaagatgc tgaagtactt cttgtcctcg tgttcgatgc cgtcgtcgcg   5640
```

```
ccggatccac ccgctgcggt cgatgtcggc caacggccgg gtgcgttgga cgaactcacg   5700
tgtggtgcgt acgtccgaga tccagctcag cagggtgttc atgttgtgga ccggggtgcc   5760
cgccccgacg aaggaacgca gcagtcgggt ctcgaaggac ccctgggca gtccgtccag    5820 tacccggccg acggccccgg cttccaccct ggtcggtatg caggccagca cggaccgcag   5880
gtccatgttc accacgttgt cgtagcggag catcgcccgc agctgggcga gggtgagcca   5940
cctgcagttc gggtgctcgg gcgggtcctc gaagacctcg accaccatgt tgcggttgcg   6000
tttgcgcagg aaccaggaac cctgctcgga ctggaggacg tcgacgagga tccggtgggg   6060
gcgggtcccg tcgaagtact cgatgaactg gacgcgggat ccgttgtgga ccctcatgta   6120
gttgctgcgg gtggcctgca gggtcggcga gagctggacg gcgttgatgt tgccaggttc   6180
ggccttggcc tgcaccagag cgtgcagtac gccgtcgaac tcccgcacga tcagaccgag   6240
gaacccgatc tcgggttgga cgatgatggg ttggatccag tcccgtcgcc atccgaagtt   6300
ggtccggacg tgcaggccct cgatggagaa gaagcgcccg gagtcgtgcg ccagccgacc   6360
gtcctccggg tggaacgacc agcgttccat ggtgctgaag ggcactcggt gcacctcgag   6420
ccgatgctcg gcgcgcggt gggccaacca gtcgtggacg tcgtcggtgg cggtgggagg   6480
tccgccgtgc cgagtcagga acgtattgc cgattgtgtg gattccggag tcgcatgacc    6540
gttgacccga tccccatac gcctctcccg tgatgtcgtg ggcggtccgt gcggtaccgc    6600
ccggactgac attcgtcgat caagaccccg cccagtgtag ggctccgccc gcgacgggag   6660
aaggtccgtc gaacaacttc cgggtgaccg gtcgccggcg tcggtgaaac gggcgtcgga   6720
gcacccgatc attgctgtcg gtgaacttcc taactgtcgg cgcgcacatc tttctgaccg   6780
gtgtgttccg tggtatgacg cgttcccggc ccgtctggaa ctgtgcgtgg gactgaccgg   6840
ttgcggcgtg ttttcgcccg tttccgaact gcggattcgt cgatcgcgca ggtgggagcg   6900
ggtggctgac cgggatgatc tgcaatcatg gcgctcaatg acgatctctt gtagcatggt   6960
ccgcgccgag ggtccgacag gcccgaaacg cccggcatcc agcctgttcg acgacgtcga   7020
catcaccgtg caagccgcga tgacaccgac accacgccat gctggtgccg cactggaagg   7080
gtggcgcgat caggaaaatg gccgtgtcac tagacagacg ccaaacagct gtccgggcct   7140
gcggaaacag catcgatctg cgtcagccgt tcattgcccc ggcggcaccg ccttggaaat   7200
ccgtgccacc ggtcgtccgc agtgacgatc gcggacccgg gtttcgagac agcaggtagt   7260
aggcgatgca ggcgtttcgt ctcgcgccgg acgcgtcgca ctaggtggaa tccgtcacag   7320
tcttcaatcc gggagcgttc tatggcagtt ggcgatcgaa ggcggctggg ccgggagttg   7380
cagatggccc ggggtctcta ctgggggttc ggtgccaacg gcgatctgta ctcgatgctc   7440
ctgtccggac gggacgacga cccctggacc tggtacgaac ggttgcgggc cgccggacgg   7500
ggaccgtacg ccagtcgggc cggaacgtgg gtggtcggtg accaccggac cgccgccgag   7560
gtgctcgccc atccgggctt cacccacggc ccgcccgacg ctgccggtg gatgcaggtg    7620 gcccactgcc cggcggcctc ctgggccggc cccttccggg agttctacgc ccgcaccgag   7680
gacgcggcgt cggtgacagt ggacgccgac tggctccagc agcggtgcgc caggctggtg   7740
accgagctgg ggtcgcgctt cgatctcgtg aacgacttcg cccgggaggt cccggtgctg   7800
gcgctcggta ccgcgcccgc actcaagggc gtggaccccg accgtctccg gtcctggacc   7860
tcggcgaccc gggtatgcct ggacgcccag gtcagcccgc aacagctcgc ggtgaccgaa   7920
caggcgctga ccgccctcga cgagatcgac gcggtcaccg gcggtcggga cgccgcggtc   7980
ctggtggggg tggtggcgga gctggcggcc aacacggtgg gcaacgccgt cctggccgtc   8040
```

```
accgagcttc ccgaactggc ggcacgactt gccgacgacc cggagaccgc gacccgtgtg    8100
gtgacggagg tgtcgcggac gagtcccggc gtccacctgg aacgccgcac cgccgcgtcg    8160
gaccgccggg tgggcgggt  cgacgtcccg accggtggcg aggtgacagt ggtcgtcgcc    8220
gcggcgaacc gtgatcccga ggtcttcacc gatcccgacc ggttcgacgt ggaccgtggc    8280
ggcgacgccg agatcctgtc gtcccggccc ggctcgcccc gcaccgacct cgacgccctg    8340
gtggccaccc tggccacggc ggcgctgcgg gccgccgcgc cggtgttgcc ccggctgtcc    8400
cgttccgggc cggtgatcag acgacgtcgg tcacccgtcg cccgtggtct cagccgttgc    8460
ccggtcgagc tgtagaggaa gaacgatgcg cgtcgtgttt tcatcgatgg ctgtcaacag    8520
ccatctgttc gggctggtcc cgctcgcaag cgccttccag gcggccggac acgaggtacg    8580
ggtcgtcgcc tcgccggccc tgaccgacga cgtcaccggt gccggtctga ccgccgtgcc    8640
cgtcggtgac gacgtggaac ttgtggagtg gcacgcccac gcgggccagg acatcgtcga    8700
gtacatgcgg accctcgact gggtcgacca gagccacacc accatgtcct gggacgacct    8760
cctgggcatg cagaccacct tcaccccgac cttcttcgcc ctgatgagcc ccgactcgct    8820
catcgacggg atggtcgagt ctgccgctc  ctggcgtccc gacctgatcg tctgggagcc    8880
gctgaccttc gccgccccga tcgcggcccg ggtcaccgga accccgcacg cccggatgct    8940
gtggggtccg gacgtcgcca cccgggcccg gcagagcttc ctgcgactgc tggcccacca    9000
ggaggtggag caccgggagg atcc                                          9024

<210> SEQ ID NO 2
<211> LENGTH: 17596
<212> TYPE: DNA
<213> ORGANISM: Micromonospora Megalomicea
<220> FEATURE:
<221> NAME/KEY: misc_feature
<222> LOCATION: (0)...(0)
<223> OTHER INFORMATION: Genomic DNA

<400> SEQUENCE: 2
ccgcgctcgc cgaggcgtac acccgggggg tggaggtcga ctggcgtacc gcagtgggtg      60
agggacgccc ggtcgacctg ccggtctacc cgttccaacg acagaacttc tggctcccgg     120 tcccctggg  ccgggtcccc gacaccggcg acgagtggcg ttaccagctc gcctggcacc     180
ccgtcgacct cgggcggtcc tcctggccg  acgggtcct  ggtggtgacc ggagcggcag     240 taccccggc  ctggacggac gtggtccgcg acggcctgga acagcgcggg gcgaccgtcg     300
tgttgtgcac cgcgcagtcg cgcgcccgga tcggcgccgc actcgacgcc gtcgacggca     360 ccgcccgtc  cactgtggtc tctctgctcg cgctcgccga gggcggtgct gtcgacgacc     420
ccagcctgga caccctcgcg ttggtccagg cgctcggcgc agccgggatc gacgtccccc     480
tgtggctggt gaccagggac gccgccgccg tgaccgtcgg agacgacgtc gatccggccc     540
aggccatggt cggtgggctc ggccgggtgg tgggcgtgga gtcccccgcc cggtggggtg     600
gcctggtgga cctgcgcgag gccgacgccg actcggcccg gtcgctggcc gccatactgg     660
ccgacccgcg cggcgaggag cagttcgcga tccggcccga cggcgtcacc gtcgcccgtc     720
tcgtcccggc accggcccgc gcggcgggta cccggtggac gccgcgcggg accgtcctgg     780
tcaccggcgg caccggcggc atcggcgcgc acctggcccg ctggctcgcc ggtgcgggcg     840
ccgagcacct ggtgctgctc aacaggcggg gagcggaggc ggccggtgcc gccgacctgc     900
gtgacgaact ggtcgcgctc ggcacgggag tcaccatcac ggcctgcgac gtcgccgacc     960
```

```
gcgaccggtt ggcggccgtc ctcgacgccg cacgggcgca gggacgggtg gtcacgcgg   1020 tgttccacgc cgccgggatc tcccggttcca cagcggtaca ggagctgacc gagagcgagt  1080
tcaccgagat caccgacgcg aaggtgcggg gtacggcgaa cctggccgaa ctctgtcccg   1140
agctggacgc cctcgtgctg ttctcctcga acgcggcggt gtgggcagc ccggggctgg    1200 cctcctacgc ggcgggcaac gccttcctcg acgccttcgc ccgtcgtggt cggcgcagtg   1260
ggctgccggt cacctcgatc gcctgggtc tgtgggccgg gcagaacatg gccggtaccg    1320
agggcggcga ctacctgcgc agccagggcc tgcgcgccat ggacccgcag cgggcgatcg   1380
aggagctgcg gaccaccctg gacgccgggg acccgtgggt gtcggtggtg gacctggacc   1440
gggagcggtt cgtcgaactg ttcaccgccg cccgccgccg gccctcttc gacgaactcg    1500 gtggggtccg cgccggggcc gaggagaccg gtcaggaatc ggatctcgcc cggcggctgg   1560
cgtcgatgcc ggaggccgaa cgtcacgagc atgtcgcccg gctggtccga ccgaggtgg    1620 cagcggtgct gggccacggc acgccgacg tgatcgagcg tgacgtcgcc ttccgtgacc    1680
tgggattcga ctccatgacc gccgtcgacc tgcggaaccg gctcgcggcg gtgaccgggg   1740
tccgggtggc cacgaccatc gtcttcgacc acccgacagt ggaccgcctc accgcgcact   1800
acctggaacg actcgtcggt gagccggagg cgacgacccc ggctgcggcg gtcgtcccgc   1860
aggcacccgg ggaggccgac gagccgatcg cgatcgtcgg gatggcctgc cgcctcgccg   1920
gtggagtgcg taccccgac cagttgtggg acttcatcgt cgccgacggc gacgcggtca    1980
ccgagatgcc gtcggaccgg tcctgggacc tcgacgcgct gttcgacccg gaccccgagc   2040
ggcacggcac cagctactcc cggcacggcg cgttcctgga cggggcggcc gacttcgacg   2100
cggcgttctt cgggatctcg ccgcgtgagg cgttggcgat ggatccgcag cagcggcagg   2160
tcctggagac gacgtgggag ctgttcgaga acgccggcat cgacccgcac tccctgcgcg   2220
gtacggacac cggtgtcttc ctcggcgctg cgtaccaggg gtacggccag aacgcgcagg   2280
tgccgaagga gagtgagggt tacctgctca ccggtggttc ctcggcggtc gcctccggtc   2340
ggatcgcgta cgtgttgggg ttggagggc cggcgatcac tgtggacacg gcgtgttcgt    2400
cgtcgcttgt ggcgttgcac gtggcggccg ggtcgctgcg atcgggtgac tgtgggctcg   2460
cggtggcggg tgggggtgtcg gtgatggccg gtccggaggt gttcaccgag ttctccaggc   2520
agggcgcgct ggccccgac ggtcggtgca agcccttctc cgaccaggcc gacgggttcg    2580
gattcgccga gggcgtcgct gtggtgctcc tgcagcggtt gtcggtggcg gtgcgggagg   2640
ggcgtcgggt gttgggtgtg gtggtgggtt cggcggtgaa tcaggatggg gcgagtaatg   2700
ggttggcggc gccgtcgggg gtggcgcagc agcgggtgat tcggcgggcg tggggtcgtg   2760
cgggtgtgtc gggtgggggat gtgggtgtgg tggaggcgca tgggacgggg acgcggttgg   2820
gggatccggt ggagttgggg gcgttgttgg ggacgtatgg ggtgggtcgg ggtggggtgg   2880
gtccggtggt ggtggggttcg gtgaaggcga atgtgggtca tgtgcaggcg gcggcgggtg   2940
tggtgggtgt gatcaaggtg gtgttggggt tgggtcgggg gttggtgggt ccgatggtgt   3000
gtcggggtgg gttgtcgggg ttggtggatt ggtcgtcggg tgggttggtg gtggcggatg   3060
gggtgcgggg gtggccggtg ggtgtggatg gggtgcgtcg gggtggggtg tcggcgtttg   3120
gggtgtcgga gacgaatgct catgtggtgg tggcggaggc gccggggtcg gtggtggggg   3180
cggaacggcc ggtggagggg tcgtcgcggg ggttggtggg ggtggctggt ggtgtggtgc   3240
cggtggtgct gtcggcaaag accgaaaccg ccctgaccga gctcgccgga cgactgcacg   3300
acgccgtcga cgacaccgtc gccctcccgg cggtggccgc caccctcgcc accggacgcg   3360
```

```
cccacctgcc ctaccgggcc gccctgctgg cccgcgacca cgacgaactg cgcgacaggc    3420
tgcgggcgtt caccactggt tcggcggctc ccggtgtggt gtcggggtg gcgtcgggtg     3480 gtggtgtggt gtttgttttt cctggtcagg gtggtcagtg ggtggggatg gcgcgggggt    3540
tgttgtcggt tccggtgttt gtggagtcgg tggtggagtg tgatgcggtg gtgtcgtcgg    3600 tggtgggggtt ttcggtgttg ggggtgttgg agggtcggtc gggtgcgccg tcgttggatc   3660
gggtggatgt ggtgcagccg gtgttgttcg tggtgatggt gtcgttggcg cggttgtggc    3720
ggtggtgtgg ggttgtgcct gcggcggtgg tgggtcattc gcaggggag atcgcggcgg     3780 cggtggtggc gggggtgttg tcggtgggtg atggtgcgcg ggtggtggcg ttgcgggcgc    3840
gggcgttgcg ggcgttggcc ggccacggcg gcatggtctc cctcgcggtc tccgccgaac    3900
gcgcccggga gctgatcgca ccctggtccg accggatctc ggtggcggcg gtcaactccc    3960
cgacctcggt ggtggtctcg ggtgacccac aggccctcgc cgcccctcgtc gcccactgcg   4020 ccgagaccgg tgagcgggcc aagacgctgc ctgtggacta cgcctcccac tccgcccacg    4080
tcgaacagat ccgcgacacg atcctcaccg acctggccga cgtcacgcg cgccgacccg     4140 acgtcgccct ctactccacg ctgcacggcg cccggggcgc cggcacggac atggacgccc    4200
ggtactggta cgacaacctg cgctcaccgg tgcgcttcga cgaggccgtc gaggccgccg    4260
tcgccgacgg ctaccgggtc ttcgtcgaga tgagcccaca cccggtcctc accgccgcgg    4320
tgcaggagat cgacgacgag acggtggcca tcgctcgct gcaccgggac accggcgagc     4380
ggcacctggt cgccgaactc gcccgggccc acgtgcacgg cgtaccagtg gactggcggg    4440
cgatcctccc cgccacccac ccggttcccc tgccgaacta cccgttcgag gcgacccggt    4500
actggctcgc cccgacggcg gccgaccagg tcgccgacca ccgctaccgc gtcgactggc    4560 ggccctggc caccacccg gcggagctgt ccggcagcta cctcgtcttc ggcgacgccc       4620
cggagaccct cggccacagc gtcgagaagg ccggcgggct cctcgtcccg gtggccgctc    4680
ccgaccggga gtccctcgcg gtcgccctgg acgaggcggc cggacgactc gccggtgtgc    4740
tctccttcgc cgccgacacc gccacccacc tggcccggca ccgactcctc ggcgaggccg    4800
acgtcgaggc cccactctgg ctggtcacca gcggcggcgt cgcactcgac gaccacgacc    4860
cgatcgactg cgaccaggca atggtgtggg ggatcgacg ggtgatgggt ctggagaccc     4920
cgcaccggtg gggcggcctg gtggacgtga ccgtcgaacc caccgccgag gacggggtgg    4980
tcttcgccgc cctcctggcc gccgacgacc acgaggacca ggtggcgctg cgcgacggca    5040
tccgccacgg ccgacggctc gtccgcgccc cgctgaccac ccgaaacgcc aggtggacac    5100
cggcgggcac ggcgctcgtc acgggcggta cgggtgccct cggcggccac gtcgcgcggt    5160
acctggcccg gtccggggtg accgatctcg tcctgctcag caggagcggc cccgacgcac    5220
ccggtgccgc cgaactggcc gccgaactgg ccgacctcgg ggccgagccg agagtcgagg    5280
cgtgcgacgt caccgacggg ccacgcctgc gcgccctggt gcaggagcta cgggaacagg    5340
accggccggt ccggatcgtc gtccacaccg caggggtgcc cgactcccgt cccctcgacc    5400
ggatcgacga actggagtcg gtcagcgccg cgaaggtgac cggggcgcgg ctgctcgacg    5460
agctctgccc ggacgccgac accttcgtcc tgttctcctc gggggcggga gtgtggggta    5520
gcgcgaacct gggcgcgtac gcggcagcca acgcctacct ggacgccctg cccaccgcc    5580 gccgccaggc gggccgggcc gcgacctcgg tcgcctgggg ggcgtgggcc ggcgacggca    5640
tggccaccgg cgacctcgac gggctgaccc ggcgcggtct gcgggcgatg gcaccggacc    5700
```

```
gggcgctgcg cgcctgcacc aggcgttgga ccacccacga cacctgtgtg tcggtagccg     5760
acgtcgactg ggaccgcttc gccgtgggtt tcaccgccgc ccggcccaga ccctgatcg      5820 acgaactcgt cacctccgcg ccggtggccg ccccaccgc tgcggcggcc ccggtcccgg      5880
cgatgaccgc cgaccagcta ctccagttca cgcgctcgca cgtggccgcg atcctcggtc     5940
accaggaccc ggacgcggtc gggttggacc agcccttcac cgagctgggc ttcgactcgc     6000
tcaccgccgt cggcctgcgc aaccagctcc agcaggccac cgggcggacg ctgcccgccg     6060
ccctggtgtt ccagcacccc acggtacgca gactcgccga ccacctcgcg cagcagctcg     6120
acgtcggcac cgcccggtc gaggcgacgg gcagcgtcct gcgggacggc taccggcggg       6180
ccgggcagac cggcgacgtc cggtcgtacc tggacctgct ggcgaacctg tcggagttcc     6240
gggagcggtt caccgacgcg gcgagcctgg gcggacagct ggaactcgtc gacctggccg     6300
acggatccgg cccggtcact gtgatctgtt gcgcgggcac tgcggcgctc tccgggccgc     6360
acgagttcgc ccgactcgcc tcggcgctgc gcggcaccgt gccggtgcgc gccctcgcgc     6420
aacccgggta cgaggcgggt gaaccggtgc cggcgtcgat ggaggcagtg ctcggggtgc     6480
aggcggacgg ggtcctcgcg gcacagggcg acacgccgtt cgtgctggtc ggacactcgg     6540
cgggggccct gatggcgtac gccctggcga ccagctggc cgaccggggc cacccgccac      6600
gtggcgtcgt gctcctcgac gtgtaccac ccggtcacca ggaggcggtg cacgcctggc      6660
tcggcgagct gaccgccgcc ctgttcgacc acgagaccgt acggatggac gacacccggc     6720
tcacggccct gggggcgtac gacaggctga ccggcaggtg gcgtccgagg gacaccggtc     6780
tgcccacgct ggtggtggcc gccagcgagc cgatggggga gtggccggac gacggttggc     6840
agtccacgtg gccgttcggg cacgacaggg tcacggtgcc cggtgaccac ttctcgatgg     6900
tgcaggagca cgccgacgcg atcgcgcggc acatcgacgc ctggttgagc ggggagaggg     6960
catgaacacg accgatcgcg ccgtgctggg ccgacgactc cagatgatcc ggggactgta     7020
ctggggttac ggcagcaacg gagacccgta cccgatgctg ttgtgcgggc acgacgacga     7080
cccgcaccgc tggtaccggg ggctgggcgg atccggggtc cggcgcagcc gtaccgagac     7140
gtgggtggtg accgaccacg ccaccgccgt gcgggtgctc gacgacccga ccttcacccg     7200
ggccaccggc cggacgccgg agtggatgcg ggccgcgggc gccccggcct cgacctgggc     7260
gcagccgttc cgtgacgtgc acgccgcgtc ctggacgcc gaactgcccg acccgcagga      7320
ggtggaggac cggctgacgg gtctcctgcc tgccccgggg accgcctgg acctggtccg      7380 cgacctcgcc tggccgatgg cgtcgcgggg ggtcggcgcg gacgacccg acgtgctgcg      7440 cgccgcgtgg gacgcccggg tcggcctcga cgcccagctc accccgcagc ccctggcggt     7500
gaccgaggcg gcgatcgccg cggtgcccgg ggacccgcac cggcgggcgc tgttcaccgc     7560
cgtcgagatg acagccaccg cgttcgtcga cgcggtgctg gcggtgaccg ccacggcggg     7620
ggcggcccag cgtctcgccg acgacccga cgtcgccgcc cgtctcgtcg cggaggtgct      7680
gcgcctgcat ccgacggcgc acctggaacg gcgtaccgcc ggcaccgaga cggtggtggg     7740
cgagcacacg gtcgcggcgg gcgacgaggt cgtcgtggtg gtcgccgccg caaccgtga    7800 cgcggggtc ttcgccgacc cggaccgcct cgacccggac cgggccgacg ccgaccgggc      7860
cctgtccgcc cagcgcggtc accccggccg gttggaggag ctggtggtgg tcctgaccac     7920
cgccgcactg cgcagcgtcg ccaaggcgct gccggtctc accgccggtg gcccggtcgt      7980
caggcgacgt cgttcaccgg tcctgcgagc caccgcccac tgcccggtcg aactctgagg     8040
tgcctgcgat gcgcgtcgtc ttctcctcca tggccagcaa gagccacctg ttcggtctcg     8100
```

```
ttccctcgc ctgggccttc cgcgcggcgg gccacgaggt acgggtcgtc gcctcaccgg   8160
ctctcaccga cgacatcacg gcggccggac tgacggccgt accggtcggc accgacgtcg   8220
accttgtcga cttcatgacc cacgccgggt acgacatcat cgactacgtc cgcagcctgg   8280
acttcagcga gcgggacccg gccacctcca cctgggacca cctgctcggc atgcagaccg   8340
tcctcacccc gaccttctac gccctgatga gcccggactc gctggtcgag ggcatgatct   8400
ccttctgtcg gtcgtggcga cccgactggt cgtctggacc gcagaccttc gccgcgtcga   8460
tcgcggcgac ggtgaccggc gtgggccacg cccgactcct gtggggaccc gacatcacgg   8520
tacgggcccg gcagaagttc ctcgggctgc tgcccggaca gcccgccgcc caccgggagg   8580 acccctcgc cgagtggctc acctggtctg tggagaggtt cggcggccgg gtgccgcagg   8640
acgtcgagga gctggtggtc gggcagtgga cgatcgaccc cgccccggtc gggatgcgcc   8700
tcgacaccgg gctgaggacg gtgggcatgc gctacgtcga ctacaacggc cgtcggtgg   8760 tgccggactg gctgcacgac gagccgaccc gccgacgggt ctgcctcacc ctgggcatct   8820
ccagccggga gaacagcatc gggcaggtct ccgtcgacga cctgttgggt gcgctcggtg   8880
acgtcgacgc cgagatcatc gcgacagtgg acgagcagca gctcgaaggc gtcgcccacg   8940
tcccggccaa catccgtacg gtcgggttcg tcccgatgca cgcactgctg ccgacctgcg   9000
cggcgacggt gcaccacggc ggtcccggca gctggcacac cgccgccatc cacggcgtgc   9060
cgcaggtgat cctgcccgac ggctgggaca ccggggtccg cgcccagcgg accgaggacc   9120 aggggcggg catcgccctg ccggtgcccg agctgacctc cgaccagctc cgcgaggcgg   9180
tgcggcgggt cctggacgat cccgccttca ccgccggtgc ggcgcggatg cgggccgaca   9240
tgctcgccga gccgtccccc gccgaggtcg tcgacgtctg tgcggggctg gtcgggggaac   9300 ggaccgccgt cggatgagca ccgacgccac ccacgtccgg ctcggccggt gcgccctgct   9360
gaccagccgg ctctggctgg gtacggcagc cctcgccggc caggacgacg ccgacgcagt   9420
acgcctgctc gaccacgccc gttcccgggg cgtcaactgc ctcgacaccg ccgacgacga   9480
ctctgcgtcg accagtgccc aggtcgccga ggagtcggtc ggccggtggt tggccgggga   9540
caccggtcgg cgggaggaga ccgtcctgtc ggtgacggtg ggtgtcccac cgggcgggca   9600
ggtcggcggg ggcggcctct ccgcccggca gatcatcgcc tcctgtgagg gctccctgcg   9660
gcgtctcggt gtcgaccacg tcgacgtcct tcacctgccc cgggtggacc gggtggagcc   9720
gtgggacgag gtctggcagg cggtggacgc cctcgtggcc gccggaaagg tctgttacgt   9780
cgggtcgtcg ggcttccccg gatggcacat cgtcgccgcc caggagcacg ccgtccgccg   9840
tcaccgcctc ggcctggtgt cccaccagtg tcggtacgac ctgacgtcgc gccatcccga   9900
actggaggtc ctgcccgccg cgcaggcgta cgggctcggg gtcttcgcca ggccgacccg   9960
cctcggcggt ctgctcggcg gcgacggtcc gggcgccgca gccgcacggg cgtcgggaca  10020
gccgacggca ctgcgctcgg cggtggaggc gtacgaggtg ttctgcagag acctcggcga  10080 gcacccgcc gaggtcgcac tggcgtgggc gctgtcccgg ccggtgtgg cggggcggt  10140 cgtcggtgcg cggacgcccg acggctcga ctccgcgctc cgcgcctgcg gcgtcgccct  10200
cggcgcgacg gaactcaccg ccctggacgg gatcttcccc gggtcgccg cagcaggggc  10260 ggcccgagag gcgtggctac ggtgagagcc cgccctgac ctgcgggaac ccgtgtcggt  10320
gcggcgggac ggccgccgcg gtccccgccc cggtcagccg gtgggggtga gccgcagcag  10380
gtccggcgcc accgactcgg ccacctcccc gacgtggtcg gcgaggtaga agtgcccgcc  10440
```

```
cgggaaggtc cgggtacggc cggggactac cgagtacggc agccagcgtt gggcgtcctc    10500
caccgtcgtc aacgggtcgg tgtcaccgca gagggtggtg atgccggccc gcagcggcgg    10560
cccggcctgc caggcgtagg agcgcagcac ccggtggtcg gcccgcagca ccggcagcga    10620
catgtccaac agccctggt cggccaatgc ggcctcgctg accccgagcc tgcgcatctg     10680
ctcgacgagt ccgtcctcgt cgggcaggtc ggtgcgccgc tcgtggaccc ggggggcggt    10740
ctgcccggag acgaacaacc gcagcggtcg cacccccgga cgagcctcca ggcgacgggc    10800
ggtctcgtag gcgaccaggg cgcccatgct gtgaccgaac agggcgaacg gaacctcgcc    10860
gacgaggtcg cgcagcacgg ccgcgacctc gtcggcgatc tccccggcgg tgccgagagc    10920
ccgctcgtca cgtcggtcct gccggcccgg gtactgcacc gcccacacgt cgacctccgg    10980
ggccagtgcc cgggcgaggt cgaggtacga gtcggcggcg gctcccgcgt gcgggaagca    11040
gtacagccgg gcccggtgtc cgtcggcgga cccgaaccgc cgcaaccagg tgttcatcgg    11100
tgtctcatcc gttcggtcgc accggcaggt ggtcgatgcc gcgcagcagg agcgaccgcc    11160
gccagacaac ctcgtcggag gggaagccca gcgacagctt cgggaagcgg tcgaacaggg    11220
cccccagggc gacctctccc tccagcttgg ccagcgggcg gcccatgcag tagtggatgc    11280
cgtgcccgaa ggtgaggtgt ccccggctgt ccctggtgac gtcgaaccgg tcgggtcgg    11340 ggaactgtcc cgggtcgcgg ttggccgccc cgttggcgat caggacggtg ctgtacgccg    11400
ggatcgtcac cccgccgatc tccacctcgg cggtggcgaa ccgggtggtg gtctccggtg    11460
gggcctggta gcgcaggatc tcctccaccg ctccgggcag cagtgccggg tccttccgga    11520
ccagcgcgag ctggtcgggg tgggtcagca gcaggtaggt gccgatcccg atgaggctca    11580
ccgacgcctc gaatcccgcc agcagcagca ccagcgcgat ggaggtgagt tcgtcgcggc    11640
tgagccggtc ggcgtcgtcg tcctggaccc ggatcagggc cgagagcagg tcgttgccgg    11700
gctcggtacg gcgcgctcg accaggtcga tgatgaaggt gacgacctcc tgggcggcct    11760
ggccgcgctg cgcggcgcgc tcgggttcca tgacgaggat ctccgagctc caccggccga    11820
agtcgccccg gtccttctcg tccaccccga gcagttcgca gatcaccttg atgggcaggg    11880
gatgggcgaa ccggtcgacg atgtcgacct cgtcgacgtc gccgatctcg tcgagcagtt    11940
gcgcggtgat cgcctcgacc cggggacgca tggcctccac ccggcgggcg gtgaactcct    12000
gggagaccag cttgcgcagc cgggtgtggg tgggcgggtc gctggtgccc atgttgttga    12060
cgaagtagtg ccgtacgtcc tcggggaagc ccaggtaggc ggggaactcc acctccaccc    12120
ccgggtactt cttcttcggg tcgctgctca accgcaggtc gcccagggcg gtacgggcct    12180
cctcgtagcc ggtgatcagc caggcgtcct ggccgaagaa gcgcaccggg gtcaccgggg    12240
cccgttcgcg cagctccgca taggtccggt accagtcgac gtggaaggcg tcgctctcca    12300
gatcgggcag tttcatcaca ccacttccag gtggggagg gggaagacga gcttgccgcc    12360
gttggcgagg aactcctgtt cccgttcgag gaagccgtcg cggtagatcc agggcaggac    12420
gaggagctgg tcggggcggc gggacttcgc ctcctcctcc gacacgatcg ggatcccggt    12480
gcccggggtg taccggccgg acttctccgg gctgacctcc ccgatgcagg gcaggtcgtc    12540
ctcggtgagt ccgcagtact gcaggatcac gttgcccttc gtcgaggcgc cgtaccccag    12600
ggtcagtttg ccggcggcgc gcgacgtggc gaggaagtcc agcaggtggt cgcgttggcg    12660
ctcggtgttg cgggcgaatg cctcgtaggg cgccagggtg tcgagccggg cggcggtctc    12720
ctggtccccg atcttctgca gcgccggctc gttcacccgg tggtcgctgg tctgccggc    12780 cagcacggca cagaggcttc cgccgtacac gtcggtgatc tcggcgtcga ccaccttcag    12840
```

```
cccggtgcgt tcggccatcc actcgatctg ccgcagggcg tagtactcaa ggtgttcgtg   12900
gcagacgatg tcgtaggcgc tggcctccag catggagggc aggtagctct gctccatcag   12960
ccacaggccg tcgggggcga ggatgtcgtg gacgtcgcgc atgaactccg tcggcgcggg   13020
caggtcgtag aacatcgcga tggaggtgac gatcgcggcg cgccggtccc cgtagcgctc   13080
ggtgaacgcc tcggcggaga agaagccggc gacgaggtcg gcctccggtg ggtacaggtc   13140
gcggaacttc tctcccacca ggtcgaaccc gaccagcttc ggcgggtcgg ggaggtagcc   13200
ccgcagcagg gtggagtcgt tgctgccgat gtcgaccacg aggtcgtcgg ggccgacctc   13260
gcgcatgccg cgcagcttgg cgaccttgtc gtgcaggtgg ttgatcatga aggggcggat   13320
gccggaccgt tagccgtaac cctcgttgta catcagtccg aagtcgggcg tctcgcgcag   13380
ctggaccagt ccgcagccgg gcggcgcgca ggtcaccagt tccagcggaa acgtggggac   13440
gacgtcgtct gggctgtgcg ggaagacccc ggtgagggcc tgttctccca gatgcagtac   13500
tgattcgaga tcttcatttc cgcagatacg gcatctcgtt tcgggcatcg cctgagtgta   13560
gcgatcaaaa actgatatcg attgatgcgt gagccagatc acacggaatt tccggcctgt   13620
ggtgcgggtg caggaatgtg tcggtgcgcg ggatgcgtcc gcatctcggg cggcgtccac   13680 cgacccctg cgtcggggtc acgaaccgct ctccacctgc acagatgctt cgcctgccga   13740
cctgccgtgc caaggttcgc gaggtgcctg cggggtcgat ggcccgccga atacggggca   13800
tcattgatgg tcaagcgact atgtatcgag ctggggaggt aattgcgtcg gggtggagtc   13860
cgacgtcagt cgagaatgcc gttcgccgac caccggtggt cgccgctcgg ctgtcggtgc   13920
cggtccctca caccatcgcc cgggcgcgta acgcctccca ccagggtcgg ttgtcgcggt   13980
accagcggac ggtgtcggcg agccccgcac ggaagtcgac ccgggggtg taccccaact   14040 cgcgtcgggc cttcgagcag tcgagtgagt agcgccggtc gtggcccttg cggtccgaga   14100
cgtgccgcac ccggtcccag ccggcgtcgc aggcggcgag cagcagaccg gtcagttccc   14160
ggttggacag ctccgtgccc cgccgatgt ggtagatctc cccggcccgg ccccgcgtac   14220
gggccaactc gatcccgtgg acgtggtcgt cgacgtgcag ccagtcccgt acgttgccac   14280
cgtcgccgta gagcggcacc gtctcccgt cgaggagtcg ggtgatgaaa agggggatga   14340
gcttctccgg gaagtggtac ggcccgtacg tgttggagcc ccgggtcacc cggacgtcga   14400
gaccgtgcgt gtggtggtac gacagggcga cgagatcacc acccgccttc gacgccgagt   14460
acggggaact gggcttgagc gggtgcgtct ccggccacga gccgtgctcg atggagccgt   14520
acacctcgtc ggtcgagacg tggacgaacg tctcgacgcc ctgctggtga gccgcctcga   14580
tcagggtctg ggtgccgagc acgttggtac ggacgaacgc cgccccgccg tcgatcgacc   14640
tgtcgacgtg ggactcggcg gcgaagtgga ccacctggtc gtgctcgcgg gccagcgcgg   14700
tcaccgtcgc ggcgtcgcag atgtcaccct ggacgaacgt gtacctcggg tggtcgcgca   14760
ggcccgccag gttctccggg ttaccggcgt aggtgagggc gtccaggacc gtgacccgta   14820
cgtcggtcgg cccgtccggg ccgagcaggg tacggacgta gtgcgaaccg atgaatccgg   14880
caccgccggt gaccaggagt cgagtcgtca tgacgagatc tgcaccttgc tgtgatcgcc   14940
gagcacgaac cggtgggcgg cggggttgcg cggcgcgggg gtgacctcca cgccacgtcc   15000
gatcagtgac gcctcgaccc ggcggacgcc ggtgagtgcc gagtcccgca acacgatcga   15060
gtactcgatc tcggtgtcct cgatccggca gcactcgccg atcgctgtga acggcccgac   15120
gtaggagtcg acgacctccg tcgaggcgcc gatgaccgcc gggccgacga tacggcttcc   15180
```

```
gctgatccgc gcgccccgat cgatccgtac ccggccgatg atctcgctgg tggcgtcgac    15240
cgtaccggcc acccgggtct cgatggtctc cagcacggaa cggttcacct ccagcatgtc    15300
ggtcacgttg ccggtgtcct tccagtatcc ggagatgatc gtcgaccgga cgtcgcactc    15360
gcggtcgatg agccactgga tggcgtgagt gatctccagt tcccccgct cggacggggt    15420 gatgacccgt accgcctcgt ggaccaccgg cgtgaacagg tagacccga ccagggcgag    15480 gtcgctcttg gcgtgctgtg gcttctcctc caggctgacc acccgccgt cgacgagttc    15540 ggcgaccccg aagtgccggg ggtccgccac gtgggtcagc aggatgtgcg cgtcggggcg    15600
ggcctgccgg aagtcgtcga ccaggtcgcg gatcccgccg acgatgaagt tgtcgcccag    15660
gtacatgacg aagtcgtcgt caccgaggta gtcgcgggcg atcaggacgg cgtgggcgag    15720
gcccagcggc gcgtgctggc ggatgtaggt cactgagatg ccgaactccg agccgtcccc    15780
cacggcggcc atgatctcgt cggcggtgtc acccacgatg atgccgacgt cgcggatgcc    15840
ggactcagcg atggcctcca gcccgtagaa gagcaccggc ttgttggcca ccggcaccaa    15900
ctgcttggcg gacgtgtgcg tgatgggtcg taggcgggta cccgctccgc ccgacaggac    15960
aagcgccttc atgtgacccc ccggggcacc agagatgagc cgtccactgt cggaaccagg    16020
ttggcggcga cggctacagg acaggtcgag cctcggctga gggaccaccc gcaccagagg    16080
gggaggcgtg cggcggcgct acgcgccgcg tggggtggg ccgggtaggg acgtgccggg    16140
tggggacgtg cagcggcccg gcgtgcggac gacccggcgg ccgggcaccc ggcatcccca    16200
ggaactgcgg cggcgggccg gggtggcggc gcgatgcggc acggggcgt ccggcggtcc    16260 gggcgagcgc gacaccacgt cgtacgcggt cgcggctggt gggtggtggc cggggggcctt    16320 gtcgccctac ttcttgtcgc ggcgaccggt ggcgaggatc cgctcccgcc ggggcgggac    16380
gacgtcggcg gtcgacgtct cgtccggccc ggccgggtcg gtggtgtcct tcttggccag    16440
ctgctggagg cggagctgac cgcaggcggc ttcgatgtcc tggccctggg tgtcccggac    16500
ggtgacgttg accccggcgg agtccaactc gcgccggacg gtgctcagtc gccggtcact    16560
gacccgctgg aagagcggac cgcccaggac cggattccac cgcatcaggt tgatccgagc    16620
cggtcgacct gcgaagaact ggatcagacg ggtgacgtcg tcgtcggagt cgttcacatt    16680
gggaagcagg aggtaaacga aggtgacgat ccgaccgtgc cgctccgccc acgacaacgc    16740
accctcgacg acctcgttga tgtcgtgatt gcgtgatccc gggatcagtt cggtccgcga    16800
ctcctgcgtg gtcgcgtgca gggaaatggt cagattgatc ttgatgtgct cttcacgcag    16860
gcgcttcagc gacttcggga taccgatcgt ggagatggtg atcccactgg tcttgaagcc    16920
gagcccgcgc cgttcgcgga gaatgcgaat ggagcccatg acgttgtcgt agttgtgcag    16980
gggctcgccc atgcccatga acacgagcct gttgacgccg ggcccgagcg ccagcacctg    17040
ctgcacgatc tcgcccggta gcaggtgtcg cttgaggccg tcgcggcccg acgcgcagaa    17100
ctggcacgcg aaggcgcacc ccgcctgaga cgagacgcag gcggtgtagc cgtcgtggcg    17160
acggatccgc accgtctcga tgaaattgcc gtcgaccagc tcgaacagga actttgtcgt    17220
ctggcttccc ctggtgcgac tgcgctcggc gagggtcgac gagaggtcgt cgagttgccc    17280
gtagtgcttc agcgtgtggg ccgagtcttt gcgctgccga taaagcttgt cgaagatgtc    17340
ggctgcttgc cgttcgccgc cgacgcgctc cgcgagctcg gagaacgaca ggtcgaagac    17400
cgacggcgcg acgggtcgtc gtcgccgaat gggtagaccc acgacctggg gcgaagctga    17460
catagtcacc accctatcac ggtgcaagag acgtcaattc gtcaagtgac cacagaggag    17520
cctgacgatg gacgatgctc tcgtgtcttc gccatatagc cgttgagctg ccaattcacg    17580
```

-continued aacgcgcagc gggcgc                                                17596

<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3
taagaattcg gagatctggc ctcagctcta gac                              33

<210> SEQ ID NO 4
<211> LENGTH: 39
<212> TYPE: DNA
<213> ORGANISM: Artificial Sequence
<220> FEATURE:
<223> OTHER INFORMATION: Synthetic Construct

<400> SEQUENCE: 4
aattgtctag agctgaggcc agatctccga attcttaat                        39

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ggggtcatat gaaggcgctt gtcctgtcgg                                  30

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
gcaaagcttg tgactagtcg agtagtc                                     27

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gacctccata tgacgactcg actcctggtc                                  30

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
tactagtccc tcacaccatc gcccg                                       25

<210> SEQ ID NO 9
<211> LENGTH: 26
<212> TYPE: DNA

```
<213> ORGANISM: Artificial Sequence
<220> FEATURE:
<223> OTHER INFORMATION: Primer

<400> SEQUENCE: 9
cagcatatgc ccgaaacgag atgccg                                       26

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
atcgactagt ttcatcacac cacttccagg                                   30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
gcatatgaca agacatgtca cacttctcgg                                   30

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
cccactagtg tcactccttg gtcgagatga                                   30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
tggtcatatg aaactgcccg atctggagag                                   30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
catactagtc tcatccgttc ggtcgcaccg                                   30

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
ccgggcatat gagggtcgag gagctg                                       26
```

```
<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
gcacactagt ccggggtcac gtccgc                                          26

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
tgtacatatg cgggtcctgc tcacctcg                                        28

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
acactagtca cctgtcggcg cggtgctg                                        28

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ccgtcatctg agcaccgacg ccac                                            24

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
aggactagtg cgggctctca ccgtag                                          26

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
ggcatatggg ggatcgggtc aacggtcatg                                      30

<210> SEQ ID NO 22
<211> LENGTH: 31
<212> TYPE: DNA
<213> ORGANISM: Artificial Sequence
<220> FEATURE:
```

-continued

```
<223> OTHER INFORMATION: Primer

<400> SEQUENCE: 22
gtactagttt cacgccgtcg cccggttgta g                                    31

<210> SEQ ID NO 23
<211> LENGTH: 37
<212> TYPE: DNA
<213> ORGANISM: Artificial Sequence
<220> FEATURE:
<223> OTHER INFORMATION: Primer

<400> SEQUENCE: 23
tctagaagga gatatacata tgtgaactag tgaattc                              37

<210> SEQ ID NO 24
<211> LENGTH: 57
<212> TYPE: DNA
<213> ORGANISM: Artificial Sequence
<220> FEATURE:
<223> OTHER INFORMATION: Primer

<400> SEQUENCE: 24
tctagaagga gatatacaat gcaccaccac caccaccata tgtgaactag tgaattc        57
```